US012806235B2

(12) United States Patent
Seo et al.

(10) Patent No.: US 12,806,235 B2
(45) Date of Patent: Nov. 24, 2026

(54) ***AKKERMANSIA MUCINIPHILA* EB-AMDK19 STRAIN AND USE THEREOF**

(71) Applicant: ENTEROBIOME INC., Goyang-si (KR)

(72) Inventors: Jae-Gu Seo, Gimpo-si (KR); Joo-Hyun Shin, Seoul (KR); Do-Kyung Lee, Seoul (KR)

(73) Assignee: ENTEROBIOME INC., Goyang-si (KR)

( * ) Notice: Subject to any disclaimer, the term of this patent is extended or adjusted under 35 U.S.C. 154(b) by 773 days.

(21) Appl. No.: 17/258,522

(22) PCT Filed: May 11, 2020

(86) PCT No.: PCT/KR2020/006179
§ 371 (c)(1),
(2) Date: Jan. 7, 2021

(87) PCT Pub. No.: WO2021/040187
PCT Pub. Date: Mar. 4, 2021

(65) Prior Publication Data

US 2022/0133812 A1 May 5, 2022

(30) Foreign Application Priority Data

Aug. 23, 2019 (KR) ........................ 10-2019-0103511
Mar. 19, 2020 (KR) ........................ 10-2020-0033878

(51) Int. Cl.
*A61K 35/74* (2015.01)
*A23L 33/135* (2016.01)
*A61P 3/04* (2006.01)
*A61P 3/06* (2006.01)
*A61P 3/10* (2006.01)
*C12N 1/205* (2026.01)

(52) U.S. Cl.
CPC ............ *A61K 35/74* (2013.01); *A23L 33/135* (2016.08); *A61P 3/04* (2018.01); *A61P 3/06* (2018.01); *A61P 3/10* (2018.01); *C12N 1/205* (2021.05)

(58) Field of Classification Search
CPC ..... A61K 35/74; A61K 35/741; A23L 33/135; A61P 3/04; A61P 3/06; A61P 3/10; A61P 3/00; A61P 29/00; A61P 1/00; A61P 1/16; A61P 5/50; C12N 1/205; C12N 1/20; A23V 2002/00; A23V 2200/3262; A23V 2200/328; C12R 2001/01
See application file for complete search history.

(56) References Cited

U.S. PATENT DOCUMENTS

2015/0306152 A1* 10/2015 Cani ...................... A61P 37/04
424/93.4

FOREIGN PATENT DOCUMENTS

| | | | | |
|---|---|---|---|---|
| CN | 104918626 A | | 9/2015 | |
| CN | 108289918 A | | 7/2018 | |
| KR | 10-0996577 B1 | | 11/2010 | |
| KR | 10-2011-0095929 A | | 8/2011 | |
| KR | 10-2013-0021920 A | | 3/2013 | |
| KR | 10-2015-0093711 A | | 8/2015 | |
| KR | 10-2015-0133646 A | | 11/2015 | |
| KR | 10-1809172 B1 | | 12/2017 | |
| KR | 10-2019-0034796 A | | 4/2019 | |
| WO | 2017/042347 A1 | | 3/2017 | |
| WO | WO-2017060698 A1 | * | 4/2017 | ........... A61K 35/741 |
| WO | 2020/076136 A2 | | 4/2020 | |

OTHER PUBLICATIONS

Huyghebaert et al. (In vitro evaluation of coating polymers for enteric coating and human ileal targeting, International Journal of Pharmaceutics 298 (2005) 26-37) (Year: 2005).*
Bocian et al. (Metabolite profiling during cold acclimation of Lolium perenne genotypes distinct in the level of frost tolerance, J Appl Genetics (2015) 56:439-449) (Year: 2015).*
Khoder et al. (A novel natural GRAS-grade enteric coating for pharmaceutical and nutraceutical products, International Journal of Pharmaceutics 584 (2020) 119392) (Year: 2020).*
Pyar et al. (Enteric coating of granules containing the probiotic *Lactobacillus acidophilus*, Acta Pharm. 64 (2014) 247-256) (Year: 2014).*
Evonik (EUDRAGIT® L 30 D-55, Evonik Industries AG, May 2014) (Year: 2014).*
Extended European Search Report dated Jun. 8, 2022 in European Application No. 20824073.9.
Hubert Plovier et al., "A purified membrane protein from Akkermansia muciniphila or the pasteurized bacterium improves metabolism in obese and diabetic mice", Nature Medicine, 2017, vol. 23, No. 1, pp. 107-116 (10 pages total).
International Searching Authority, International Search Report of PCT7KR2020/006179 dated Aug. 18, 2020 [PCT/ISA/210].
International Searching Authority, Written Opinion of PCT7KR2020/006179 dated Aug. 18, 2020 [PCT/ISA/237].

(Continued)

*Primary Examiner* — Louise W Humphrey
*Assistant Examiner* — Alexander M Duryee
(74) *Attorney, Agent, or Firm* — Sughrue Mion, PLLC

(57) ABSTRACT

A novel *Akkermansia muciniphila* strain is disclosed. The novel strain has effects of preventing or treating inflammatory or metabolic diseases. A composition containing the novel strain or a culture thereof are also disclosed. The novel strain, cultures thereof, or compositions containing the novel strain and/or cultures thereof are suitable to use in methods of preventing or treating inflammatory or metabolic diseases.

11 Claims, 35 Drawing Sheets

Specification includes a Sequence Listing.

(56) References Cited

OTHER PUBLICATIONS

Genbank Accession No. ACD05451.1 11, carboxyl-terminal protease [Akkermansia muciniphila ATCC BAA-835], Retrieved on Jan. 6, 2021, 2 pages.
Office Action issued May 10, 2024, in Chinese Application No. 202080026353.2.
Communication dated Mar. 9, 2026, in Indian Application No. 202227007111.
Everard, et al., "Cross-talk between *Akkermansia muciniphila* and intestinal epithelium controls diet-induced obesity", PNAS, May 28, 2013, vol. 110, No. 22, pp. 9066-9071 (6 pages).
Depommier et al., "Supplementation with *Akkermansia muciniphila* in overweight and obese human volunteers: a proof-of-concept exploratory study", Nat Med., Jul. 1, 2019, vol. 25, No. 7, pp. 1-28 (28 pages).
Collado, et al., "Intestinal Integrity and *Akkermansia muciniphila*, a Mucin-Degrading Member of the Intestinal Microbiota Present in Infants, Adults, and the Elderly", Applied and Environmental Microbiology, Dec 2007, vol. 73, No. 23, pp. 7767-7770 (4 pages).
Derrien, et al., "*Akkermansia muciniphila* gen. nov., sp. nov., a human intestinal mucin-degrading bacterium", International Journal Systematic and Evolutionary Microbiology, 2004, vol. 54, pp. 1469-1476 (8 pages).

* cited by examiner

[a]*Streptococcus pyogenes* ATCC 19615 (β-hemolysis)

* Control vs
LPS vs

* Control vs
LPS vs

*AKKERMANSIA MUCINIPHILA* EB-AMDK19 STRAIN AND USE THEREOF

CROSS REFERENCE TO RELATED APPLICATIONS

This application is a National Stage of International Application No. PCT/KR2020/006179 filed on May 11, 2020, claiming priority based on Korean Patent Application No. 10-2019-0103511 filed on Aug. 23, 2019 and Korean Patent Application No. 10-2020-0033878 filed on Mar. 19, 2020.

INCORPORATION BY REFERENCE OF SEQUENCE LISTING

The instant application contains a Sequence Listing which has been filed electronically in txt format and is hereby incorporated by reference in its entirety. Said txt file was created on Jan. 31, 2021, is named Q259712SubstituteSequenceListing222021.txt and is 13,900 bytes in size.

TECHNICAL FIELD

The present invention relates to an *Akkermansia muciniphila* strain and the use thereof, and more particularly to a novel *Akkermansia muciniphila* strain which has the effect of preventing or treating inflammatory disease or metabolic disease, and a pharmaceutical composition for the prevention or treatment of inflammatory disease or metabolic disease, which contains the *Akkermansia muciniphila* strain.

BACKGROUND ART

Inflammatory diseases refer to diseases that are caused by inflammatory cytokines, such as tumor necrosis factor-α (TNF-α), interleukin-1 (IL-1), IL-6, prostaglandin, leukotriene or nitric oxide (NO), which are secreted from immune cells such as macrophages due to an exaggerated reaction of the human body's immune system to harmful stimuli such as inflammatory agents or radiation.

Inflammatory diseases, such as inflammatory bowel disease (IBD), are a family of chronic, recurrent, and tissue-destructive diseases, characterized by dysfunction of mucosal T cells, abnormal cytokine production and cellular inflammation, which cause mucosal damage. Inflammatory diseases are serious diseases that dramatically decrease the quality of life, but the causes thereof still remain unclear.

When inflammatory bowel disease is taken as an example, one of the current treatments is a method of removing colon ulcers by colon resection, but this method may lower the quality of life and increase the risk of complications.

Meanwhile, other medical approaches include a method of controlling inflammation by suppressing the immune system using an immunomodulator, but the immunomodulator may induce an immune-lowering condition that makes the patient susceptible to various other diseases.

In order to overcome the adverse effects caused by conventional drugs or immunomodulators, studies using probiotics alone or in combination with antibiotics have been conducted. Research on the role of intestinal bacteria in promoting health has attracted more attention than research on pathogens.

In order to overcome the adverse effects caused by conventional drugs or immunomodulators, studies using probiotics alone or in combination with antibiotics have been conducted. As research on the role of intestinal bacteria in promoting health has been actively conducted, interest in lactic acid bacteria preparations has increased.

As technology for treating inflammation or obesity using probiotics, Korean Patent Application Publication No. 2011-0095929 discloses a *Lactobacillus reuteri* strain which interferes with in vivo lipid absorption, Korean Patent No. 0996577 discloses a *Lactobacillus curvatus* strain which lowers blood cholesterol levels and inhibits obesity, Korean Patent Application Publication No. 2011-0010015 discloses a *Lactobacillus johnsonii* which inhibits obesity while lowering blood cholesterol levels, and Korean Patent Application Publication No. 2019-0034796 discloses a *Lactobacillus plantarum* strain which has antioxidant and anti-inflammatory effects.

However, the probiotics as described above have insignificant effects on the amelioration of inflammatory disease or metabolic disease, and hence have a problem in that they are difficult to use as new preventive and therapeutic tools.

DISCLOSURE OF INVENTION

Technical Problem

The present invention is intended to overcome the above-described limitation of the conventional art, and an object of the present invention is to provide a next-generation probiotic strain which inhibits inflammatory response by reducing or inhibiting the release of one or more inflammatory factors, such as tumor necrosis factor-α (TNF-α), IL-8, IL-6 and IL-1β, and which is effective in preventing or treating inflammatory disease, obesity, obesity complications or metabolic disease by inhibiting adipocyte differentiation.

Another object of the present invention is to provide a pharmaceutical composition effective for the prevention or treatment of inflammatory disease or metabolic disease, which contains an *Akkermansia muciniphila* strain, which is the next-generation probiotic strain.

Another object of the present invention is to provide a pharmaceutical composition for suppressing appetite, which contains the *Akkermansia muciniphila* strain.

Still another object of the present invention is to provide a food useful for ameliorating inflammatory disease or metabolic disease, which contains the *Akkermansia muciniphila* strain.

Solution to Problem

One aspect of the present invention for achieving the above objects is directed to an *Akkermansia muciniphila* EB-AMDK19 strain (accession number KCTC 13761BP).

Another aspect of the present invention for achieving the above objects is directed to a pharmaceutical composition for preventing or treating inflammatory disease or metabolic disease, which contains the *Akkermansia muciniphila* EB-AMDK19 strain (accession number KCTC 13761BP), a culture thereof, or a dried product thereof.

Another aspect of the present invention for achieving the above objects is directed to a pharmaceutical composition for suppressing appetite, which contains the *Akkermansia muciniphila* EB-AMDK19 strain (accession number KCTC 13761BP), a culture thereof, or a dried product thereof.

Still another aspect of the present invention for achieving the above objects is directed to a food for preventing or ameliorating inflammatory disease or metabolic disease, which contains the *Akkermansia muciniphila* EB-AMDK19 strain (accession number KCTC 13761BP), a culture thereof, or a dried product thereof.

Advantageous Effects of Invention

The novel *Akkermansia muciniphila* EB-AMDK19 strain of the present invention inhibits inflammatory response by reducing or inhibiting the release of inflammatory factors, and is effective in treating inflammatory disease, particularly bowel inflammation, by maintaining the stability of intestinal microbiota.

The pharmaceutical composition containing, as an active ingredient, the *Akkermansia muciniphila* EB-AMDK19 strain of the present invention may be used as a pharmaceutical composition or a functional food composition for treating and/or preventing inflammatory disease or metabolic disease.

The novel *Akkermansia muciniphila* EB-AMDK19 strain of the present invention and the pharmaceutical composition containing the same may inhibit body weight gain and body fat accumulation, lower insulin resistance, lower total blood cholesterol levels, reduce the level of blood GPT that is a hepatotoxicity indicator, and reduce the levels of inflammatory cytokines, including IL-8, TNF-α, IL-6 and IL-1β. Thus, they may be useful for preventing or treating diabetes, obesity, insulin resistance, fatty liver, hyperlipidemia, or metabolic disease, which is associated with these factors.

In particular, the pharmaceutical composition of the present invention exhibits the effect of substantially inhibiting lipid accumulation by containing, as an active ingredient, the *Akkermansia muciniphila* EB-AMDK19 strain that reduces intracellular lipid accumulation, reduces expression of the adipocyte differentiation-related factor PPARγ, and also reduces the mRNA expression of CEBPα, aP2, CD36, ACC1, LPL (lipoprotein lipase), LDLR or FAS.

The composition for suppressing appetite containing the *Akkermansia muciniphila* EB-AMDK19 strain (KCTC 13761BP) of the present invention may suppress appetite by stimulating the secretion of appetite suppressant hormones.

MODE FOR THE INVENTION

Figure 1:
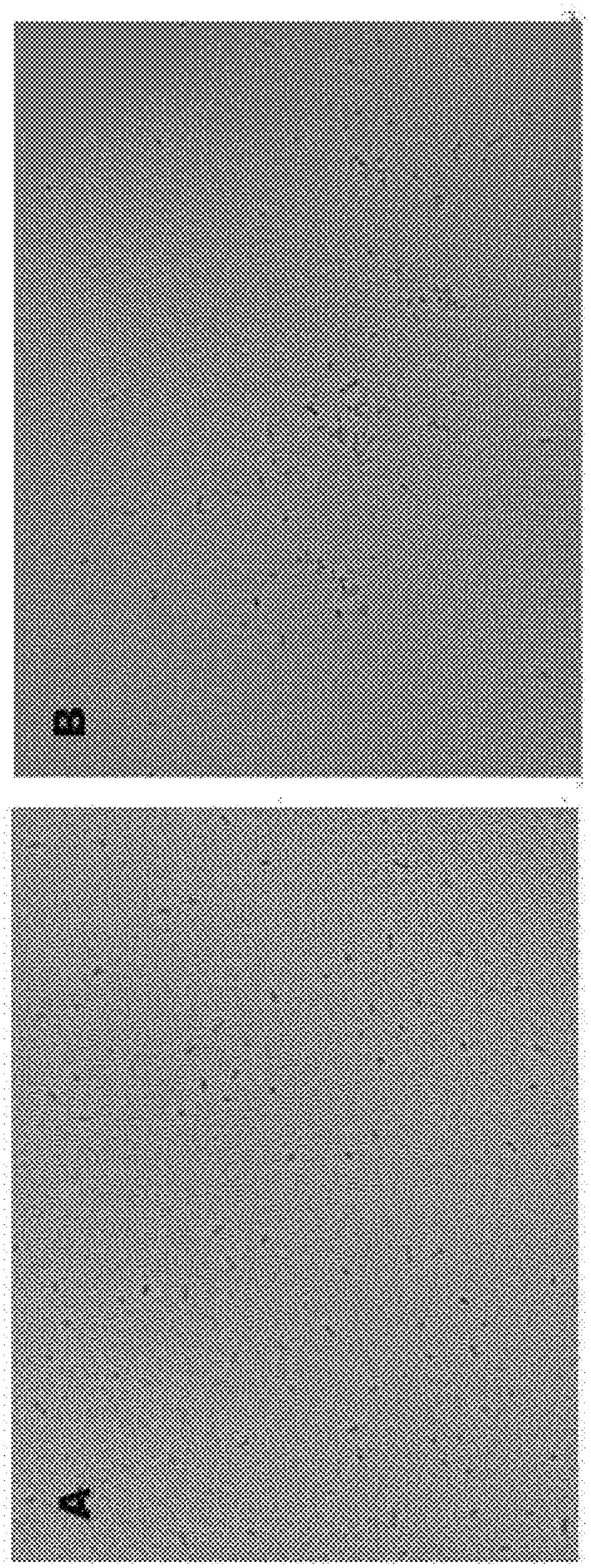
FIG. 1 shows micrographs of the *Akkermansia muciniphila* EB-AMDK19 strain (KCTC 13761BP) of the present invention and the type strain *Akkermansia muciniphila* ATCC BAA-835.

The present invention will be described in more detail below with reference to the accompanying drawings.

As used in the claims, the term "comprises/comprising" or "contains/containing" is not intended to exclude the presence of one or more other species or steps.

As used herein, the term "inflammatory disease" refers to a disease that is caused by an inflammatory reaction in the mammalian body. Representative examples of inflammatory disease include: respiratory diseases such as asthma, chronic obstructive pulmonary disease, and rhinitis; skin diseases such as atopic dermatitis; digestive diseases such as gastritis and inflammatory enteritis; arteriosclerosis, sepsis, inflammatory joint disease, inflammatory brain disease, and the like.

As used herein, the term "treating" or "treatment" refers to reversing or alleviating inflammatory disease, metabolic disease or one or more symptoms of the disease, or inhibiting the progress thereof, unless stated otherwise. As used herein, the term "preventing" or "prevention" is intended to include reducing the likelihood of developing inflammatory disease or metabolic disease.

As used herein, the term "cytokine" refers to a secreted protein that affects the functions of other cells. Particularly, it relates to the modulation of interactions between cells of the immune system or cells involved in the inflammatory response. Examples of cytokines include, but are not necessarily limited to, interleukin 1 (IL-1), preferably interleukin IL-1β, interleukin-6 (IL-6), interleukin 8 (IL-8), and tumor necrosis factor-α (TNF-α).

As used herein, the term "suppressing appetite" refers to any action that suppresses or delays appetite by administering the strain or composition to stimulate the secretion of diet-related hormones (e.g., appetite suppressant hormones).

One aspect of the present invention is directed to a next-generation probiotic strain which is an *Akkermansia muciniphila* EB-AMDK19 strain (accession number KCTC 13761BP).

The strain has the 16s rRNA gene of SEQ ID NO: 1.

The *Akkermansia muciniphila* EB-AMDK19 strain of the present invention is a monococcus or diplococcus isolated from healthy Koreans feces, which is an elliptical cell of 0.5 to 1 μm in size. Also, it is a mucus-degrading bacterium which is anaerobic, non-motile, and gram-negative. It does not form an endospore. The *Akkermansia muciniphila* EB-AMDK19 strain is capable of producing several mucolytic enzymes, and thus may use mucus as carbon and nitrogen sources. The *Akkermansia muciniphila* EB-AMDK19 strain can metabolize various carbon sources, including galactose, N-acetylglucosamine, and lactose, and produces, as main metabolites, short-chain fatty acids such as propionic acid and acetic acid.

According to one embodiment of the present invention, the *Akkermansia muciniphila* EB-AMDK19 strain is capable of exhibiting an anti-inflammatory effect by inhibiting the expression of inflammatory cytokines, specifically IL-8, IL-6, IL-1β, and TNF-α.

Tight junctions formed between epithelial cells are particularly important for the barrier function of epithelial cells. The tight junctions are a type of cell-cell junction, and are so strong that it appears under an electron microscope that the cell membranes of two adjacent cells are fused. The barrier function is a function that blocks foreign substances from passing between epithelial cells, and is important in both blood vessels and digestive tracts. Constituent molecules that are involved in formation of the tight junctions typically include a membrane protein called occludin and cytoplasmic ZO proteins as well as proteins such as cingulin are also involved in the formation of the tight junctions. Through the interaction between these proteins, the structure and function of the tight junctions are completed. The *Akkermansia muciniphila* EB-AMDK19 strain according to one embodiment of the present invention increases the expression of the tight junction proteins ZO-1 (zonular occludens-1, $p<0.01$) and occludin and blocks inflammatory proteins from migrating into tissues, thereby promoting mucous regeneration and alleviating inflammation of colonic mucosa.

When obesity is induced, it causes abnormalities in visceral adipose tissue, excessive secretion of tumor necrosis factor, infiltration of immune cells such as macrophages into adipose tissue, and increased expression of inflammatory cytokines. This results in chronic inflammation of adipose tissue, and the chronic inflammatory response reduces insulin sensitivity and induces glucose tolerance, leading to diabetic disease. Therefore, suppression of adipose tissue hypertrophy and inflammatory response can exhibit an anti-obesity effect, and as a result, can also be useful against anti-metabolic diseases.

The novel *Akkermansia muciniphila* EB-AMDK19 strain of the present invention may inhibit body weight gain and body fat accumulation, lower insulin resistance, lower total blood cholesterol levels, reduce the level of blood glutamic pyruvic transaminase (GPT) that is a hepatotoxicity indicator, and reduce the levels of inflammatory cytokines. Thus, it may be useful for preventing or treating diabetes, obesity, insulin resistance, fatty liver, hyperlipidemia, or metabolic disease, which is associated with these factors. In particular, the metabolic disease may be a disease in which various metabolic diseases such as diabetes and obesity appear simultaneously in one person. The *Akkermansia muciniphila* EB-AMDK19 strain of the present invention has therapeutic efficacy against both inflammatory disease and metabolic disease, and thus can provide the remarkable effect of comprehensively treating various diseases that are highly correlated with inflammation or obesity.

In particular, the novel *Akkermansia muciniphila* EB-AMDK19 strain of the present invention exhibits the effect of substantially inhibiting lipid accumulation by reducing the expression of the adipocyte differentiation-related factor PPARγ and also reducing the mRNA expression of CEBPα, aP2, CD36, ACC1, LPL (lipoprotein lipase), LDLR, or FAS.

Another aspect of the present invention is directed to a pharmaceutical composition for preventing or treating inflammatory disease or metabolic disease, which contains an *Akkermansia muciniphila* EB-AMDK19 strain (accession number KCTC 13761BP), a culture thereof, or a dried product thereof.

The pharmaceutical composition of the present invention may contain a probiotic form of the *Akkermansia muciniphila* EB-AMDK19 strain or a pasteurized form of the *Akkermansia muciniphila* EB-AMDK19 strain. Pasteurization of the *Akkermansia muciniphila* EB-AMDK19 strain refers to heating at temperature equal to or higher than 50° C.; and lower than 100° C. for 10 minutes or more. For example, the strain may be pasteurized at a temperature of 70° C.; for 30 minutes. A pasteurized form of the *Akkermansia muciniphila* EB-AMDK19 strain can reduce body fat accumulation to a greater extent compared to a probiotic form of the strain.

Although the reason why the pasteurized form of the *Akkermansia muciniphila* EB-AMDK19 strain is more effective than the probiotic form has not been accurately identified, it can be presumed that when the *Akkermansia muciniphila* EB-AMDK19 strain is pasteurized, the cell wall components (such as Amuc_1100) or membrane proteins of the strain enhance metabolic benefits in a host.

The beneficial effect of the novel strain of the present invention is presumed to be related to a gene cluster (Amuc_1098-Amuc_1102) containing Amuc_1100 and to be attributed to polypeptides that interact with the signaling pathway of toll-like receptor 2 ("TLR2"), which is present on the surface of immune cells located near the barrier of intestinal mucosa and modulates intestinal homeostasis and host metabolism. For example, the Amuc-1100 polypeptide is expected to maintain the integrity of the barrier of the intestinal mucosa and interact with TLR2 present on the surface of immune cells to modulate or promote the TLR2 signaling pathway, thereby promoting the secretion of cytokines (e.g., IL-6, IL-8, and IL-10) from immune cells. Prolipoprotein diacylglyceryl transferase gene (Amuc_1104) is located in close proximity to the gene cluster (Amuc_1098-Amuc_1102). In addition, Amuc_1100 can be stably maintained under the temperature condition used during pasteurization, thus contributing to the effect of the pasteurized strain.

The pharmaceutical composition of the present invention is effective for the treatment or prevention of inflammatory diseases, particularly inflammatory bowel disease. Examples of such inflammatory bowel disease include Crohn's disease, ulcerative colitis, intestinal Behcet's disease, simple ulcer, radiation enteritis, and ischemic enteritis. In particular, the pharmaceutical composition is effective against Crohn's disease or ulcerative colitis.

The metabolic disease in the present invention is preferably obesity, insulin resistance, fatty liver, hyperlipidemia, or complications thereof, but is not necessarily limited thereto. For example, the pharmaceutical composition of the present invention is effective for preventing or treating inflammatory bowel disease (IBD), insulin resistance, or dyslipidemia, or for reducing cholesterol levels or body weight.

The pharmaceutical composition of the present invention contains, as an active ingredient, the *Akkermansia muciniphila* EB-AMDK19 strain at a concentration of $10^8$ to $10^{12}$ CFU/g of the composition, or a culture containing viable cells of the *Akkermansia muciniphila* EB-AMDK19 strain at the same concentration above.

The *Akkermansia muciniphila* EB-AMDK19 strain of the present invention may be recovered by a separation process such as centrifugation, and prepared as a probiotic by drying, for example, freeze-drying, for use.

The *Akkermansia muciniphila* EB-AMDK19 strain of the present invention is oxygen-sensitive, and hence is preferably cultured under anaerobic conditions (90% nitrogen, 5% hydrogen, and 5% carbon dioxide).

Components of the liquid medium during culture can affect the growth of the strain and the production of active ingredients. Thus, it is necessary to establish the components and their conditions of the liquid medium, which are optimal for culturing the novel *Akkermansia muciniphila* EB-AMDK19 strain of the present invention.

The liquid medium may contain, as a carbon source, one or more selected from the group consisting of glucose, lactose, galactose, mannose, 1-fucose, lactate, formate, acetate, propionate, 1,2-propenediol, butyrate, and N-acetylglucosamine, but is not limited thereto. Preferably, it may contain glucose and N-acetylglucosamine. The liquid medium may contain, as a nitrogen source, one or more selected from the group consisting of tryptone, peptone, soy peptone, L-glutamic acid, and ammonium, but is not limited thereto.

The liquid medium may contain, as trace elements, one or more selected from the group consisting of $KH_2PH_4$, $Na_2HPO_4$, NaCl, $MgCl_2$, $CaCl_2$), $FeCl_2$, $ZnCl_2$, $CuCl_2$, $MnCl_2$, $CoCl_2$, $NiCl_2$, $Na_2SeO_3$, $Na_2WO_4$ and $Na_2MoO_4$, but is not limited thereto.

The liquid medium may have a pH of 6.8 to 7.2, preferably a pH of 7.0. The pH can affect the activity of protein by changing the charge of the amino or carboxyl group of the amino acid, which is a unit of the enzymatic protein important for cell metabolism. In addition, changes in the pH in the external environment can affect the ionization of microbial nutrients, which can affect nutrient intake of the microorganism.

The liquid medium is preferably a medium containing glucose, N-acetylglucosamine, threonine, soypeptone, or any combination thereof.

The pharmaceutical composition of the present invention may further contain pharmaceutically acceptable carriers and/or excipients, in addition to the active ingredient. In addition, the composition may be formulated with various additives, such as a binder, a disintegrant, a coating agent, and a lubricant, which are commonly used in the pharmaceutical industry.

The pharmaceutical composition of the present invention may be formulated in the form of powder, granule, tablet, capsule, or liquid by mixing the *Akkermansia muciniphila* strain of the present invention with a suitable carrier, excipient, auxiliary active ingredient, etc. The pharmaceutical composition of the present invention may be formulated as a product for oral administration. In addition, the composition of the present invention may be productized by enteric coating using any known method so that it can pass through the stomach and then reach the small intestine in which the active ingredient microorganism can be rapidly released into the intestines.

Excipients that may be used in the present invention include: sugars such as sucrose, lactose, mannitol, or glucose; and starches such as corn starch potato starch, rice starch, or partially pregelatinized starch. Binders that may be used in the present invention include polysaccharides such as dextrin, sodium alginate, carrageenan, guar gum, acacia, and agar; naturally-occurring macromolecular substances such as tragacanth, gelatin, and gluten; cellulose derivatives such as hydroxypropylcellulose, methylcellulose, hydroxypropylmethylcellulose, ethyl cellulose, hydroxypropyl ethyl cellulose, and sodium carboxymethyl cellulose; and polymers such as polyvinylpyrrolidone, polyvinyl alcohol, polyvinyl acetate, polyethylene glycol, polyacrylic acid, polymethacrylic acid, and vinyl acetate resin.

Disintegrants that may be used in the present invention include: cellulose derivatives such as carboxymethylcellulose, calcium carboxymethylcellulose, low-substituted hydroxypropylcellulose, and cellulose derivatives; and starches such as sodium carboxymethyl starch, hydroxypropyl starch, corn starch, potato starch, rice starch, and partially pregelatinized starch.

Examples of lubricants that may be used in the present invention include talc, stearic acid, calcium stearate, magnesium stearate, colloidal silica, hydrous silicon dioxide, and various types of waxes and hydrogenated oils.

Coating agents that may be used in the present invention include, but are not necessarily limited to, water-insoluble copolymers such as a dimethylaminoethyl methacrylate-methacrylic acid copolymer, a polyvinylacetal diethylaminoacetate, an ethylacrylate-methacrylic acid copolymer, an ethylacrylate-methylmethacrylate-chlorotrimethylammonium ethylmethacrylate copolymer, and ethyl cellulose; enteric polymers such as a methacrylic acid-ethyl acrylate copolymer, hydroxypropyl methyl cellulose phthalate, hydroxypropyl methyl cellulose acetate succinate; and water-soluble polymers such as methyl cellulose, hydroxypropyl methyl cellulose, polyvinylpyrrolidone, and polyethylene glycol.

The dose of the strain as an active ingredient in the composition for preventing or treating inflammatory disease or metabolic disease according to the present invention may be determined in consideration of various factors, including the type of disease, the patient's age, body weight, sex and medical condition, the severity of the condition, and the route of administration. Thus, the dose regime can vary widely, but can be routinely determined using standard methods. For an adult patient, generally $1\times10^6$ or more viable cells or pasteurized cells, preferably $1\times10^8$ to $1\times10^{12}$ viable cells or pasteurized cells may be may be administered once or several times as needed. The exact formulation, route of administration, and dosage of the pharmaceutical composition disclosed herein can be selected by an individual physician by taking into account the patient's condition.

Still another aspect of the present invention is directed to a pharmaceutical composition for suppressing appetite, which contains an *Akkermansia muciniphila* EB-AMDK19 strain (accession number KCTC 13761BP), a culture thereof, or a dried product thereof.

Glucagon-like peptide-1 (GLP-1) and peptide YY (PYY) are appetite suppressant hormones that are accompanied by decreased food intake (Wren and Bloom, Gastroenterology 132:2116-2130 (2007)). According to one embodiment of the present invention, the *Akkermansia muciniphila* EB-AMDK19 strain can suppress appetite by increasing the expression and secretion of the appetite suppressant hormones GLP-1 (glucagon like peptide 1) and PYY (peptide YY).

Still another aspect of the present invention is directed to a food for preventing or ameliorating inflammatory disease or metabolic disease, which contains an *Akkermansia muciniphila* EB-AMDK19 strain (accession number KCTC 13761BP), a culture thereof, or a dried product thereof. A food containing the *Akkermansia muciniphila* EB-AMDK19 strain of the present invention may be taken as a food or nutritional product, such as milk or dairy products, or as a food supplement or health functional food. In one embodiment of the present invention, examples of the food product include, but are not necessarily to, foods such as dairy products, beverages, juices, soups, or foods for children.

The present invention will be described in more detail below with reference to examples. However, these examples are merely to illustrate the present invention, and the scope of the present invention is not limited to these examples.

EXAMPLES

Example 1: Isolation and Identification of *Akkermansia muciniphila* Strain

1.1. Isolation and Identification of Strain

In order to isolate *Akkermansia muciniphila* from the feces of a healthy Korean (female, 35 years old, BMI: 23.3), according to the method of Derrien, selective culture was performed using mucin medium (0.4 g/L monopotassium phosphate, 0.53 g/L sodium dichlorophosphate, 0.3 g/L sodium chloride, 0.3 g/L aluminum chloride, 0.1 g/L magnesium chloride, 0.11 g/L calcium chloride, 4.0 g/L sodium bicarbonate, 1 mL acidic trace element solution, 1 mL alkaline trace element solution, 1 mL vitamin solution, 2.5 g/L porcine gastric fluid (Type III)), and 0.25 g/L sodium sulfide nonahydrate), and then a strain was isolated (Derrien et al., 2004).

Figure 2:
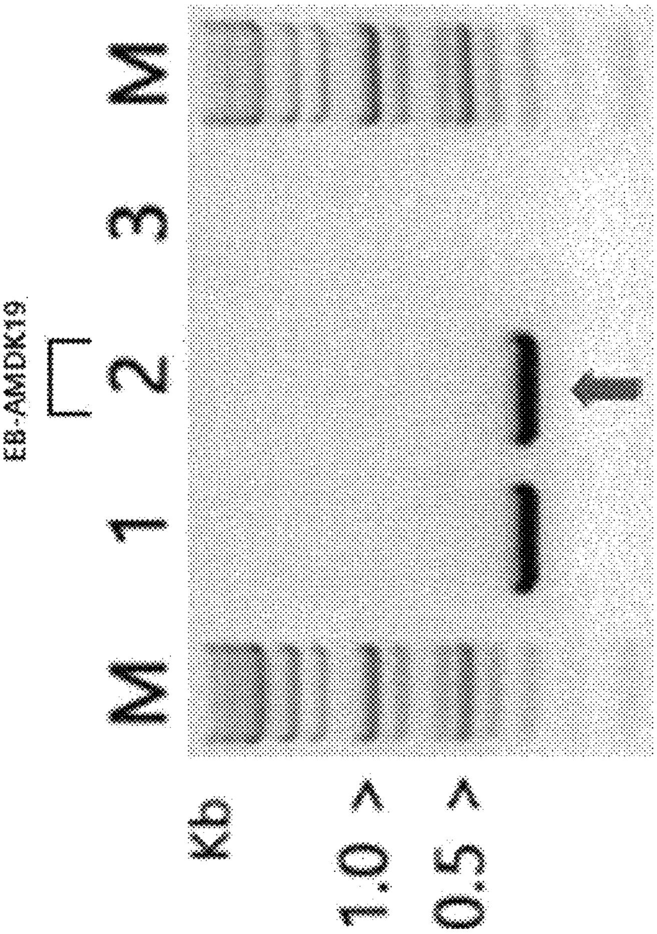
FIG. 2 shows the results of PCR analysis of the *Akkermansia muciniphila* EB-AMDK19 strain of the present invention and the *Akkermansia muciniphila* ATCC BAP-835 strain.

In order to confirm that the isolated strain would be an *Akkermansia muciniphila* strain, the isolated strain was observed under a microscope, and the results are shown in FIG. 1. In addition, PCR analysis was performed using the AM-specific primers shown in Table 1 below, and the results of the analysis are shown in FIG. 2.

In FIG. 1, A shows an *Akkermansia muciniphila* ATCC BAA-835 strain, and B is a 1,000× magnification micrograph of an *Akkermansia muciniphila* EB-AMDK19 strain. In FIG. 2, M represents a DNA size marker, lane 1 represents a positive control (ATCC BAA-835), lane 2 represents the *Akkermansia muciniphila* EB-AMDK19 strain, and lane 3 represents a negative control (distilled water).

TABLE 1

| Designation | Direction | Sequence (5'→3') | Amplicon size |
|---|---|---|---|
| AM1 | Forward | CAG CAC GTG AAG GTG GGG AC (SEQ ID NO: 57) | 327 bp |
| AM2 | Reverse | CCT TGC GGT TGG CTT CAG AT (SEQ ID NO: 58) | |

1.2. Analysis of Utilization of Carbohydrates by Isolated *Akkermansia muciniphila* Strain In order to examine the utilization of carbohydrates by the isolated *Akkermansia muciniphila* strain of the present invention, the strain was cultured using an API® CH 50 kit (Biomerieux, France), and then whether the strain would grow using each carbohydrate was compared with the type strain (ATCC BAA-835). The results of the comparison are shown in Table 2 below.

TABLE 2

| No. | Carbohydrates | ATCC BAA-835 | EB-AMDK19 |
|---|---|---|---|
| 0 | Negative control | − | − |
| 1 | Glycerol | − | − |
| 2 | Erythritol | − | − |
| 3 | D-Arabinose | w | w |
| 4 | L-Arabinose | w | w |
| 5 | Ribose | + | w |
| 6 | D-Xylose | w | w |
| 7 | L-Xylose | w | w |
| 8 | Adonitol | − | − |
| 9 | α-Methyl-xyloside | − | − |
| 10 | D-Galactose | w | w |
| 11 | D-Glucose + Mucin | + | + |
| 12 | D-Fructose | w | − |
| 13 | D-Mannose | + | w |
| 14 | L-Sorbose | − | − |
| 15 | L-Rhamnose | − | − |
| 16 | Dulcitol | − | − |
| 17 | Inositol | − | − |
| 18 | D-Mannitol | − | − |
| 19 | D-Sorbitol | − | − |
| 20 | Methyl-α D-mannopyranoside | − | − |
| 21 | Methyl-α D-glucopyranoside | − | − |
| 22 | N-Acetylglucosamine | + | + |
| 23 | Amygdaline | − | − |
| 24 | Arbutine | − | − |
| 25 | Esculine | − | − |
| 26 | Salicine | − | − |
| 27 | D-Cellobiose | − | − |

TABLE 2-continued

| No. | Carbohydrates | ATCC BAA-835 | EB-AMDK19 |
|---|---|---|---|
| 28 | D-Maltose | − | − |
| 29 | D-Lactose (bovine origin) | + | + |
| 30 | D-Melibiose | − | − |
| 31 | D-Saccharose (sucrose) | − | − |
| 32 | D-Trehalose | − | − |
| 33 | Inuline | − | − |
| 34 | D-Melezitose | − | − |
| 35 | D-Raffinose | − | − |
| 36 | Amidon (starch) | − | − |
| 37 | Glycogene | − | − |
| 38 | Xylitol | − | − |
| 39 | Gentiobiose | − | − |
| 40 | D-Turanose | − | − |
| 41 | D-Lyxose | w | w |
| 42 | D-Tagatose | − | − |
| 43 | D-Fucose | − | − |
| 44 | L-Fucose | + | + |
| 45 | D-Arabitol | − | − |
| 46 | L-Arabitol | − | − |
| 47 | Potassium Gluconate | − | − |
| 48 | Potassium 2-Ketogluconate | − | − |
| 49 | Potassium 5-Ketogluconate Ketogluconate | w | w |

+: growth,
w: weak growth,
−: no growth,

As can be seen in Table 2 above, it was confirmed that the *Akkermansia muciniphila* EB-AMDK19 strain of the present invention differed from the type strain (ATCC BAA-835) with respect to the utilization of ribose, D-galactose, D-fructose, and D-mannose.

1.3. Whole Genome Sequencing

In order to analyze variations between the *Akkermansia muciniphila* EB-AMDK19 strain isolated as described above and the *Akkermansia muciniphila* ATCC BAA-835 at the genomic level, whole genome sequencing of the strain was performed using the PacBio technique and compared with that of the type strain (see Tables 3 and 4 below).

TABLE 3

| Genomic statistics | Strains | |
|---|---|---|
| | ATCC BAA-835 | EB-AMDK19 |
| Accession No. | CP001071 | CP025834 |
| Assembly level | Complete | Complete |
| Seq. category | Chromosome | Chromosome |
| Total size (Mb) | 2.6641 | 2.7242 |
| GC (%) | 55.8 | 55.3 |
| Protein | 2,246 | 2,140 |
| Gene | 2,321 | 2,357 |
| CDS | 2,257 | 2,293 |
| Coding | 2,246 | 2,250 |
| rRNA | 9 | 9 |
| tRNA | 52 | 52 |
| Other RNA | 3 | 3 |
| Pseudogene | 11 | 44 |
| Symmetrical identity (%) | — | 90.1368 |

*Symmetrical identity is relative to ATCC BAA-835

TABLE 4

| Genes | | Strains | |
|---|---|---|---|
| | | ATCC BAA-835 | EB-AMDK19 |
| Amuc_1098 | Sequence length | 901 | 900 |
| | Align identity (%) | 100 | 99.3 |
| | Mismatch No. | 0 | 5 |
| | Insertion No. | 0 | 0 |
| | Deletion No. | 0 | 1 |
| Amuc_1099 | Sequence length | 337 | 337 |
| | Align identity (%) | 100 | 100 |
| | Mismatch No. | 0 | 0 |
| | Insertion No. | 0 | 0 |
| | Deletion No. | 0 | 0 |
| Amuc_1100 | Sequence length | 316 | 316 |
| | Align identity (%) | 100 | 99.4 |
| | Mismatch No. | 0 | 2 |
| | Insertion No. | 0 | 0 |
| | Deletion No. | 0 | 0 |
| Amuc_1101 | Sequence length | 612 | 612 |
| | Align identity (%) | 100 | 99.2 |
| | Mismatch No. | 0 | 5 |
| | Insertion No. | 0 | 0 |
| | Deletion No. | 0 | 0 |
| Amuc_1102 | Sequence length | 237 | 237 |
| | Align identity (%) | 100 | 98.7 |
| | Mismatch No. | 0 | 3 |
| | Insertion No. | 0 | 0 |
| | Deletion No. | 0 | 0 |
| Gene_cluster | Sequence length | 2403 | 2402 |
| | Align identity (%) | 100 | 99.3 |
| | Mismatch No. | 0 | 15 |
| | Insertion No. | 0 | 0 |
| | Deletion No. | 0 | 1 |

*Gene_cluster corresponds to the length of five genes

As can be seen in Table 3 above, the whole genome statistics of the *Akkermansia muciniphila* EB-AMDK19 strain of the present invention differed from those of the *Akkermansia muciniphila* ATCC BAA-835 strain.

It is known that the Amuc_1100 is associated with therapeutic activity against anti-inflammatory or metabolic disease and is a heat-stable protein acting on the Toll-like receptor (TLR) 2 (Plovier et al., 2017). As shown in Table 4 above, the *Akkermansia muciniphila* EB-AMDK19 strain of the present invention somewhat differed from the *Akkermansia muciniphila* ATCC BAA-835 strain with respect to the Amuc_1100 related gene.

1.4. Analysis of Antimicrobial Susceptibility of Isolated Strain

In order to examine the antimicrobial susceptibility of the *Akkermansia muciniphila* EB-AMDK19 strain isolated as described above, the minimum inhibitory concentrations (MICs) of antibiotics for anaerobic bacteria (Piperacillin-Tazobactam (PTZ), Ceftizoxime (CTZ), Chloramphenicol (CML), Clindamycin (CLI), Meropenem (MEM), Moxifloxacin (MXF), Metronidazole (MTZ), and Ciprofloxacin (CIP)) against the isolated strain were determined by broth microdilution according to the guideline of Clinical & Laboratory Standard Institute (CLSI, 2017), and the results are shown in Table 5 below.

TABLE 5

| Antibiotics | MIC[a] Breakpoints (μg/mL) | | | QC ATCC 29741[b] |
|---|---|---|---|---|
| | S | I | R | |
| PTZ | ≤32/4 | 64/4 | ≥128/4 | 8/4 |
| CTZ | ≤32 | 64 | ≥128 | 16 |
| CHL | ≤8 | 16 | ≥32 | 8 |

TABLE 5-continued

| | | | | |
|---|---|---|---|---|
| CLI | ≤2 | 4 | ≥8 | 4 |
| MEM | ≤4 | 8 | ≥16 | 0.5 |
| MXF | ≤2 | 4 | ≥8 | 8 |
| MTZ | ≤8 | 16 | ≥32 | 2 |
| CIP | ≤1 | 2 | ≥4 | >32 |

| Antibiotics | Test strains ATCC BAA-835 | EB-AMDK19 |
|---|---|---|
| PTZ | ≤0.5/4 (S) | ≤0.5/4 (S) |
| CTZ | 2 (S) | 1 (S) |
| CHL | 4 (S) | 4 (S) |
| CLI | ≤0.125 (S) | 4 (I) |
| MEM | 1 (S) | 0.5 (S) |
| MXF | >32 (R) | >32 (R) |
| MTZ | ≤0.25 (S) | 0.5 (S) |
| CIP | >32 (R) | 32 (R) |

PTZ: Piperacillin-tazobactam,
CTZ: ceftizoxime (3rd gen),
CHL: chloramphenicol,
CLI: clindamycin,
MEM: meropenem,
MXF: moxifloxacin (4th gen),
MTZ: metronidazole,
CIP: ciprofloxacin (2nd gen),
[a]MIC: minimal inhibitory concentration,
[b]*Bacteroides thetiotaomicron* ATCC 29741

As can be seen in Table 5 above, the *Akkermansia muciniphila* EB-AMDK19 strain of the present invention showed moderate resistance to clindamycin, exhibited resistance to moxifloxacin and ciprofloxacin, which were fluoroquinolone based antibiotics, and showed susceptibility to all the antibiotics except for moxifloxacin and ciprofloxacin. Compared to the type strain, there was some difference in the antimicrobial resistance pattern. Therefore, it can be confirmed that the *Akkermansia muciniphila* strain according to the present invention is a safe strain that is not resistant to most antibiotics.

1.5. Analysis of Hemolytic Activity of Isolated Strain

In order to verify the safety of the *Akkermansia muciniphila* EB-AMDK19 strain isolated as described above, whether the strain would have hemolytic activity was evaluated. To this end, the strain was cultured using a blood agar medium prepared by adding 5% w/v defibrinated sheep blood to tryptic soy agar (17.0 g/L pancreatic digest of casein, 3.0 g/L pancreatic digest of soybean, 2.5 g/L dextrose, 5.0 g/L sodium chloride, 2.5 g/L potassium phosphate, and 15 g/L agar). The results of the culture are shown in FIG. 3.

Figure 3:
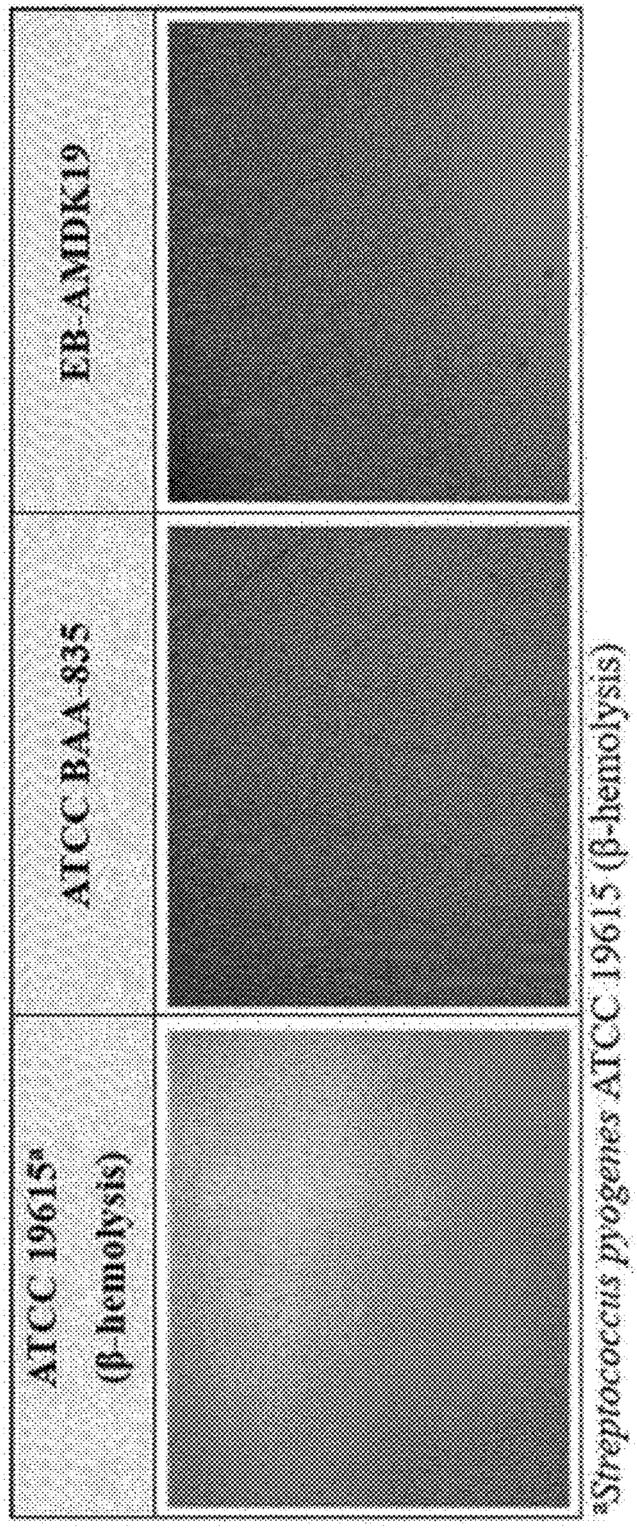
FIG. 3 shows the results of testing the hemolytic activities of the *Akkermansia muciniphila* EB-AMDK19 strain of the present invention and the *Akkermansia muciniphila* ATCC BAA-835 strain.

As can be seen through FIG. 3, β-hemolysis (a fully transparent part around a colony) associated with pathogenicity was not observed in the *Akkermansia muciniphila* EB-AMDK19 strain of the present invention.

1.6. Random Amplified Polymorphic DNA (RAPD) Analysis

In order to verify whether the *Akkermansia muciniphila* EB-AMDK19 strain isolated as described above is the same as the type strain of the same kind as previously reported, random amplified polymorphic DNA (RAPD) printing, which is a kind of molecular typing, was performed. To this end, the genomic DNA extracted from the strain was amplified using the general-purpose primers shown in Table 6 and electrophoresed on 1% agarose gel for 1 hour and 30 minutes, and DNA fragmentation patterns were compared on a UV perforator. The results of the analysis are shown in FIG. 4.

TABLE 6

| Designation | Direction | Sequence (5'→3') | SEQ ID NO |
|---|---|---|---|
| ERIC-1 | Forward | ATG TAA GCT CCT GGG GAT TCA C | SEQ ID NO: 2 |
| ERIC-2 | Reverse | AAG TAA GTG ACT GGG GTG AGC G | SEQ ID NO: 3 |
| $(GTG)_5$ | Forward/ Reverse | GTG GTG GTG GTG GTG | SEQ ID NO: 4 |

Figure 4:
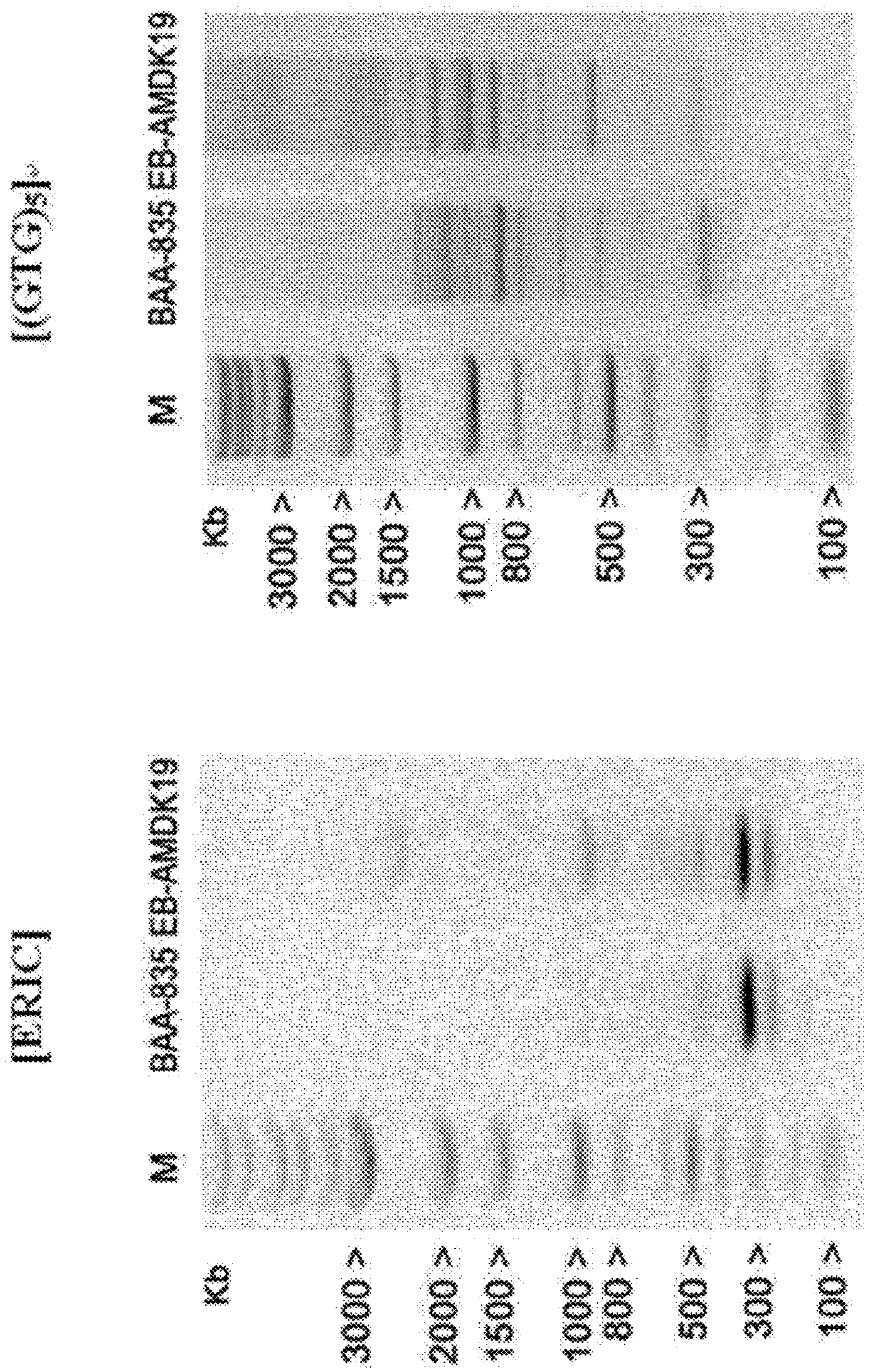
FIG. 4 shows the results of RAPD (Random Amplified Polymorphic DNA) analysis of the *Akkermansia muciniphila* EB-AMDK19 strain of the present invention and the *Akkermansia muciniphila* ATCC BAA-835 strain.

As can be seen in FIG. 4, the *Akkermansia muciniphila* EB-AMDK19 strain of the present invention was compared with the *Akkermansia muciniphila* type strain (ATCC BAA-835), it showed a different band pattern. It is known that the RAPD band patterns of *Akkermansia muciniphila* species are different from each other when the species are different. Thus, it was confirmed that the *Akkermansia muciniphila* strain isolated in the present invention was different from the type strain (ATCC BAA-835).

1.7. Phylogenetic Tree Analysis Using Full-Length 16S rRNA Gene Sequence

In order to analyze the full-length 16S rRNA gene sequencing of the *Akkermansia muciniphila* strain isolated as described above, the 16S rRNA gene was amplified using the 27F and 1541R primers shown in Table 7 below, and then sequenced using a 3730×1 DNA analyzer. A phylogenetic tree was prepared using the 16S rRNA gene sequences of the EB-AMDK19 strain obtained as described above and other strains of the same species already published. The prepared phylogenetic tree is shown in FIG. 5.

TABLE 7

| Designation | Direction | Sequence (5'→3') | Amplicon size |
|---|---|---|---|
| 27F | Forward | AGA GTT TGA TCM TGG CTC AG (SEQ ID NO: 5) | 1,505 bp |
| 1541R | Reverse | AAG GAG GTG ATC CAG CCG CA (SEQ ID NO: 6) | |

Figure 5:
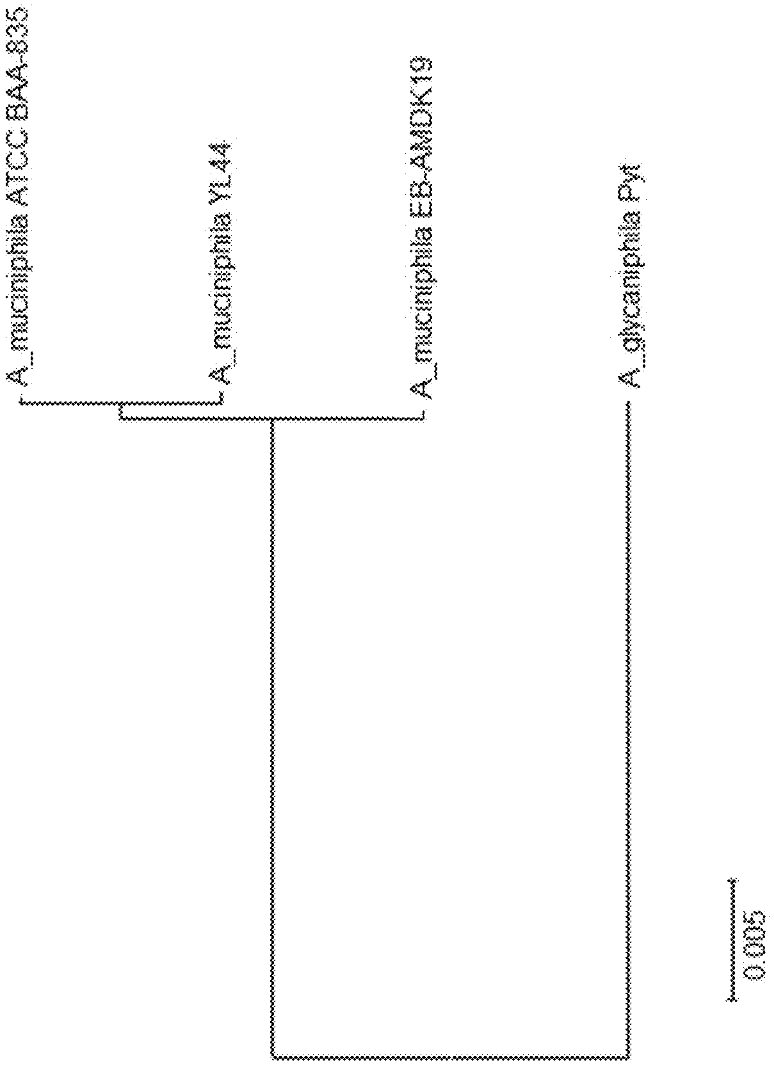
FIG. 5 shows the phylogenetic relationship between the *Akkermansia muciniphila* EB-AMDK19 strain of the present invention and other *Akkermansia muciniphila* strains.
Figure 6A:
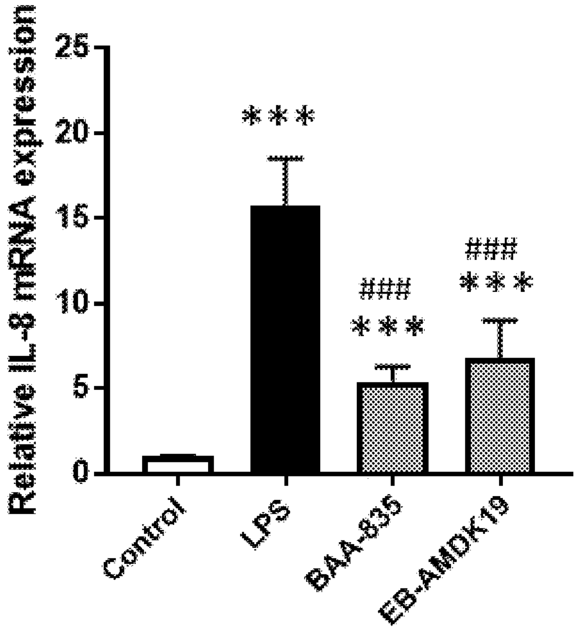
FIGS. 6A-6D are graphs showing the relative mRNA expression levels of the cytokines IL-6, IL-8, IL-1β and TNF-α, which demonstrate the anti-inflammatory effect of the *Akkermansia muciniphila* EB-AMDK19 strain of the present invention.
Figure 6B:
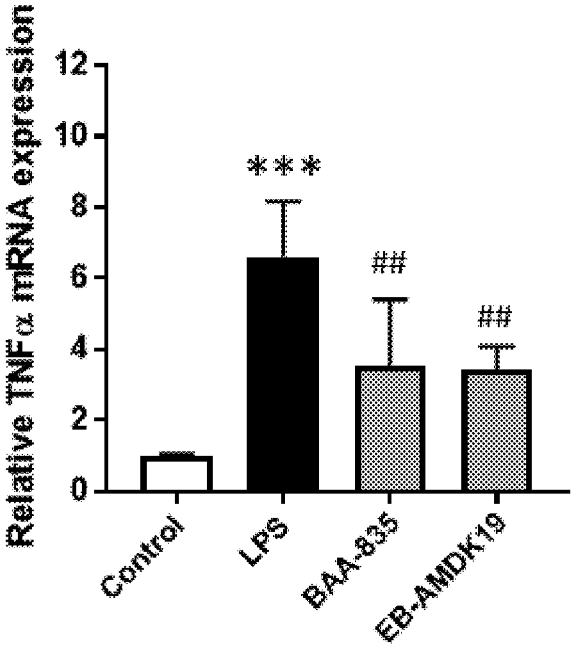
Figure 6C:
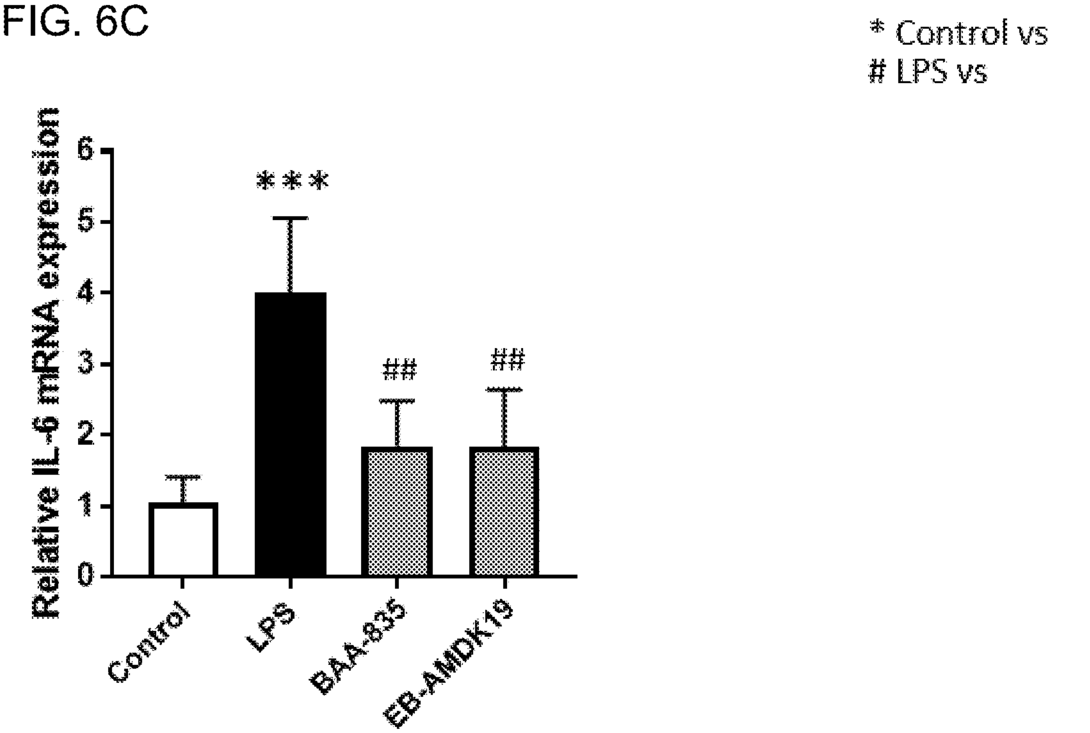
Figure 6D:
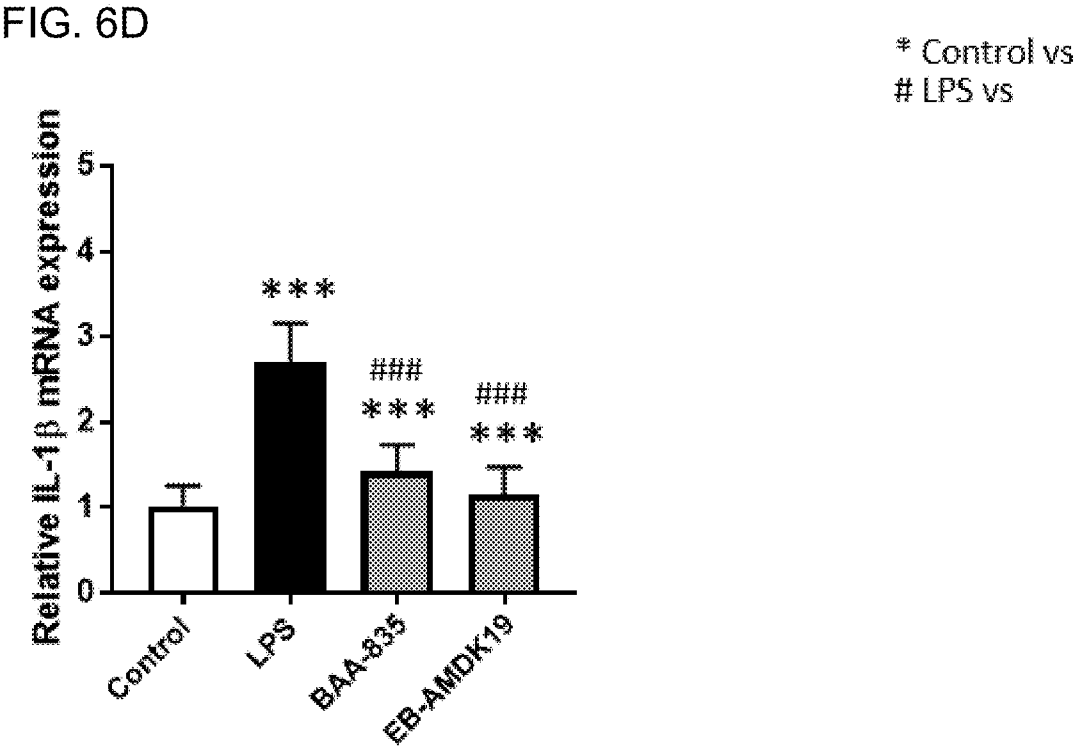

As shown in FIG. 5, the evolutionary relationship between the 16s rRNA gene sequences was analyzed through the phylogenetic tree, and as a result, it was confirmed that the *Akkermansia muciniphila* EB-AMDK19 strain was a strain that genetically belonged to *Akkermansia muciniphila* species (see FIG. 5).

The *Akkermansia muciniphila* EB-AMDK19 strain isolated from human feces was identified through the biochemical method (API®) and molecular biological methods (16s rRNA sequencing, RAPD, and full-length screening) using the *Akkermansia muciniphila* type strain (ATCC BAA-835) as a control. In addition, through the antibiotic resistance test, the isolated *Akkermansia muciniphila* EB-AMDK19 strain was to be a safe strain that can function as probiotics. Based on these results, the isolated *Akkermansia muciniphila* strain was named *Akkermansia muciniphila* EB-AMDK19 strain and deposited with the Korean Collection for Type Cultures (KCTC), the Korea Research Institute of Bioscience and Biotechnology, under accession number KCTC 12398BP.

Furthermore, it was finally confirmed to be a strain belonging to *A. muciniphila* species through 16s rRNA gene sequencing, and was named "*Akkermansia muciniphila* EB-AMDK19".

Example 2: Evaluation of Anti-Inflammatory Effect of *Akkermansia muciniphila* Strain (*A. muciniphila*)

2.1. Production of Pasteurized Cells for Evaluation of Anti-Inflammatory Effect

A culture of the *Akkermansia muciniphila* EB-AMDK19 strain was centrifuged at 12,000×g and 4° C. for 5 minutes, and the cells harvested, suspended in PBS, and adjusted to an OD value of 0.25±0.03 (8 log CFU/mL). Next, the cells were pasteurized at 70° C. for 30 minutes and stored in a cryogenic freezer until use.

2.2. Evaluation of Anti-Inflammatory Effect in HT-29 Intestinal Epithelial Cells Since cytokines and other immunomodulators were involved in the regulation of the inflammatory response in inflammatory bowel disease, the present inventors investigated whether the expression of these genes would be affected by administration of the strain of the present invention. For an in vitro test for evaluation of anti-inflammatory efficacy, human colonic epithelial HT-29 cells (ATCC® HTB-38™, USA) were cultured. The cells were cultured in an incubator (NUAIRE, USA) at 37° C. under 5% $CO_2$ using, as basal culture medium, McCoy's 5A modified medium (Gibco, USA) supplemented with 10% FBS (fetal bovine serum, Hyclone, USA) and 10 μg/ml gentamicin. In order to examine whether the *Akkermansia muciniphila* EB-AMDK19 strain would inhibit LPS-induced expression of the pro-inflammatory cytokines IL-8, TNF-α, IL-6 and IL-1β genes in HT-29 cells, real-time PCR was performed using the primers shown in Table 8 below.

Total RNA was extracted using TRI reagent (Sigma, USA), and for cDNA synthesis, 1 μg of the RNA was synthesized into cDNA using an M-MLV cDNA synthesis kit (Enzynomics, Korea). Real-time PCR was performed using a Quant Studio 3 real time PCR system (Applied Biosystems, USA).

The expression of inflammatory cytokines was analyzed using SYBR Green TOPreal™ qPCR 2× PreMIX (Enzynomics, Korea), and GAPDH was used as an internal standard. PCR was performed under the following conditions: pre-incubation (for UDG) of 4 min at 50° C., 10 min at 95° C., and 40 cycles, each consisting of 15 sec at 95° C. and 1 min at 60° C. Data were analyzed by delta CT method using the program built in QuantStudio Design & Analysis Software v1.4.3, and the results are shown in FIGS. 6A-6D.

The results obtained by all the experiments in this Example were calculated as the mean and standard deviation of each group using the statistical program GraphPad Prism 7 (GraphPad software Inc., USA). The difference between the groups was analyzed using one-way ANOVA and Tukey's test, and a p value of 0.05 or less was considered statistically significant. AUC (area under curve) was calculated from some results. From some data, AUC (area under curve) was calculated.

TABLE 8

| Targets | Primer sequences | SEQ ID NOs. |
|---|---|---|
| GAPDH | F: 5'-GAC ATC AAG AAG GTG GTG AAG CAG-3' | SEQ ID NO: 7 |
| | R: 5'-ATA CCA GGA AAT GAG CTT GAC AAA-3' | SEQ ID NO: 8 |

TABLE 8-continued

| Targets | Primer sequences | SEQ ID NOs. |
|---|---|---|
| IL-8 | F: 5'-TTT TGC CAA GGA GTG CTA AAG A-3' | SEQ ID NO: 9 |
| | R: 5'-AAC CCT CTG CAC CCA GTT TTC -3' | SEQ ID NO: 10 |
| TNF-α | F: 5'-AGC CCA TGT TGT AGC AAA CC-3' | SEQ ID NO: 11 |
| | R: 5'-TGA GGT ACA GGC CCT CTG AT-3' | SEQ ID NO: 12 |
| IL-6 | F: 5'-AAA GAG GCA CTG GCA GAA AA-3' | SEQ ID NO: 13 |
| | R: 5'-TTT CAC CAG GCA AGT CTC CT-3' | SEQ ID NO: 14 |
| IL-1β | F: 5'-CCG ACC ACC ACT ACA GCA AG-3' | SEQ ID NO: 15 |
| | R: 5'-GGG CAG GGA ACC AGC ATC TT-3' | SEQ ID NO: 16 |

Referring to FIGS. 6A-6D, when LPS (100 μg/ml) was treated with HT-29 cells alone for 6 hours, the expression of IL-8, TNF-α, IL-6 and IL-1β increased compared to the normal group (p<0.001). In contrast, compared to the group treated with the LPS, the group treated with the LPS and the *Akkermansia muciniphila* BAA-835 strain or *Akkermansia muciniphila* EB-AMDK19 dead cells (10%, v/v) showed that the expression of IL-8 (P<0.001), TNF-α (P<0.01), IL-6 (P<0.01), and IL-1β (P<0.001) was significantly reduced.

It was shown that the novel strain of the present invention decreased the mRNA expression of pro-inflammatory cytokines (such as IL-8, TNF-α, IL-6 and IL-113) in vitro. Therefore, this demonstrates that the strain of the present invention can be effective for the treatment of inflammatory disease.

Example 3: Evaluation of Lipid Accumulation Inhibitory Effect of *Akkermansia muciniphila* Strain Whether the expression of biomarkers associated with lipid accumulation and obesity would be influenced by administration of the strain of the present invention was examined.

3.1. Oil Red-O Staining of Cells

In order to evaluate the effect of the *Akkermansia muciniphila* EB-AMDK19 strain of the present invention on adipose differentiation and adipose production in 3T3-L1 cells, Oil Red-O staining was performed (Jeon T. et al., Red yeast rice extracts suppress adipogenesis by down-regulating adipogenic transcription factors and gene expression in 3T3-L1, Life Sci., 12; 75(26), pp. 3195-3203, 2004).

Oil Red-O staining is a method of measuring lipid accumulation in differentiated 3T3-L1 cells by staining the cells with Oil Red-O reagent. Mouse preadipocyte 3T3-L1 cells (Korean Cell Line Bank, KOREA) were cultured in an incubator (NUAIRE, USA) at 37° C. under 5% $CO_2$ using, as basal culture medium, Dulbecco's Modified Eagle's Medium (DMEM) supplemented with 10% FBS (fetal bovine serum, Hyclone, USA) and 1% penicillin/streptomycin. Adipose differentiation of the preadipocyte 3T3-L1 cells was induced by treatment with insulin (1 μg/ml), IBMX (0.5 mM) and dexamethasone (1 μM) for 10 days, and the cells were treated with the *Akkermansia muciniphila* EB-AMDK19 strain. Then, the culture was washed three times with PBS to remove the medium. 10% formalin (Sigma, USA) was added and Oil red 0 (Sigma, USA) solution was allowed to react with the cells for 1 hour, followed by washing with distilled water, thereby staining the lipid droplets.

Figure 7A:
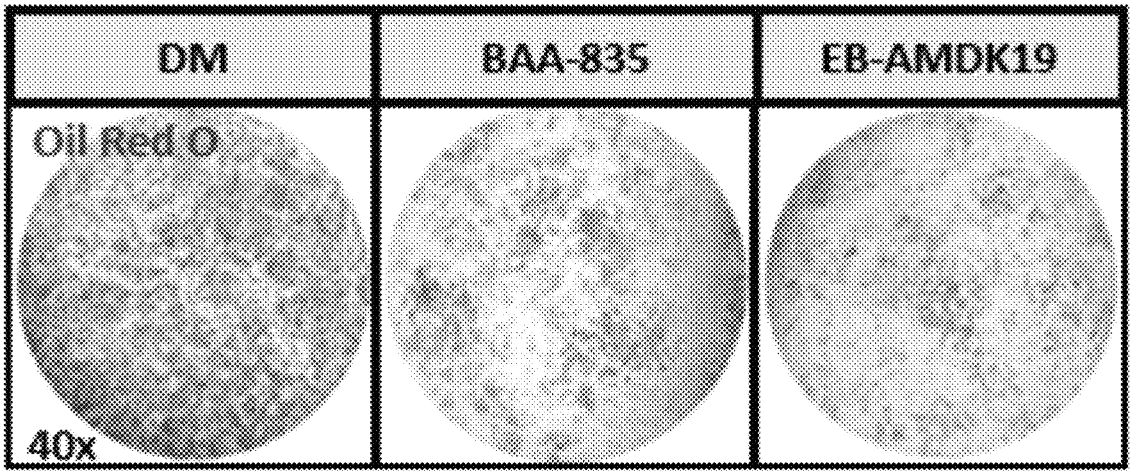
FIGS. 7A and 7B are photographs and a graph, which show the degree of lipid accumulation in 3T3-L1 cells after treatment with the *Akkermansia muciniphila* EB-AMDK19 strain of the present invention.

After the completion of cell staining, the cells were washed three times with 40% isopropanol (Duksan, KOREA), and then dried. The size of lipid droplets in the cells was observed under an optical microscope, and the results are shown in FIG. 7A. The lipid droplet sample stained with the Oil red O solution was lysed with isopropanol, and the absorbance at 500 nm was measured using a spectrophotometer (Epoch, BioTek, USA). The results of the measurement are shown in FIG. 7B.

Figure 7B:
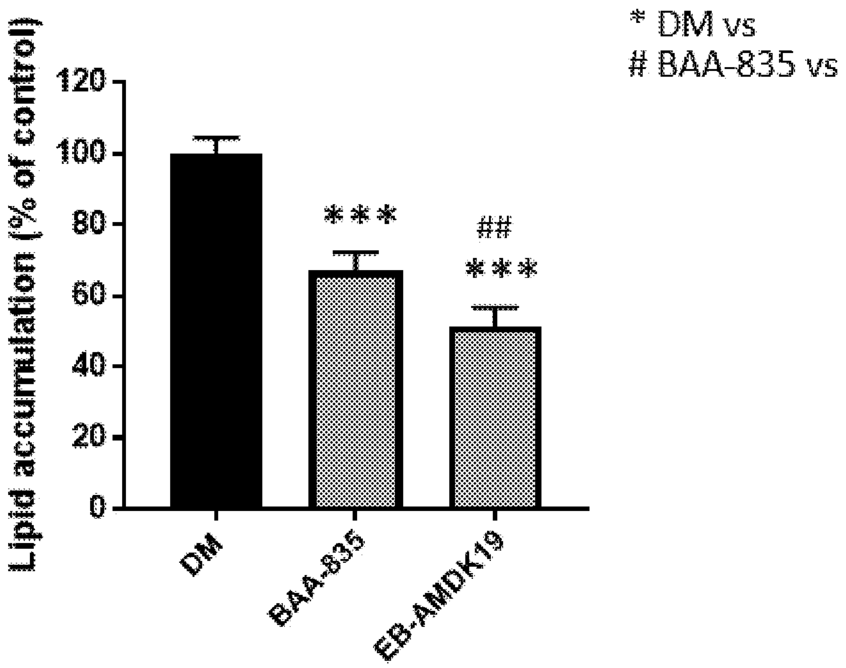

As a result, as shown in FIG. 7B, it was confirmed that when the 3T3-L1 cells were treated with the *Akkermansia muciniphila* EB-AMDK19 strain of the present invention during the differentiation of the cells, adipose accumulation in the treated cells was significantly inhibited compared to that in the control group.

3.2. Evaluation of Effect Against Biomarker Gene Expression

In order to evaluate the effect of the strain of the present invention on the inhibition of adipocyte differentiation, the mRNA expression of the following genes was analyzed by performing real-time PCR using the gene-specific primers shown in Table 9 below: PPARγ (peroxisome proliferator-activated receptor gamma), CEBPα (CCAAT/enhancer binding protein alpha), adipocyte protein 2 (aP2), CD36 (cluster differentiating 36), FAS (fatty acid synthase), ACC1 (acetyl-coenzyme A-carboxylase), LPL (lipoprotein lipase), and LDLR (low-density lipoprotein receptor).

Specifically, total RNA was extracted from cell monolayers using TRI reagent (Sigma, USA) according to the manufacturer's instruction, and cDNA was synthesized from 1 μg of the total RNA using an M-MLV cDNA synthesis kit (Enzynomics, Korea). PCR reaction was performed using the Quant Studio 3 real time PCR system (Applied Biosystems, USA) under the following conditions: pre-incubation (for UDG) of 4 min at 50° C., 10 min at 95° C., and 40 cycles, each consisting of 15 sec at 95° C. and 1 min at 60° C. Data were analyzed by delta CT using the program built in QuantStudio Design & Analysis Software v1.4.3.

TABLE 9

| Targets | Primer sequences | SEQ ID NOs. |
|---|---|---|
| GAPDH | F: 5'-GAC ATC AAG AAG GTG GTG AAG CAG-3' | SEQ ID NO: 17 |
| | R: 5'-ATA CCA GGA AAT GAG CTT GAC AAA-3' | SEQ ID NO: 18 |
| PPARγ | F: 5'-CAA GAA TAC CAA AGT GCG ATC AA-3' | SEQ ID NO: 19 |
| | R: 5'-GAG CTG GGT CTT TTC AGA ATA ATA AG-3' | SEQ ID NO: 20 |

TABLE 9-continued

| Targets | Primer sequences | SEQ ID NOs. |
|---|---|---|
| CEBPα | F: 5'-AGC AAC GAG TAC CGG GTA CG-3' | SEQ ID NO: 21 |
| | R: 5'-TGT TTG GCT TTA TCT CGG CTC-3' | SEQ ID NO: 22 |
| aP2 | F: 5'-AGT GAA AAC TTC GAT GAT TAC ATG AA-3' | SEQ ID NO: 23 |
| | R: 5'-GCC TGC CAC TTT CCT TGT G-3' | SEQ ID NO: 24 |
| CD36 | F: 5'-TTG TAC CTA TAC TGT GGC TAA ATG AGA-3' | SEQ ID NO: 25 |
| | R: 5'-CTT GTG TTT TGA ACA TTT CTG CTT-3' | SEQ ID NO: 26 |
| FAS | F: 5'-AGG GGT CGA CCT GGT CCT CA-3' | SEQ ID NO: 27 |
| | R: 5'-GCC ATG CCC AGA GGG TGG TT-3' | SEQ ID NO: 28 |
| ACC1 | F: 5'-CCT CCG TCA GCT CAG ATA CA-3' | SEQ ID NO: 29 |
| | R: 5'-TTT ACT AGG TGC AAG CCA GAC A-3' | SEQ ID NO: 30 |
| LPL | F: 5'-TTG CCC TAA GGA CCC CTG AA-3' | SEQ ID NO: 31 |
| | R: 5'-ACA GAG TCT GCT AAT CCA GGA AT-3' | SEQ ID NO: 32 |
| LDLR | F: 5'-TGA CTC AGA CGA ACA AGG CTG-3' | SEQ ID NO: 33 |
| | R: 5'-ATC TAG GCA ATC TCG GTC TCC-3' | SEQ ID NO: 34 |

Referring to FIGS. 8A-8H, when the differentiation of 3T3-L1 cells to adipocytes was induced by treatment with adipocyte differentiation medium (DM), the degree of lipid accumulation in micrographs of the lipid droplets and in the cells significantly decreased in the group treated with DM+the *Akkermansia muciniphila* BAA-835 strain or DM+the pasteurized *Akkermansia muciniphila* EB-AMDK19 dead cells (10% v/v) compared to that in the control group ($p<0.001$), and it also significantly decreased in the group treated with the EB-AMDK19 dead cells compared to that in the positive control group (ATCC BAA-835) ($P<0.01$).

In general, the expression of PPARγ (Peroxisome proliferator-activated receptor γ), CEBPα (CCAAT/enhancer binding protein α), aP2α (activator protein 2 alpha), CD36, ACC1, LPL, LDLR, and FAS (fatty acid synthase) increases in the stage of differentiation to adipocytes.

In addition, as shown in FIGS. 8A-8H, when increased expression of PPARγ, CEBPα, aP2, CD36, ACC1, LPL, LDLR and FAS, which are genes involved in adipocyte differentiation, was calculated relative to 100% after the induction of adipocyte differentiation, it could be seen that the expression of PPARγ (p<0.001), CEBPα (p<0.001), aP2 (p<0.001), CD36 (p<0.001), ACC1 (p<0.01), LPL (p<0.001), LDLR (p<0.05), FAS (p<0.001) significantly decreased in the group treated with DM+the *Akkermansia muciniphila* BAA-835 strain, and the expression of PPARγ (p<0.001), CEBPα (p<0.001), aP2 (p<0.001), CD36 (p<0.001), ACC1 (p<0.001), LPL (p<0.001), LDLR (p<0.01) and FAS (p<0.001) significantly decreased in the group treated with DM+the EB-AMDK19 dead cells. In addition, the expression of PPARγ (p<0.001), CEBPα (p<0.001), CD36 (p<0.01) and LPL (p<0.01) significantly decreased in the group treated with the *Akkermansia muciniphila* BAA-835 strain compared to the group treated with the BAA-835 strain. That is, it could be confirmed that the *Akkermansia muciniphila* EB-AMDK19 strain of the present invention had a better effect on the inhibition of adipocyte differentiation of 3T3-L1 cells than the *Akkermansia muciniphila* BAA-835 strain.

Example 4: Evaluation of Anti-Obesity Effect

4.1. Animal Models and Sampling

Animal experiments were performed in accordance with the Animal Use and Care Protocol of the Institutional Animal Care and Use Committee (IACUC). As experimental animals, 8-week-old male C57BL mice (6 mice per group) were purchased and acclimated for one week, and then bred and housed for 8 weeks. During breeding, the animals were acclimated for one week at a temperature of 22° C.; and a relative humidity of 40 to 60% with 12-hr light/12-hr dark cycles.

To induce obesity, the animals were fed with high-fat diet (60 kcal % fat; Research Diets Inc., NJ, USA) and allowed to freely access drinking water.

The experimental animals were divided into five groups as follows:

- Experimental group I (Normal): normal diet normal control group
- Experimental group II (HFD): obesity-induced group fed with high-fat diet
- Experimental group II (GC): group fed with high fat diet for obesity induction and administered with *Garcinia carnbogia*
- Experimental group IV (BAA-835): group fed with high fat diet for obesity induction and administered with *Akkermansia muciniphila* BAA-835 type strain
- Experimental group V (EB-AMDK19): group fed with high fat diet for obesity induction and administered with *Akkermansia muciniphila* EB-AMDK19 strain (a probiotic form).

In the case of experimental group V, after the induction of obesity by high-fat diet, *Akkermansia muciniphila* EB-AMDK19 dead cells were orally administered every day at a concentration of $1\times10^8$ cells/150 μl PBS (25% glycerol and 0.05% cysteine/PBS).

Normal mice were fed with 10% fat diet. As negative controls, each of *Garcinia Cambogia* (GC, 60% HCA 1000 mg/kg), known as a food functional food useful for reducing body weight, and the *Akkermansia muciniphila* BAA-835 strain (a probiotic form), was administered. To the normal group and the high-fat diet group (HFD), PBS (25% glycerol and 0.05% cysteine/PBS) was orally administered every day in the same amount as that of the high-fat diet or *Garcinia Cambogia* in order to exclude the effect of administration-induced stress or the like.

4.2. Changes in Body Weight and Feed Intake

At 12 weeks after obesity induction, the changes in body weight, body fat and tissue weight of each experimental group by administration of the *Akkermansia muciniphila* EB-AMDK19 strain were measured, and the results of the measurement are shown in FIGS. 9A-9D.

Referring to FIGS. 9A-9D, even in the group administered with *Garcinia Cambogia* or the *Akkermansia muciniphila* BAA-835 strain, a slight reduction in the body weight was observed, but a significant reduction in the body weight could not be seen.

In comparison with this, the group administered with the *Akkermansia muciniphila* EB-AMDK19 strain showed a significant reduction in body weight compared to the high-fat diet group (HFD) (P<0.05). In addition, referring to FIGS. 9A-9D, the food intake of the group administered with the *Akkermansia muciniphila* EB-AMDK19 strain significantly decreased compared to that of the high-fat diet group. From these results, it can be seen that the *Akkermansia muciniphila* EB-AMDK19 strain of the present invention induces continued decreases in food intake and body weight.

4.3. Changes in Tissue and Body Fat Weights

At the end of the experiment, liver and spleen were extracted under $CO_2$ anesthesia, washed with saline, dewatered, and then weighed. The results of the measurement are shown in FIGS. 10A-10F.

Referring to FIGS. 10A-10F, it could be seen that all the administered groups showed significant decreases in fat weights compared to the high-fat diet group. These results suggest that the *Akkermansia muciniphila* strain of the present invention contributed to suppressing body weight gain by reducing lipid accumulation and inflammation in the spleen and liver cells.

As shown in FIGS. 10A-10F, the weights of liver, spleen, subcutaneous fat, epididymal fat and mesenteric fat all significantly increased in the group fed with high-fat diet (HFD) compared to the normal group, and the weights of liver, spleen, subcutaneous fat, epididymal fat and mesenteric fat significantly decreased in the group administered with the *Akkermansia muciniphila* EB-AMDK19 strain. In particular, in the case of subcutaneous fat, the group administered with the *Akkermansia muciniphila* EB-AMDK19 strain showed a more significant decrease in subcutaneous fat weight compared to the group administered with *Garcinia Cambogia* or the *Akkermansia muciniphila* BAA-835 strain (P<0.01). In the case of epididymal fat, only the group administered with the *Akkermansia muciniphila* EB-AMDK19 strain showed a significant decrease in epididymal fat weight compared to the high-fat diet group (P<0.05).

These results suggest that administration of the *Akkermansia muciniphila* EB-AMDK19 strain has a better effect on the suppression of obesity induced by high-fat diet than administration of *Garcinia Cambogia* or the *Akkermansia muciniphila* BAA-835 strain.

In particular, these results show that the *Akkermansia muciniphila* EB-AMDK19 strain has a strong effect on the reduction of body fat, known to cause complications such as cardiovascular disease, rather than a simple effect on weight loss, and has a greater significance as an anti-obesity agent.

Example 5: Evaluation of Effect on Treatment or Prevention of Metabolic Disease

5.1. Oral Glucose Tolerance Test (OGTT)

In order to evaluate the effect of administration of the *Akkermansia muciniphila* EB-AMDK19 strain on glucose tolerance, at 12 weeks after the start of the experiment, 2 g/kg of glucose was orally administered to the mice after 18 hours of fasting. Immediately before and at 30, 60, 90 and 120 minutes after administration of glucose, blood was taken from the tail vein of each mouse, and the glucose level of the blood was measured with a blood glucose meter. The results of the measurement are shown in FIGS. 11A-11D.

Referring to FIGS. 11A-11D, the group administered with the *Akkermansia muciniphila* EB-AMDK19 strain immediately before glucose administration showed the greatest decrease in the blood glucose level among the groups administered, but this decrease was not significant.

30 minutes after glucose administration, the blood glucose levels in all the groups administered decreased compared to that of the high-fat diet group ($P<0.001$), and the blood glucose level in the group administered with the *Akkermansia muciniphila* EB-AMDK19 strain remarkably decreased compared to those of the other groups to a level that is insignificant compared to that of the normal group. These results show that oral administration of the *Akkermansia muciniphila* EB-AMDK19 strain can alleviate obesity-induced hyperlipidemia and enhance glucose tolerance.

5.2. Analysis of Blood Lipid Biochemical Indicators

After 18 hours of fasting, blood was taken from each experimental animal, and using the plasma separated from the blood, insulin concentration and insulin resistance index (HOMA-IR) levels were measured, and the concentration of total cholesterol (TC), a lipid content indicator, and the concentration of glutamic pyruvic transaminase (GPT), a liver function indicator, were measured.

Specifically, the insulin concentration was measured using an insulin ELISA kit (Morinaga, Japan), and the insulin resistance index (HOMA-IR index) was calculated using the following equation:

$$\text{Fasting insulin concentration (mU/L)} \times \text{fasting glucose concentration (mmol/L)}/22.5$$

Total cholesterol (TC) and glutamic pyruvic transaminase (GPT), which were lipid composition indicators, were quantified using the respective measurement kits all purchased from Asan Pharmaceutical Co., Ltd. (Korea). The results are shown in FIGS. 12A-12D.

The results of measurement of the insulin concentration showed that the insulin concentration and insulin resistance index (HOMA-IR) that increased in the high-fat diet group significantly decreased in all the groups administered. In addition, it was observed that the cholesterol level and insulin resistance index that increased in the high-fat diet group significantly decreased only in the group administered with the *Akkermansia muciniphila* EB-AMDK19 strain ($P<0.05$). The GPT concentration indicative of the degree of liver damage significantly decreased in all the groups administered. The blood insulin, cholesterol and GPT concentrations that decreased due to administration of the *Akkermansia muciniphila* EB-AMDK19 strain are closely related to the weight loss effect.

Figure 13A:
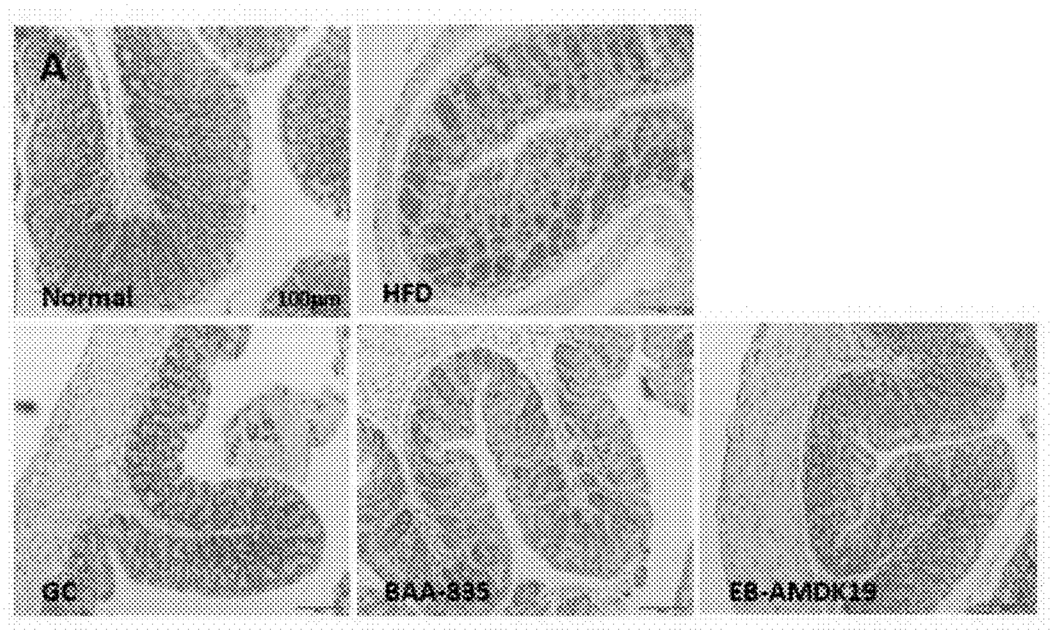
FIGS. 13A and 13B show Alcian blue staining images of a normal group, a high-fat diet group (HFD), a group administered with *Garcinia cambogia* (GC), a group administered with the *Akkermansia muciniphila* ATCC BAP-835 strain (BAA-835), and a group administered with the *Akkermansia muciniphila* EB-AMDK19 strain of the present invention (EB-AMDK19), and depicts a graph showing the positive area in each group, obtained by quantifying the images.
Figure 13B:
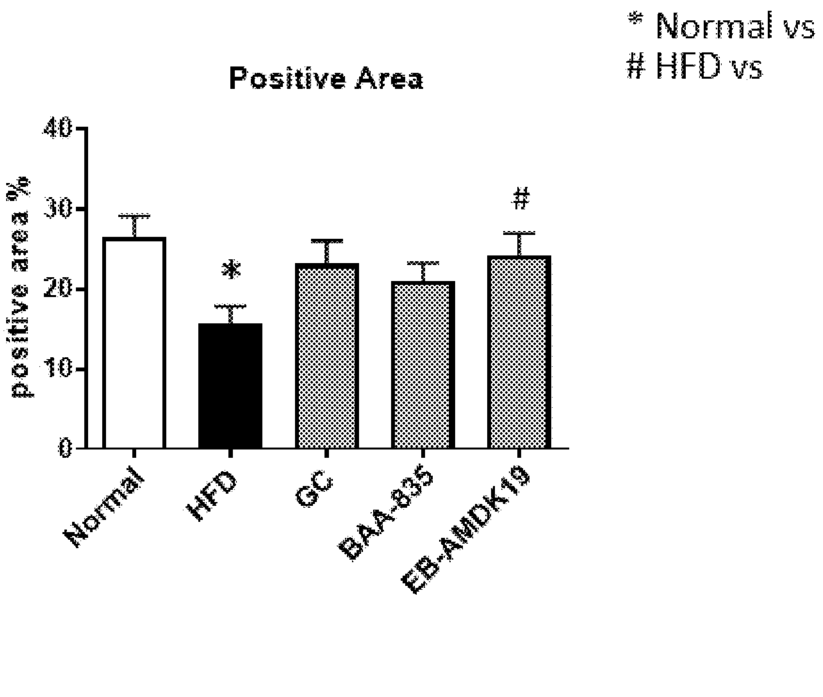

5.3. Alleviation of Damage to Colonic Mucosa 5.3.1 Histological Evaluation of Colonic Mucosa In order to examine whether the *Akkermansia muciniphila* EB-AMDK19 strain of the present invention has the effect of treating damage to colonic mucosa, colon tissues from the normal group, the high-fat diet group (HFD), the group administered with *Garcinia Cambogia* (GC), the group administered with the *Akkermansia muciniphila* ATCC BAA-835 strain (BAA-835), and the group administered with the *Akkermansia muciniphila* EB-AMDK19 strain (EB-AMDK19) were stained with Alcian blue staining and imaged (FIGS. 13A and 13B). In addition, the results obtained by quantifying the positive area (%) in each group on the basis of these results are graphically shown in FIGS. 13A and 13B.

As shown in FIGS. 13A and 13B, it was confirmed that the goblet cells and superficial epithelial tissue in the colon tissue from the high-fat diet group (HFD) were lost and a number of immune cells also infiltrated the colon tissue.

In contrast, it could be seen that the mucosa structure in the colon tissue from the group administered with the *Akkermansia muciniphila* EB-AMDK19 strain of the present invention was maintained and was similar to that in the colon tissue from the normal group. In addition, it could be seen that the goblet cells that decreased in the colon tissue from the high-fat diet group (HFD) significantly increased in the group administered with the *Akkermansia muciniphila* EB-AMDK19 strain ($p<0.05$).

5.3.2 Evaluation of Expression of Tight Junction Proteins

Figure 14:
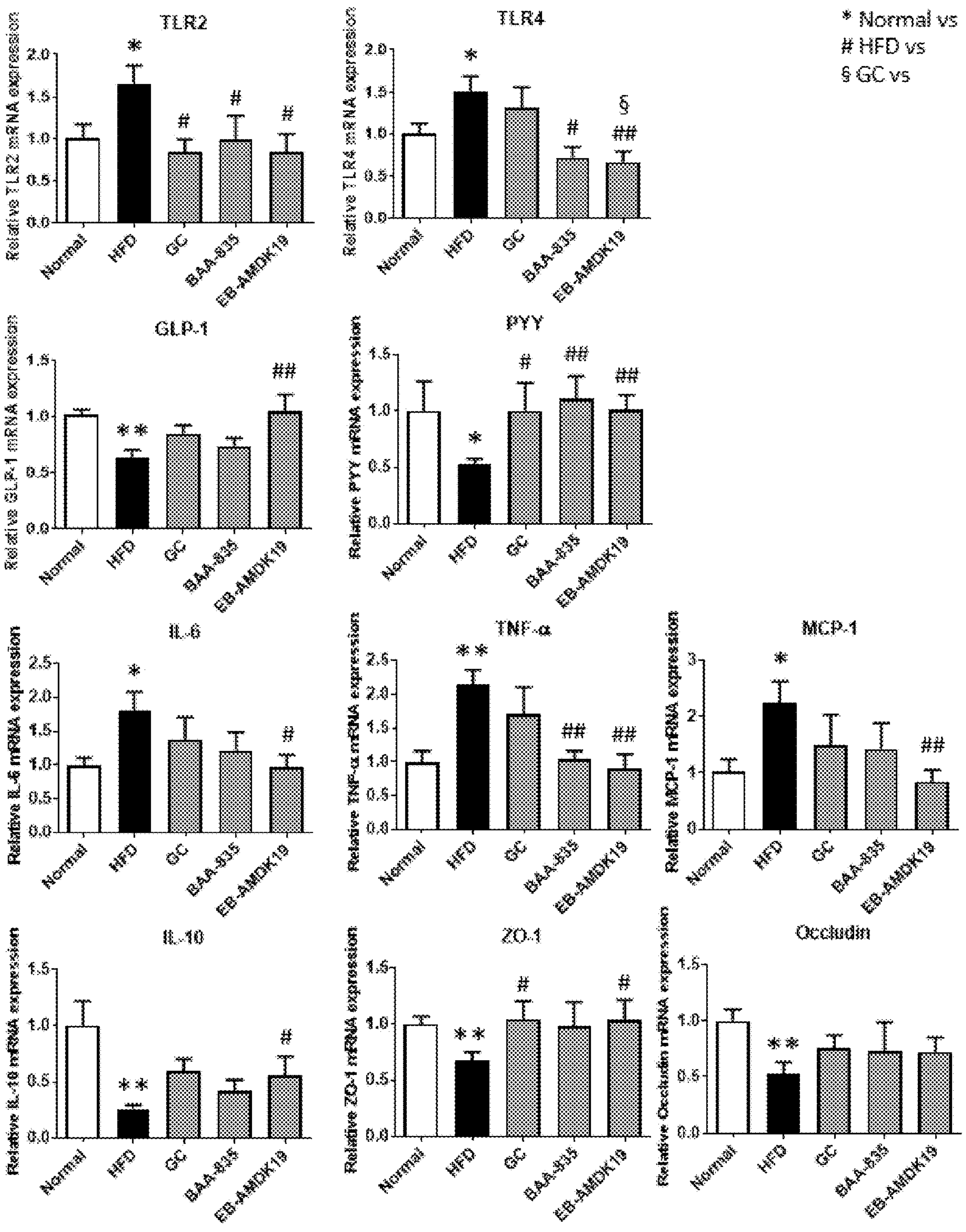
FIG. 14 shows changes in the expression of TLR4, TLR2, GLP-1, PYY, IL-6, TNF-α, MCP-1, IL-10, ZO-1 and occluding in the enterocytes of mice of each test group.
Figure 15A:
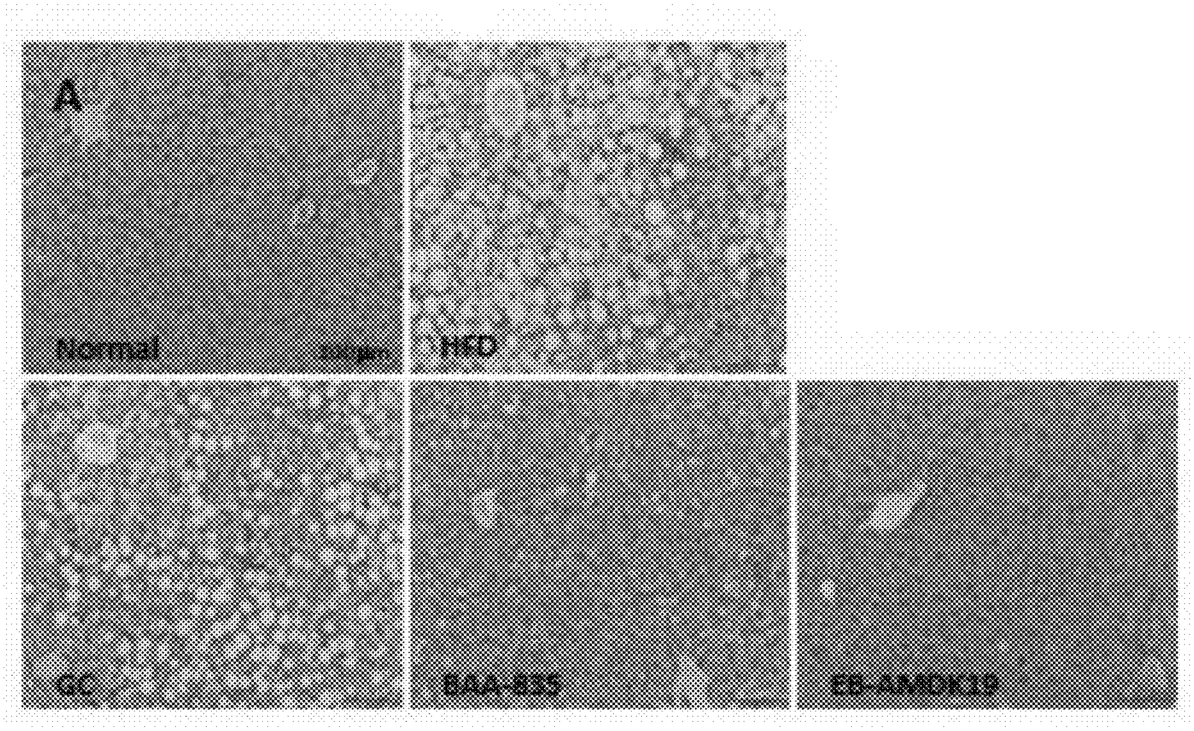
FIGS. 15A, 15B, 16A, and 16B are optical micrographs of hepatocytes and lipid droplets, obtained after H & E staining, and are graphs showing liver steatosis scores in each group.
Figure 15B:
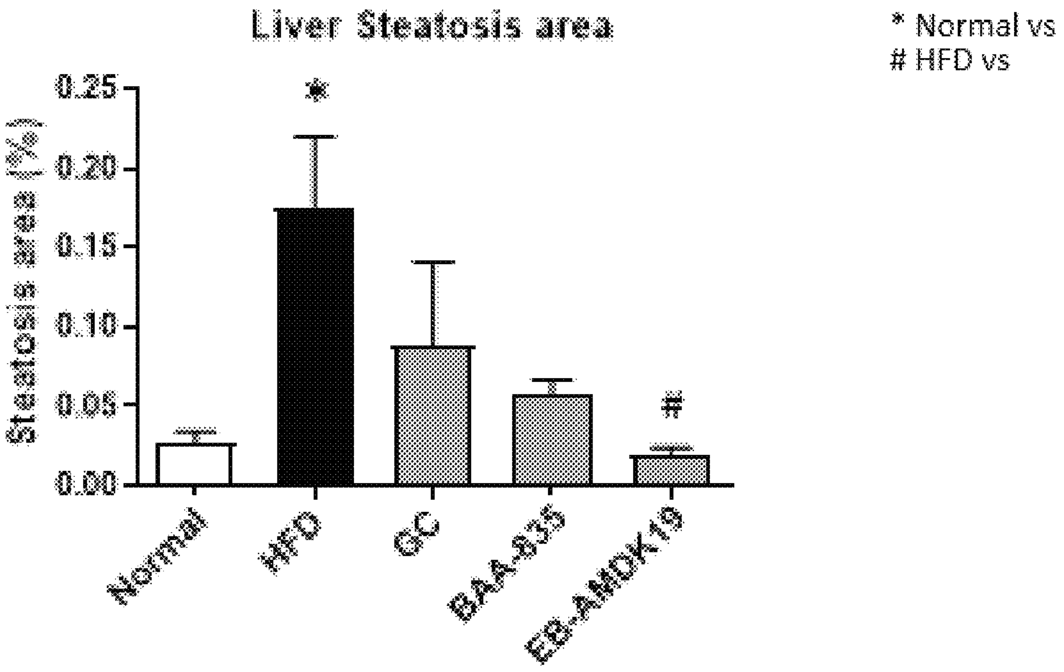
Figure 16A:
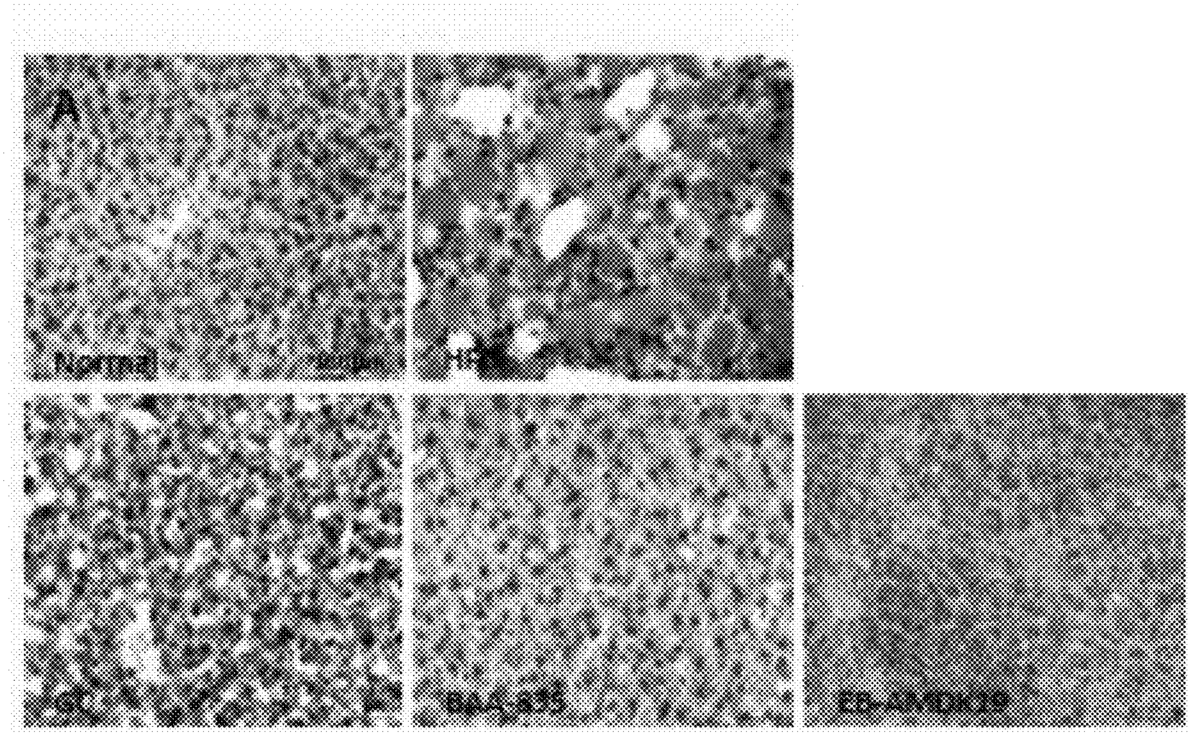
Figure 16B:
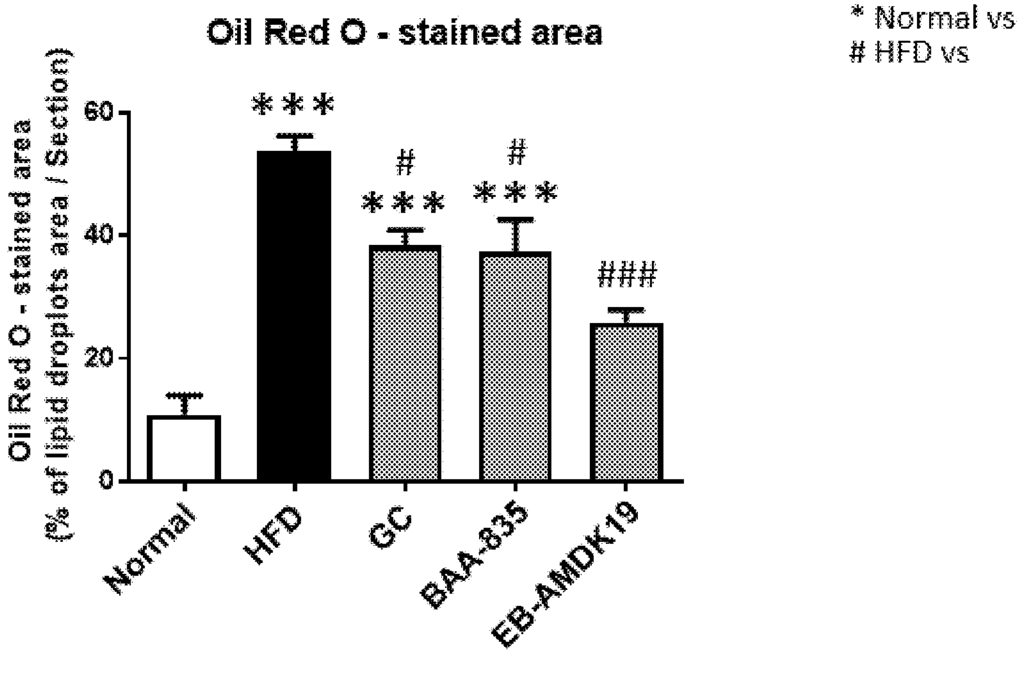

In order to evaluate the effect of the strain of the present invention on the expression of colonic immune-related hormones and tight junction hormones, PCR was performed in the same manner as Example 2.2 using the primers shown in Table 10 below, and the results are shown in FIG. 14.

TABLE 10

| Targets | Primer sequences | SEQ ID NOs. |
|---|---|---|
| GAPDH | F: 5'-GAC ATC AAG AAG GTG GTG AAG CAG-3' | SEQ ID NO: 35 |
| | R: 5'-ATA CCA GGA AAT GAG CTT GAC AAA-3' | SEQ ID NO: 36 |
| TLR2 | F: 5'-AAG GAG GTG CGG ACT GTT TC-3' | SEQ ID NO: 37 |
| | R: 5'-GAG CCA AAG AGC TCG TAG C-3' | SEQ ID NO: 38 |
| TLR4 | F: 5'-CCT GAT GAC ATT CCT TCT TCA AC-3' | SEQ ID NO: 39 |
| | R: 5'-TTG TTT CAA TTT CAC ACC TGG ATA AA-3' | SEQ ID NO: 40 |
| GLP-1 | F: 5'-GGC ACA TTC ACC AGC GAC TAC-3' | SEQ ID NO: 41 |
| | R: 5'-CAA TGG CGA CTT CTT CTG GG-3' | SEQ ID NO: 42 |
| PYY | F: 5'-CGG CAG CGG TAT GGA AAA A-3' | SEQ ID NO: 43 |
| | R: 5'-TGT GAA GAG CAG TTT GGA GAA CA-3' | SEQ ID NO: 44 |
| IL-6 | F: 5'-CCT CTG GTC TTC TGG AGT ACC-3' | SEQ ID NO: 45 |
| | R: 5'-ACT CCT TCT GTG ACT CCA GC-3' | SEQ ID NO: 46 |
| TNF-α | F: 5'-GAC CCT CAC ACT CAG ATC ATC TTC T-3' | SEQ ID NO: 47 |
| | R: 5'-CCA CTT GGT GGT TTG CTA CGA-3' | SEQ ID NO: 48 |

TABLE 10-continued

| Targets | Primer sequences | SEQ ID NOs. |
|---|---|---|
| MCP-1 | F: 5'-AAG AGA TCA GGG AGT TTG CT-3' | SEQ ID NO: 49 |
| | R: 5'-CTG CCT CCA TCA ACC ACT TT-3' | SEQ ID NO: 50 |
| IL-10 | F: 5'-ATA ACT GCA CCC ACT TCC CA-3' | SEQ ID NO: 51 |
| | R: 5'-GGG CAT CAC TTC TAC CAG GT-3' | SEQ ID NO: 52 |
| ZO-1 | F: 5'-TTT TTG ACA GGG GGA GTG G-3' | SEQ ID NO: 53 |
| | R: 5'-TGC TGC AGA GGT CAA AGT TCA AG-3' | SEQ ID NO: 54 |
| Occludin | F: 5'-ATG TCC GGC CGA TGC TCT C-3' | SEQ ID NO: 55 |
| | R: 5'-TTT GGC TGC TCT TGG GTC TGT AT-3' | SEQ ID NO: 56 |

In addition, as shown in FIG. 14, the expression of the inflammatory mediators TLR2 (toll-like receptor 2, $p<0.05$), TLR4 ($p<0.05$), IL-6 ($p<0.05$), TNF-$\alpha$ ($p<0.01$), and MCP-1 (monocyte chemoattractant protein-1, $p<0.05$), which increased in the high-fat diet group, significantly decreased in the group administered with the *Akkermansia muciniphila* EB-AMDK19 strain (TLR2 ($p<0.05$), TLR4 ($p<0.05$), IL-6 ($p<0.05$), TNF-$\alpha$ ($p<0.01$), and MCP-1 ($p<0.05$)). In addition, it was observed that the expression of TLR2, TLR4 and TNF-$\alpha$ also decreased in the group administered with the *Akkermansia muciniphila* BAA-835. The expression of the anti-inflammatory cytokine IL-10 ($p<0.05$) significantly increased only in the group administered with the *Akkermansia muciniphila* EB-AMDK19 strain compared to the high-fat diet group.

Meanwhile, the expression of the appetite suppressant hormone GLP-1 (glucagon like peptide-1) significantly decreased in the high-fat diet group ($p<0.01$), but significantly increased in the group administered with the *Akkermansia muciniphila* EB-AMDK19 strain compared to the high-fat diet group ($p<0.01$). The expression of another appetite suppressant hormone PYY (peptide YY) significantly decreased in the high-fat diet group ($p<0.05$), but significantly increased in all the group administered with *Garcinia Cambogia* ($p<0.05$), the group administered with the *Akkermansia muciniphila* BAA-835 strain ($p<0.01$), and the group administered with the EB-AMDK19 strain ($p<0.01$), compared to the control group. The expression of the tight junction proteins ZO-1 (zonular occludens-1, $p<0.01$) and occludin ($p<0.01$) significantly decreased in the high-fat diet group. In contrast, in the group administered with the *Akkermansia muciniphila* EB-AMDK19 strain of the present invention, the expression of ZO-1 significantly increased ($p<0.05$), and the tight junction protein occludin also increased, which is expressed in colonic mucosa and maintains intestinal permeability at a suitable level. That is, it can be seen that administration of the *Akkermansia muciniphila* EB-AMDK19 strain of the present invention provides the effects of alleviating obesity-induced inflammation of colonic mucosa and improving intestinal permeability.

5.4. Amelioration of Hepatic Steatosis

Visceral adipose tissue was extracted from the mice of each experimental group, and then weighed. A portion of the visceral adipose tissue was taken and fixed in 10% buffered formalin. Next, it was embedded in paraffin and sectioned to a thickness of 4 mm using a microtome (Reichert-Jung 2050, ALT, USA). The sections were mounted on glass slides, and then stained by H & E (Hematoxylin & Eosin) and ORO (Oil Red O) staining similar to that of Example 3.1. Next, the shape and state of hepatocytes and lipid droplets were observed under an optical microscope at 200× to 400× magnification. The results are shown in FIGS. 15A, 15B, 16A, and 16B.

Referring to FIGS. 15A, 15B, 16A, and 16B, worsened steatosis ($p<0.05$) and increased lipid droplets ($p<0.001$) in the high-fat diet group significantly decreased in the group administered with the *Akkermansia muciniphila* EB-AMDK19 strain ($p<0.01$ and $p<0.001$, respectively). It was observed that the decrease rate of lipid droplets in the group administered with the *Akkermansia muciniphila* EB-AMDK19 strain was more significant than that in the group administered with *Garcinia Cambogia* or the *Akkermansia muciniphila* BAA-835 strain, indicating that the *Akkermansia muciniphila* EB-AMDK19 strain showed the greatest improvement.

5.5. Change in Adipocyte Diameter

Figure 17A:
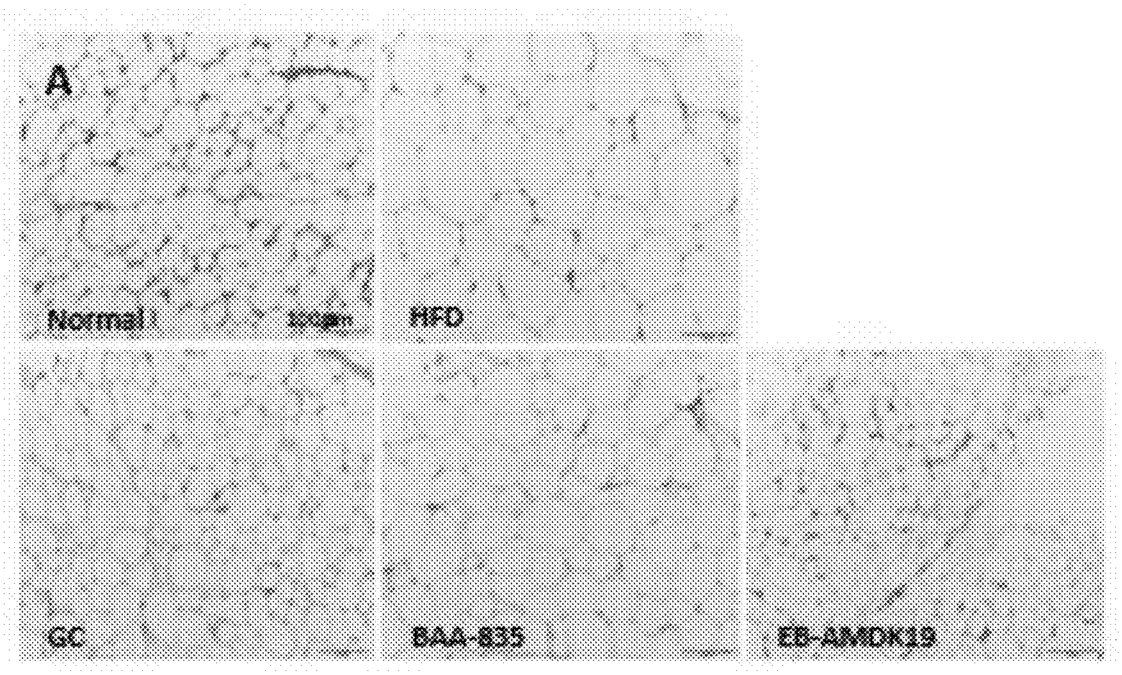
FIGS. 17A and 17B depict photographs and a graph, which show the degree of lipid accumulation in the mesenteric adipose tissue of each test animal after treatment with the *Akkermansia muciniphila* EB-AMDK19 strain of the present invention.
Figure 17B:
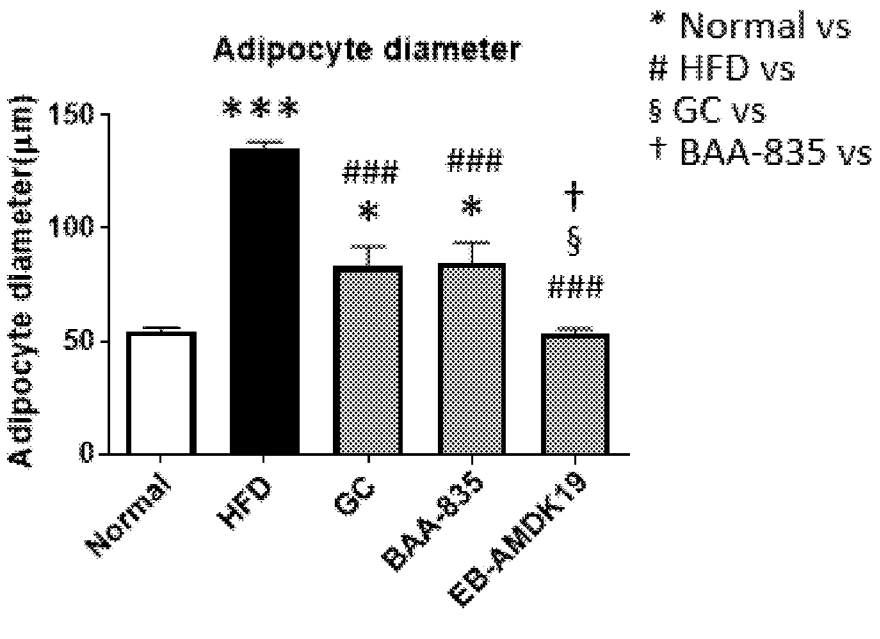

Mesenteric fat tissue was isolated from the mice of each experimental group and analyzed by H & E staining, and the results of the analysis are shown in FIGS. 17A and 17B. Referring to FIGS. 17A and 17B, the diameter of adipocytes in the high-fat diet group increased compared to that in the normal group ($p<0.001$). In contrast, the diameter of adipocytes was observed to decrease in the group administered with *Garcinia Cambogia*, the group administered with the *Akkermansia muciniphila* BAA-835 strain, and the group administered with the *Akkermansia muciniphila* EB-AMDK19 strain, compared to the high-fat diet group ($p<0.001$). In particular, the diameter of adipocytes in the group administered with the *Akkermansia muciniphila* EB-AMDK19 strain of the present invention significantly decreased compared to those in the group administered with the *Garcinia Cambogia* and the group administered with the *Akkermansia muciniphila* BAA-835 strain.

Example 6: Analysis of Microbiota in Feces 6.1. Changes in Microbial Diversity

For analysis of intestinal microorganisms, feces were collected from the mice of each group, and genomic DNA was extracted therefrom using a QIAamp DNA stool mini kit (Qiagen, USA). To confirm the extracted microbial genomic DNA, the position of the band of the genomic DNA was determined by electrophoresis on 1.5% agarose gel (QA-Agarose, Q-biogene, USA) in 1×TAE buffer using an electrophoresis apparatus at 100 V for 25 minutes. The purity of DNA was measured at A260/A280 using a spectrophotometer.

To amplify a specific portion of variable region 3 of 16S rDNA from the microbial DNA isolated from feces, PCR was performed using specially constructed barcode primers. The amplified PCR product was sequenced using an Ion Torrent Next-Generation sequencing platform which is a next-generation sequencing (NGS) method, and the microbiota was analyzed. After reads with low quality scores or a very small number of reads were removed, the resulting microbial sequences are imported into the GREENGENES database, and OUTs (operational taxonomic units) were assigned.

Then, the microbiota between clusters was analyzed using the Quantitative insights into microbial ecology (QIIME) 1.9.0 which is a microbiome data integration analysis tool. To compare the alpha diversity between the groups administered with the microbial strains, PCA analysis was performed based on the results obtained for the normal group, the high-fat diet group, the group administered with the *Akkermansia muciniphila* BAA-835 strain, and the group administered with the *Akkermansia muciniphila* EB-AMDK19 strain. The alpha-diversity was analyzed and presented by OTUs and Chaol, and the beta-diversity was analyzed by UNIFRACBASED principal coordinates analysis (PCoA). Analysis of linear discriminant analysis effect size (LEfSe) was conducted through an online program (huttenhower.sph.harvard.edu/galaxy).

Figure 8A:
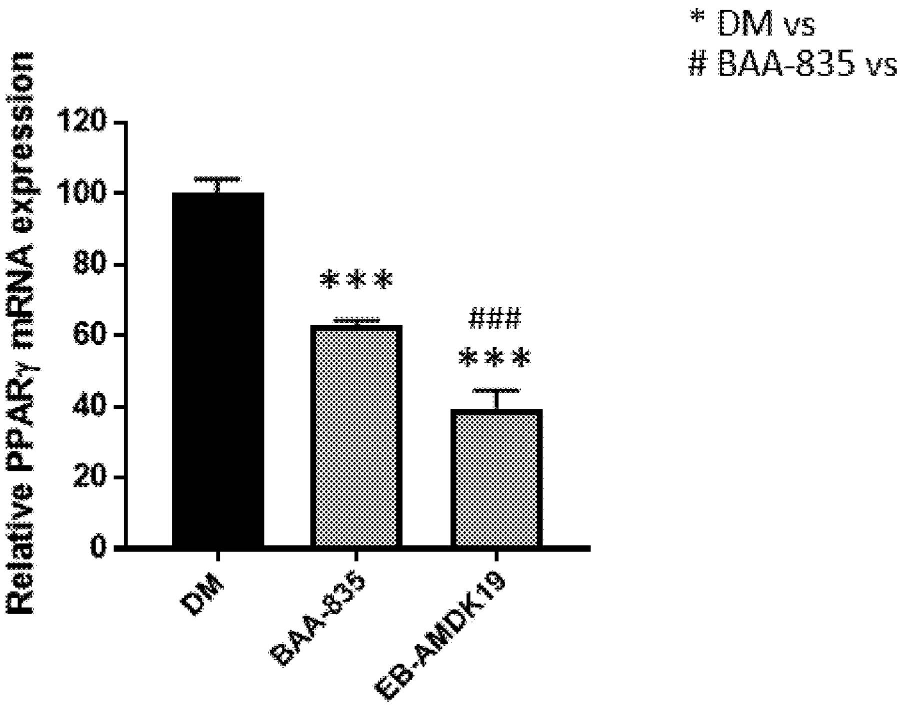
FIGS. 8A-8H are graphs showing the relative mRNA expression levels of PPARγ, CEBPα, aP2, CD36, ACC1, LPL (lipoprotein lipase), LDLR and FAS in preadipocytes after treatment with the *Akkermansia muciniphila* EB-AMDK19 strain of the present invention.
Figure 8B:
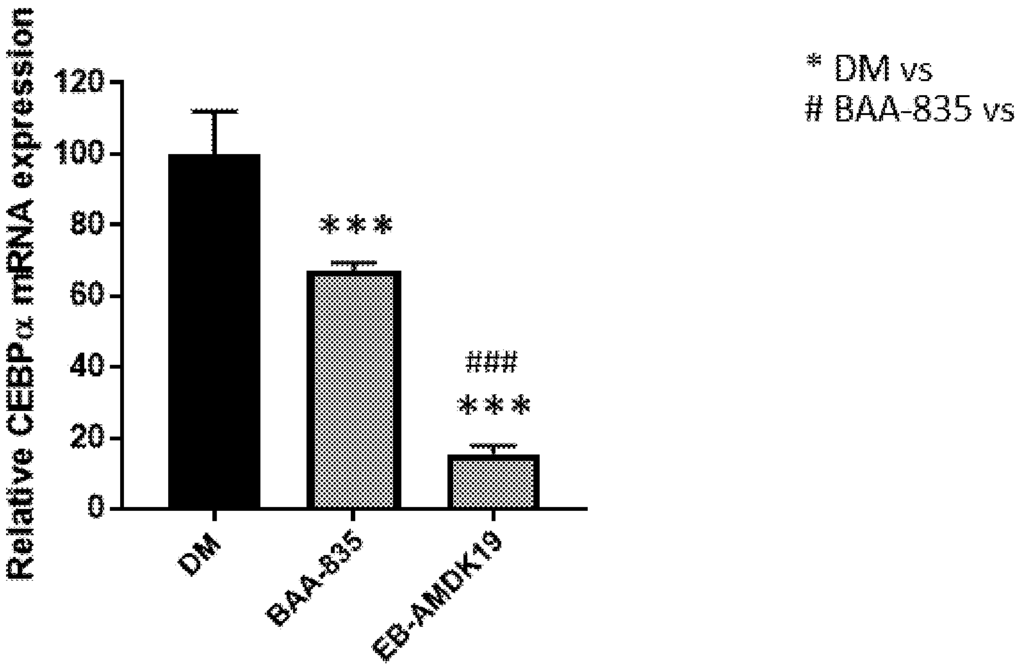
Figure 8C:
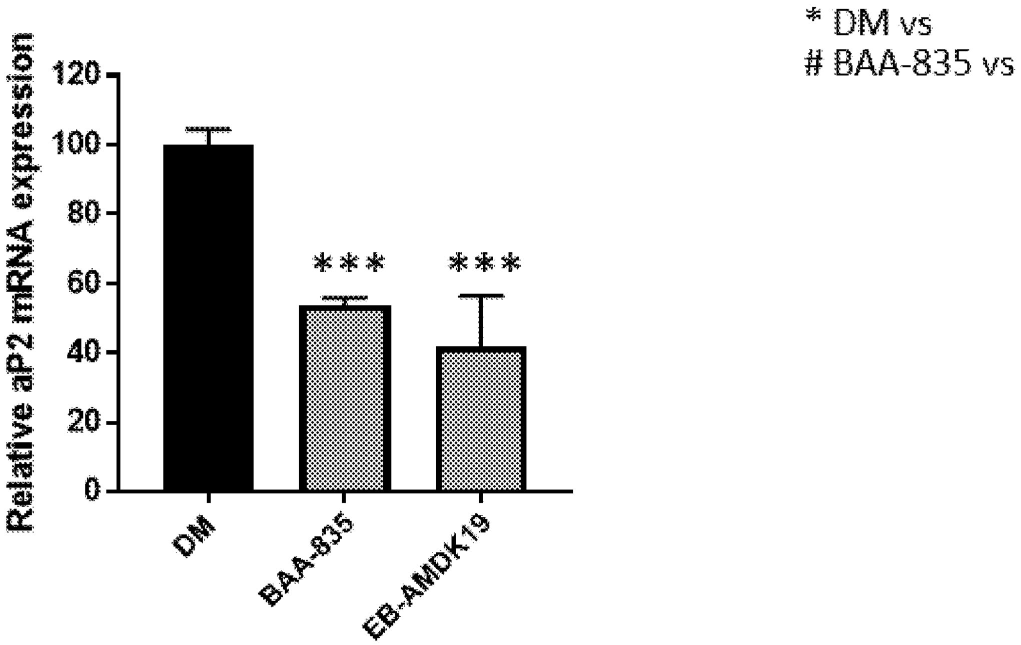
Figure 8D:
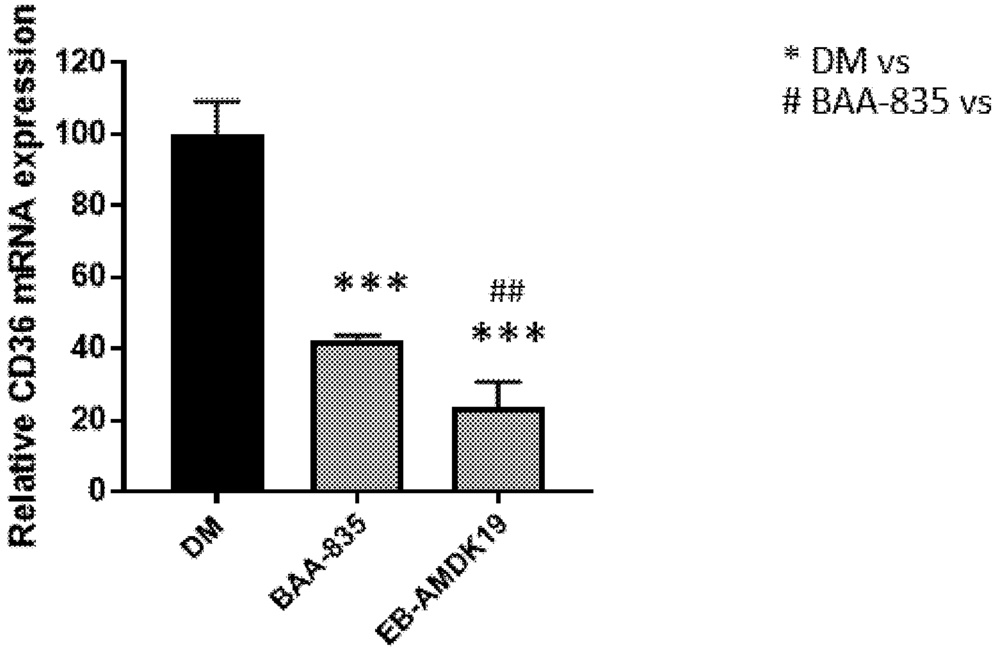
Figure 8E:
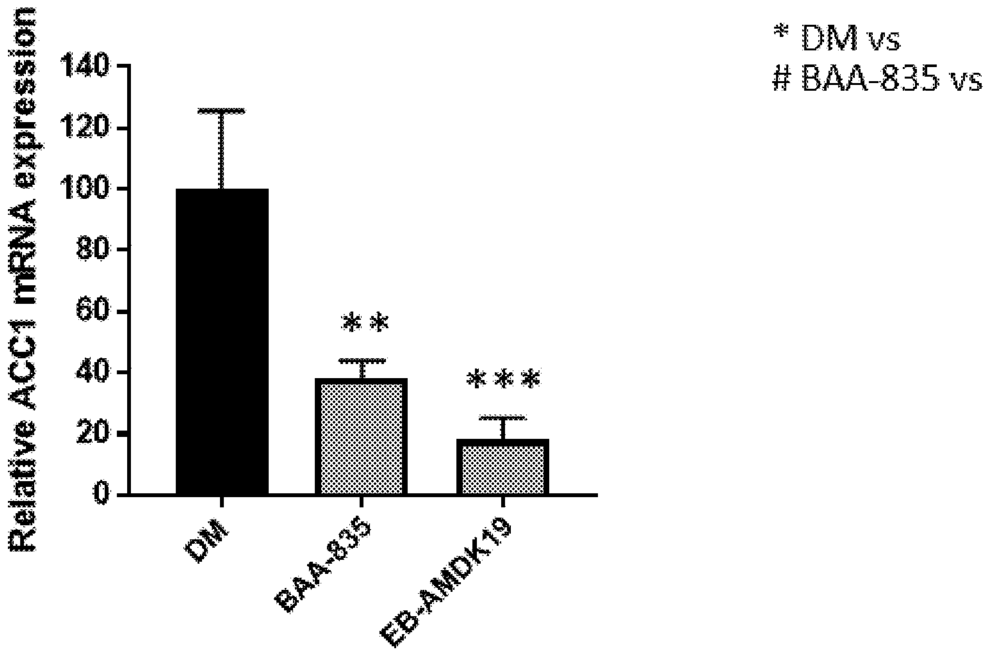
Figure 8F:
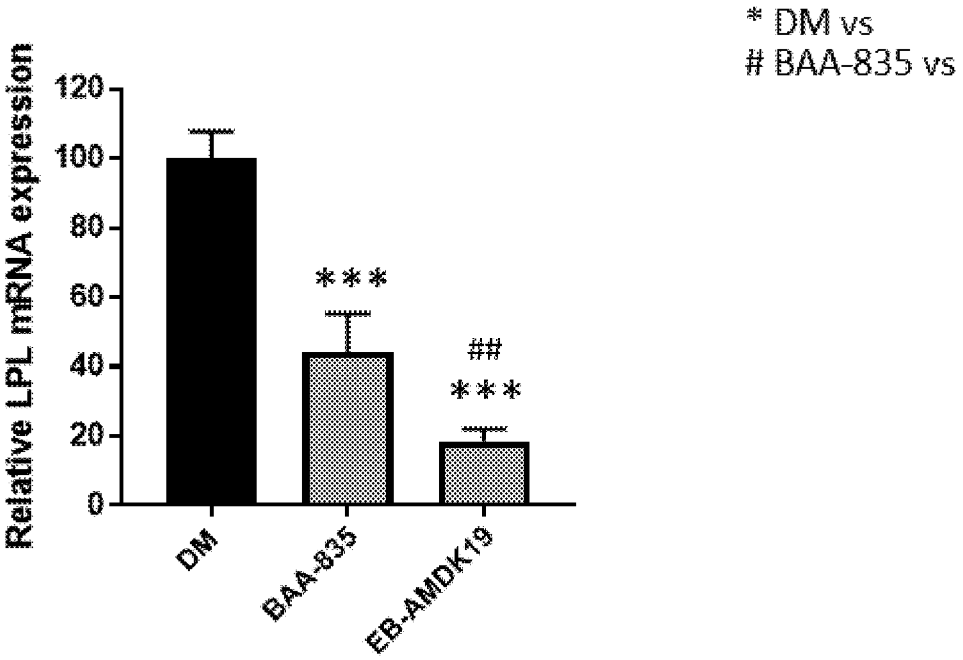
Figure 8G:
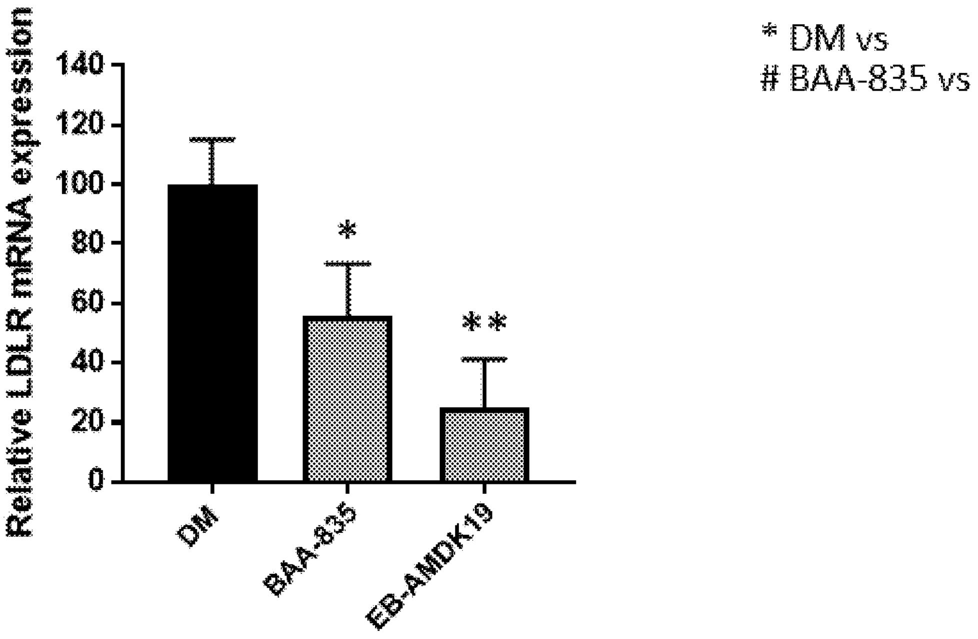
Figure 8H:
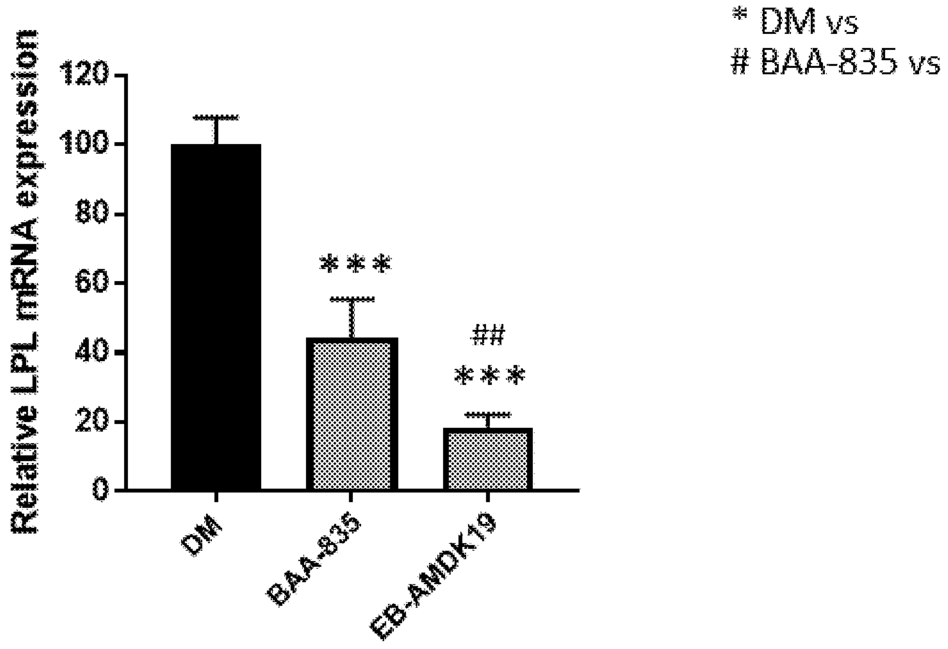
Figure 9A:
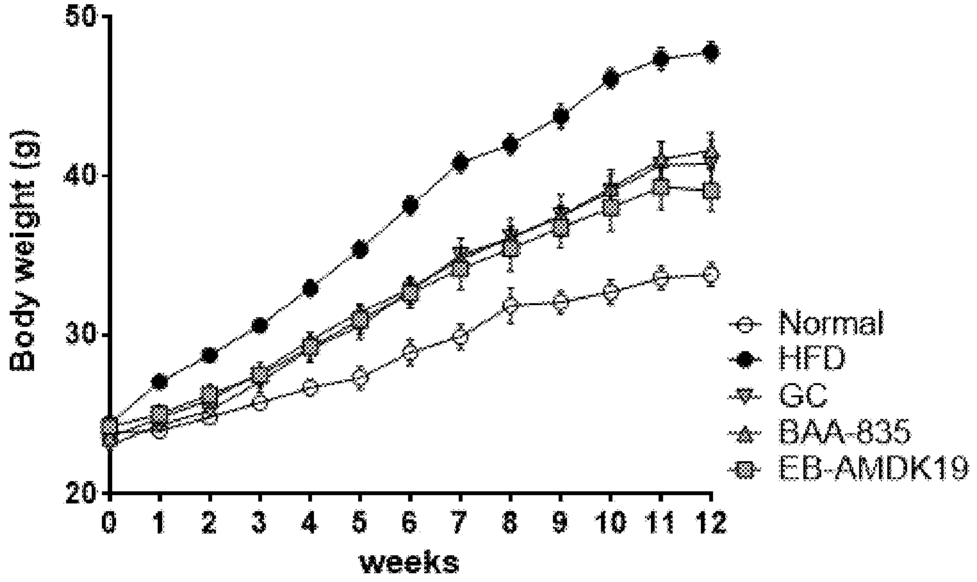
FIGS. 9A-9D show the results of analyzing changes in the body weight of a group administered with the *Akkermansia muciniphila* EB-AMDK19 strain of the present invention, a control group (DM), and a group administered with the *Akkermansia muciniphila* ATCC BAP-835 strain.
Figure 9B:
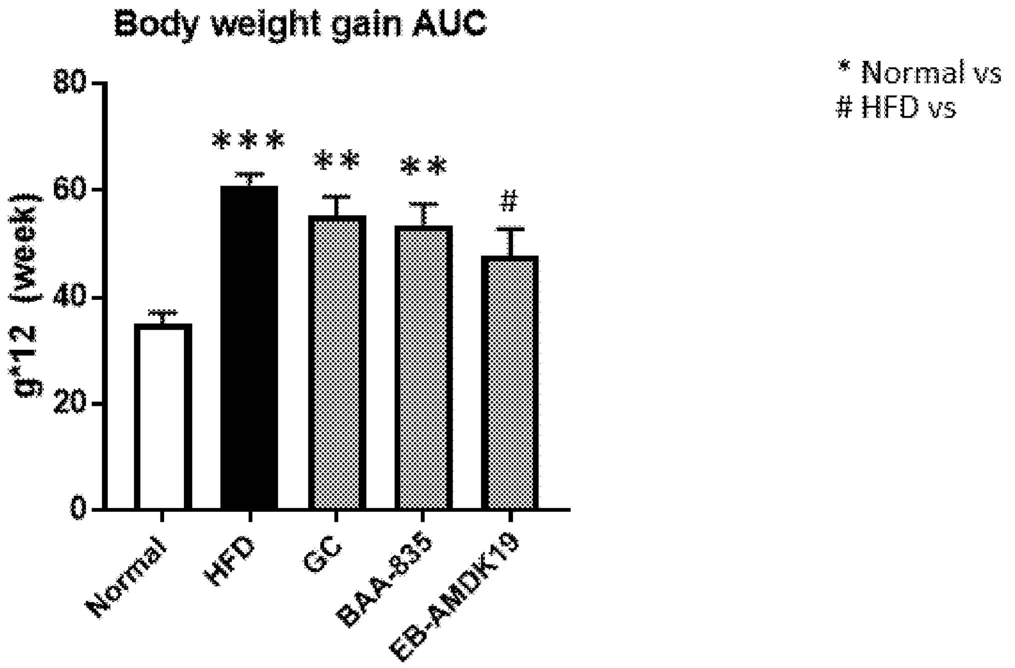
Figure 9C:
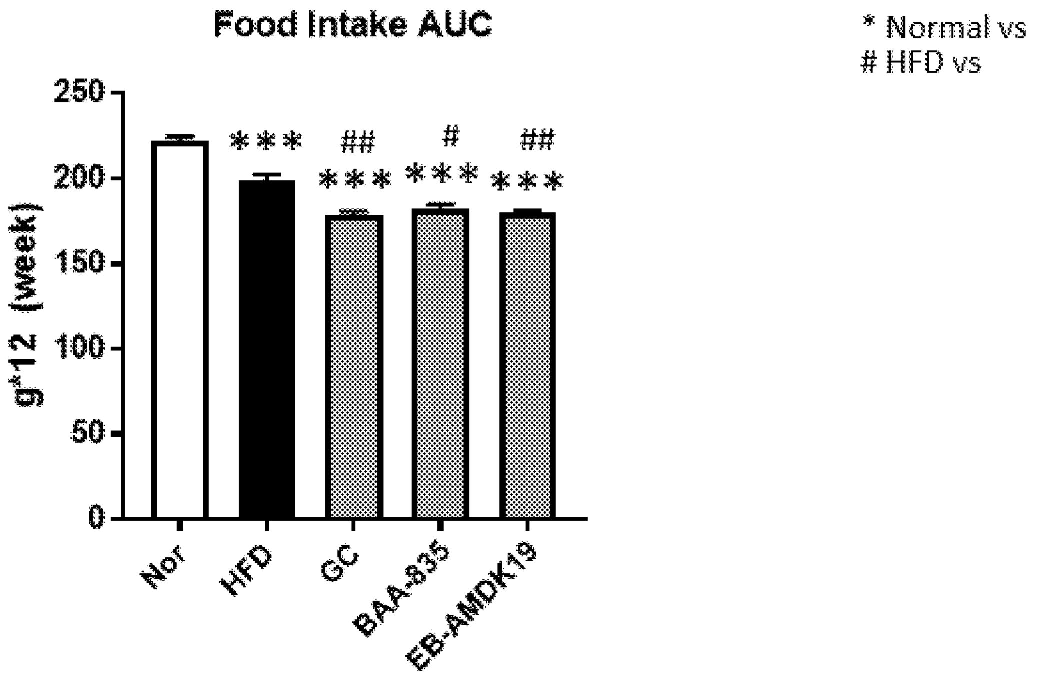
Figure 9D:
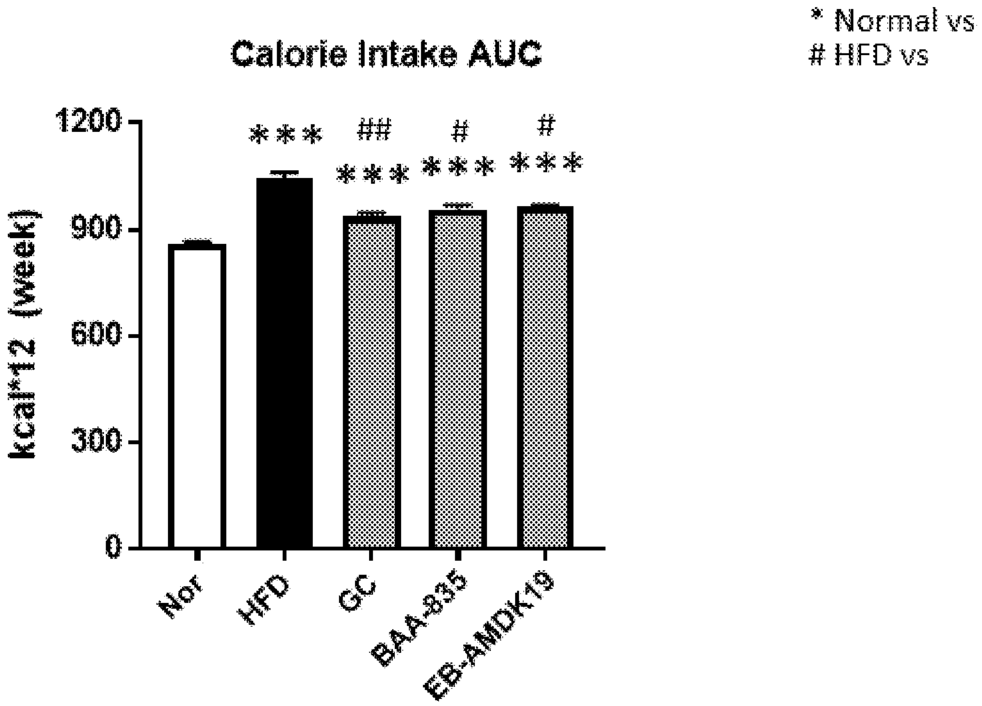
Figure 10A:
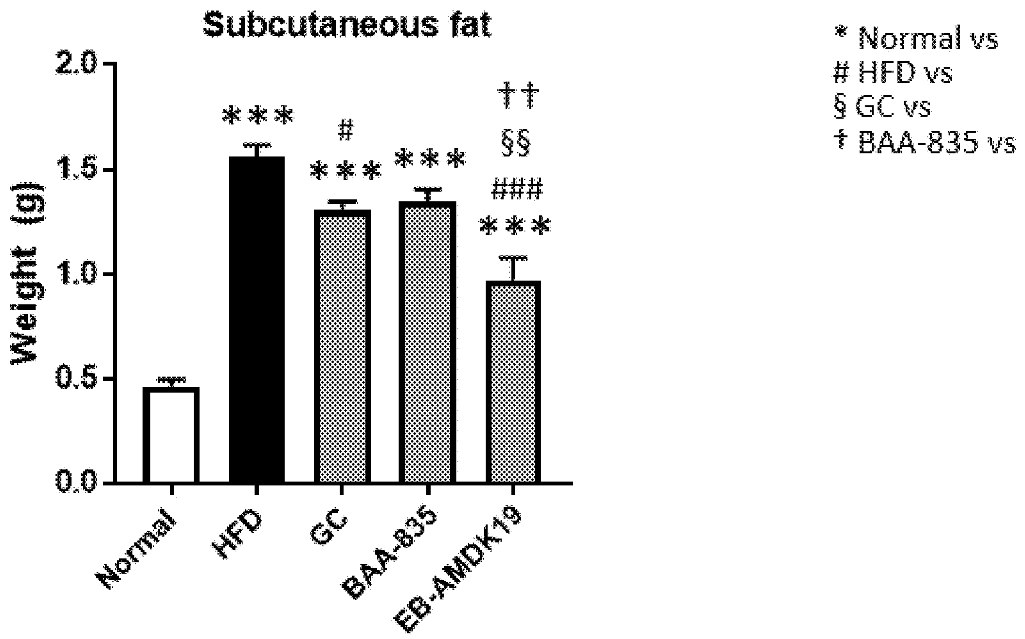
FIGS. 10A-10F show the results of analyzing changes in the weight of subcutaneous fat, epididymal fat and mesenteric fat of a group administered with the *Akkermansia muciniphila* EB-AMDK19 strain of the present invention, a control group (DM), and a group administered with the *Akkermansia muciniphila* ATCC BAP-835 strain.
Figure 10B:
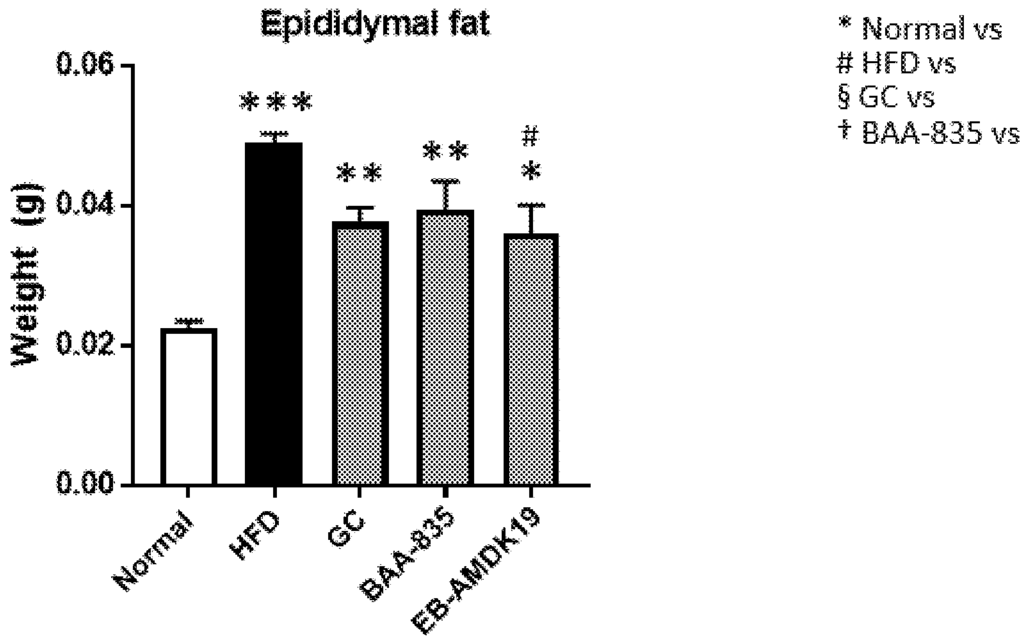
Figure 10C:
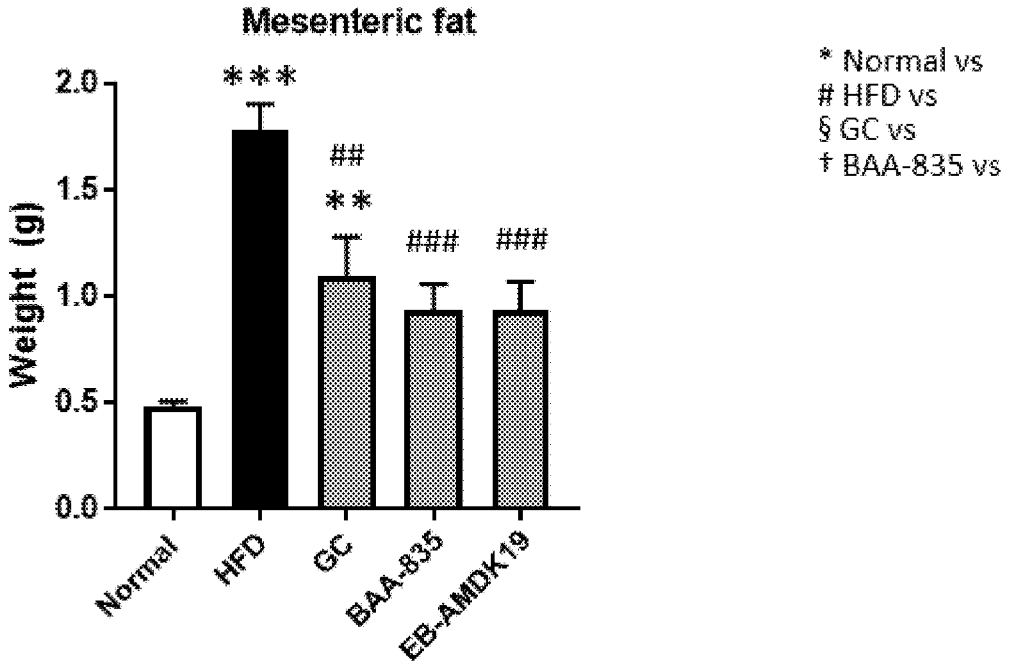
Figure 10D:
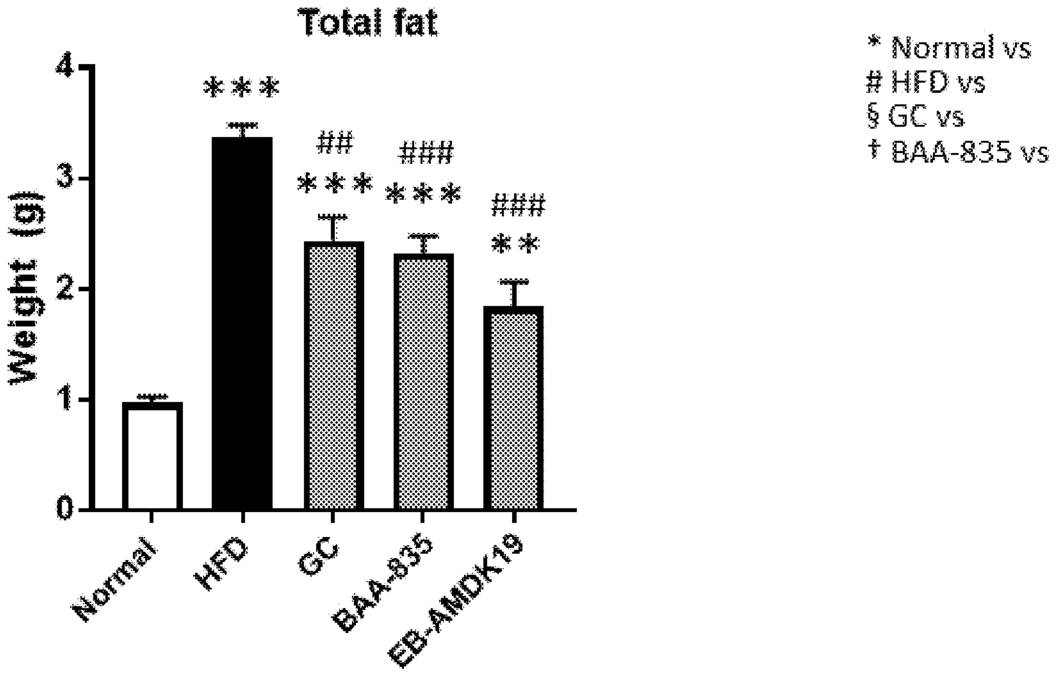
Figure 10E:
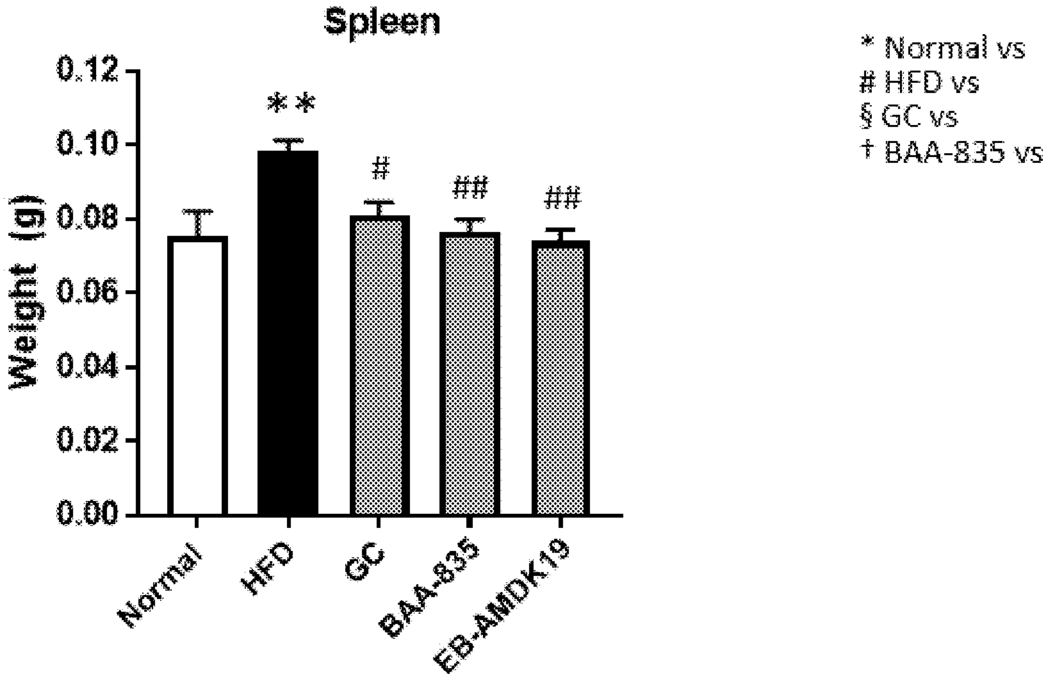
Figure 10F:
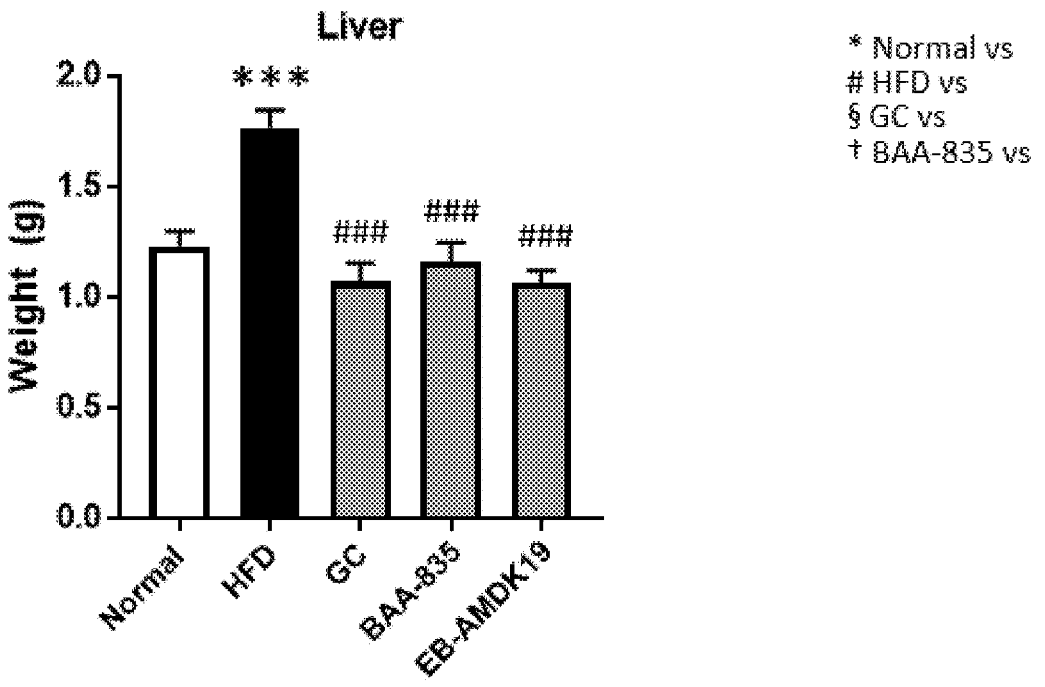
Figure 11A:
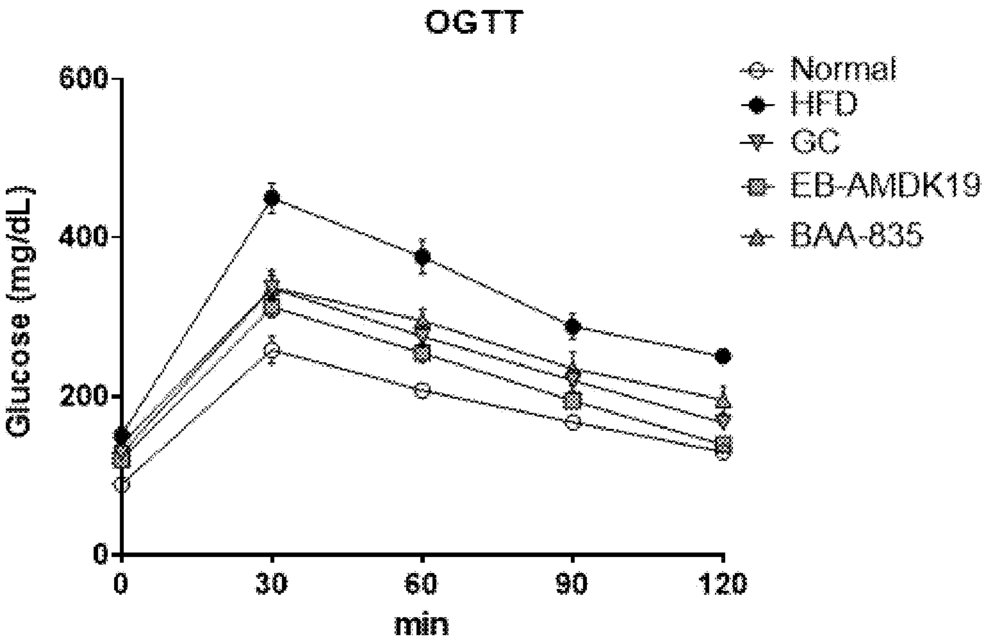
FIGS. 11A-11D show the results of analyzing changes in the glucose tolerance of a group administered with the *Akkermansia muciniphila* EB-AMDK19 strain of the present invention, a control group (DM), and a group administered with the *Akkermansia muciniphila* ATCC BAA-835 strain.
Figure 11B:
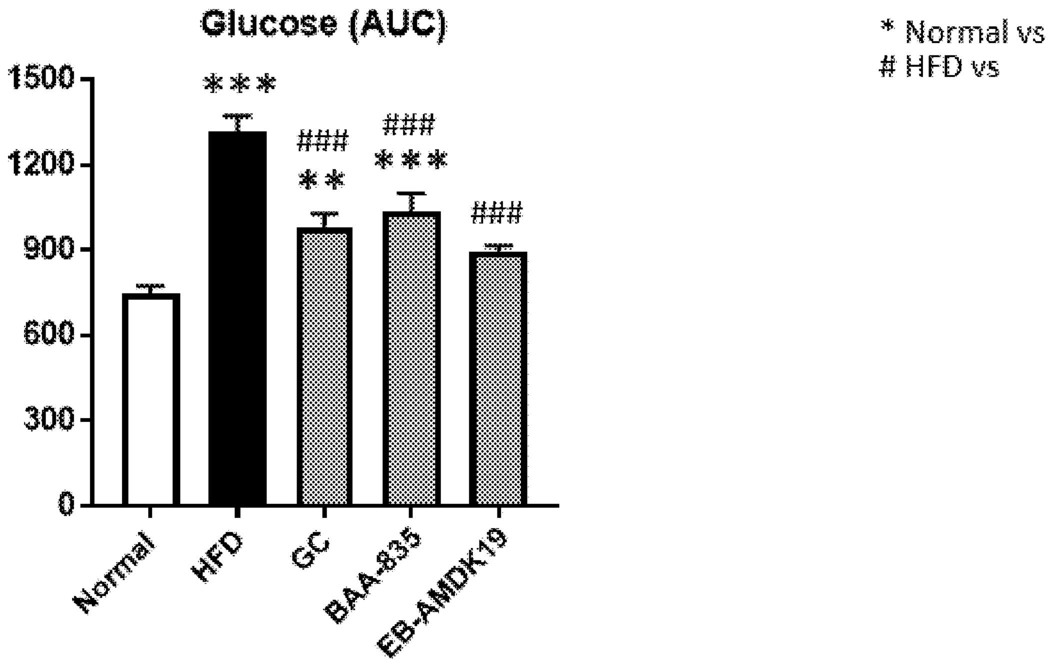
Figure 11C:
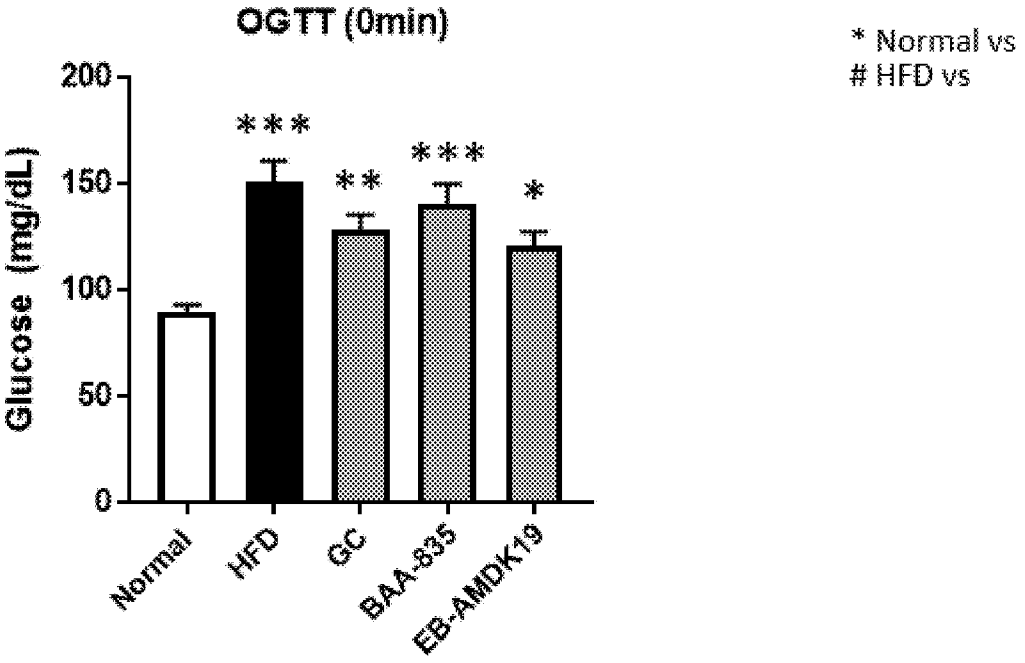
Figure 11D:
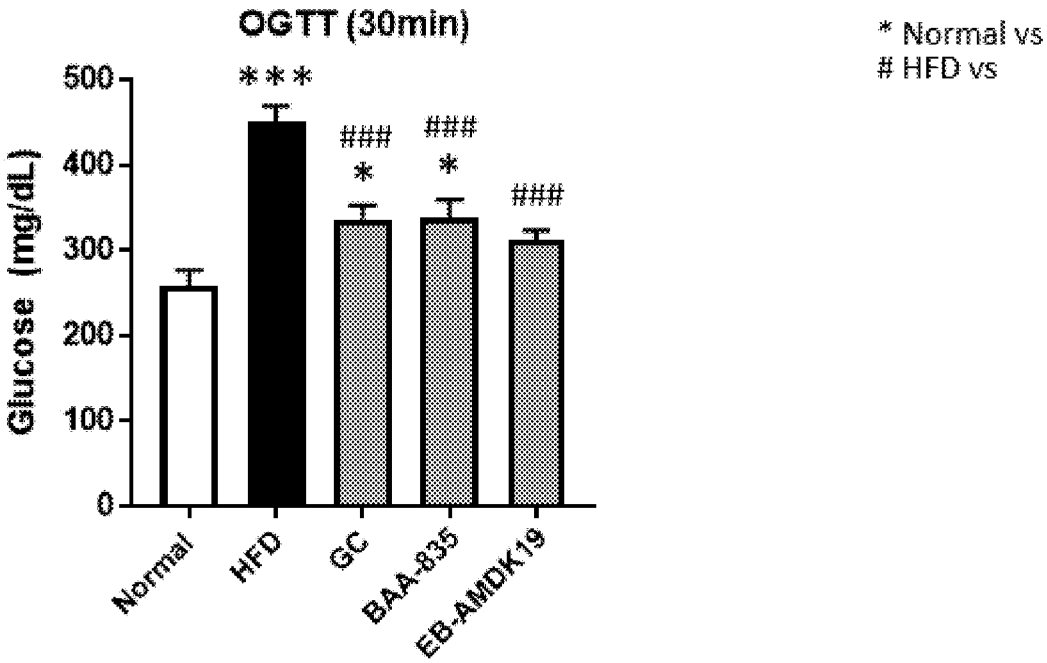
Figure 12A:
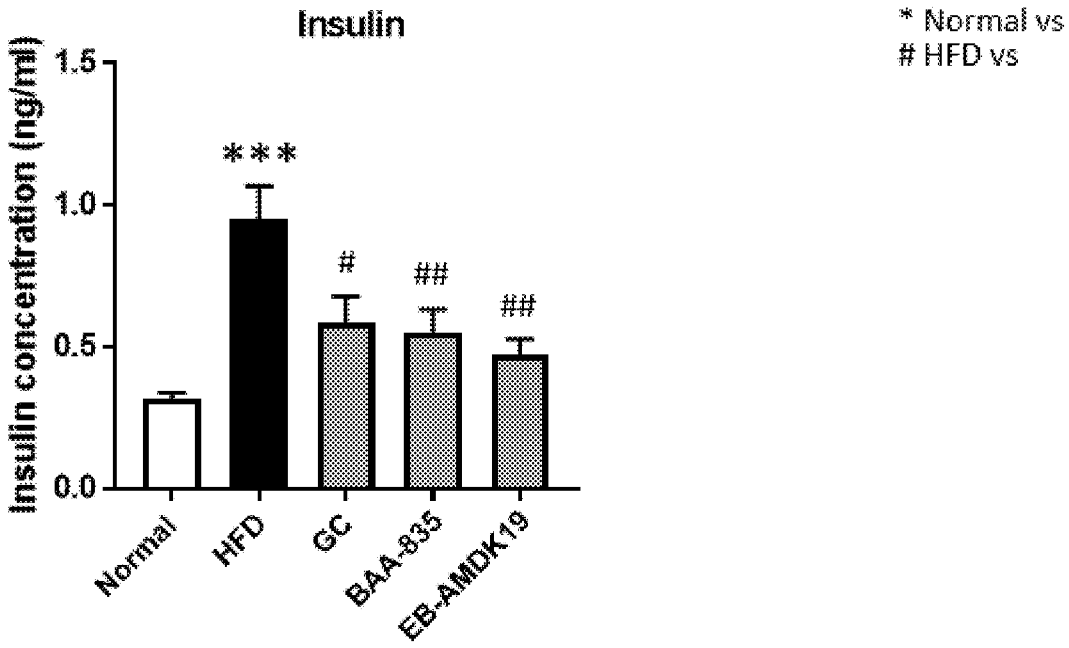
FIGS. 12A-12D show the results of measuring changes in the blood insulin, cholesterol and glutamic pyruvic transaminase (GPT) concentrations in a group administered with the *Akkermansia muciniphila* EB-AMDK19 strain of the present invention, a control group (DM), and a group administered with the *Akkermansia muciniphila* ATCC BAA-835 strain, by ELISA.
Figure 12B:
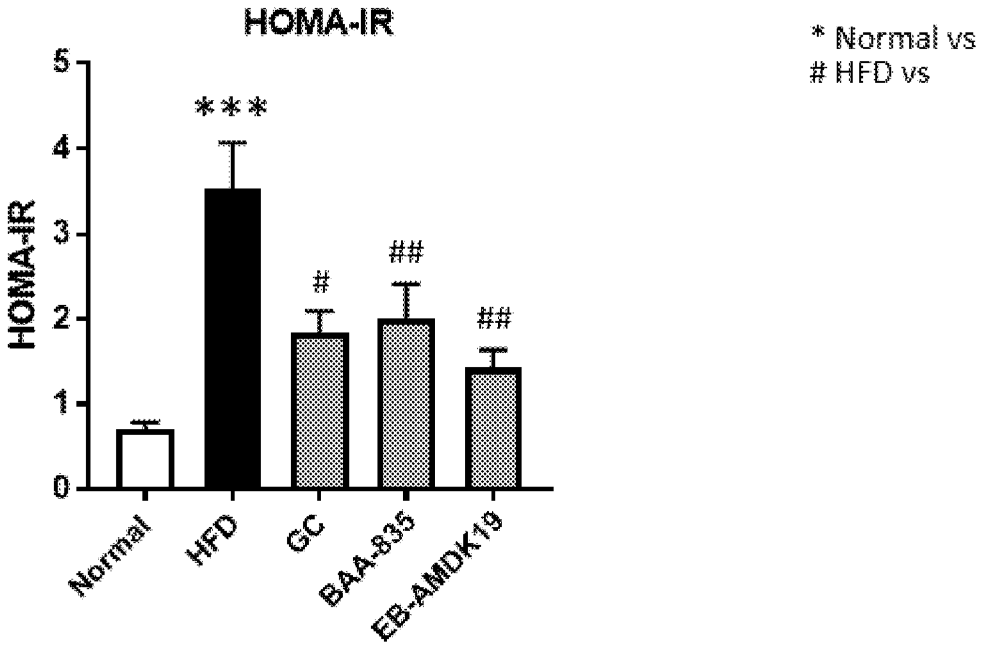
Figure 12C:
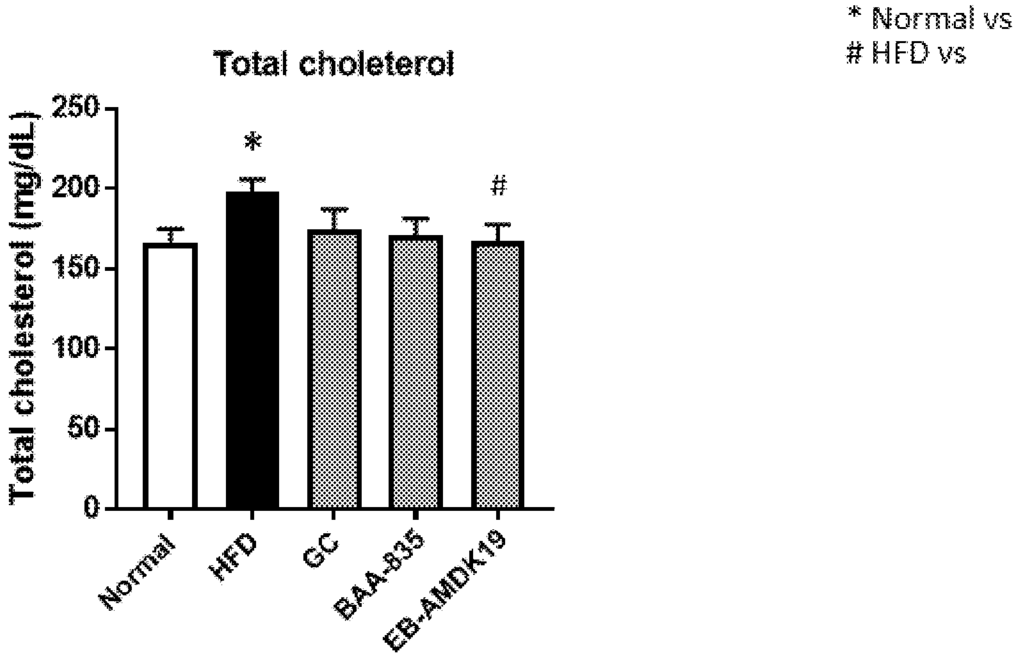
Figure 12D:
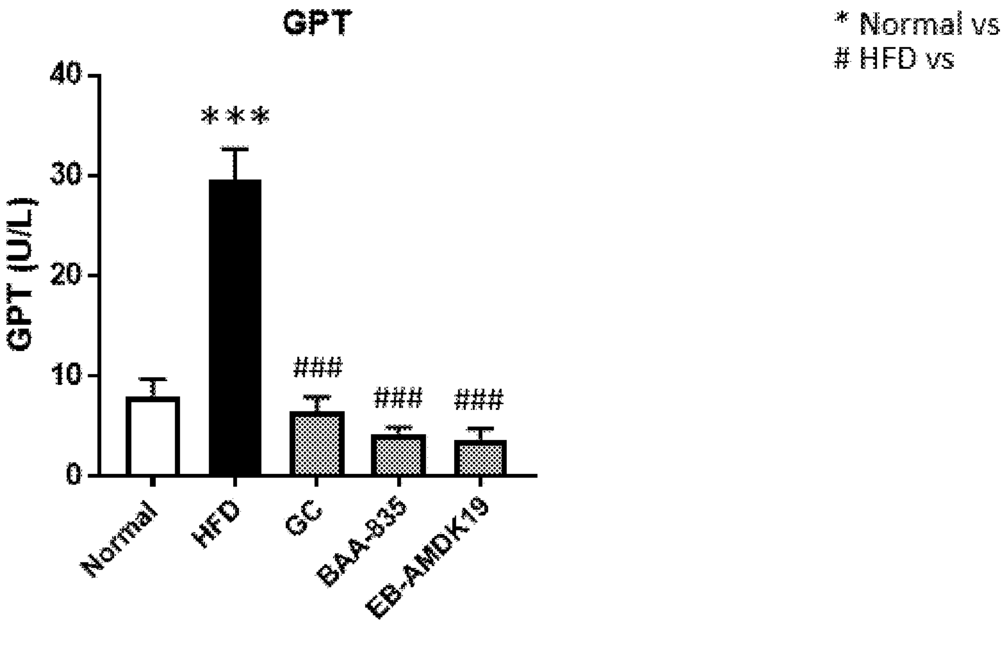

As a result of the analysis, there was a difference in the alpha diversity between the normal group and the high-fat diet group (FIG. 8A). The group administered with the *Akkermansia muciniphila* EB-AMDK19 strain showed some difference in diversity from the normal group, the high-fat diet group, and the group administered with the *Akkermansia muciniphila* BAA-835 strain.

6.2. Linear Discriminant Analysis (LDA) Scores

Figure 18A:
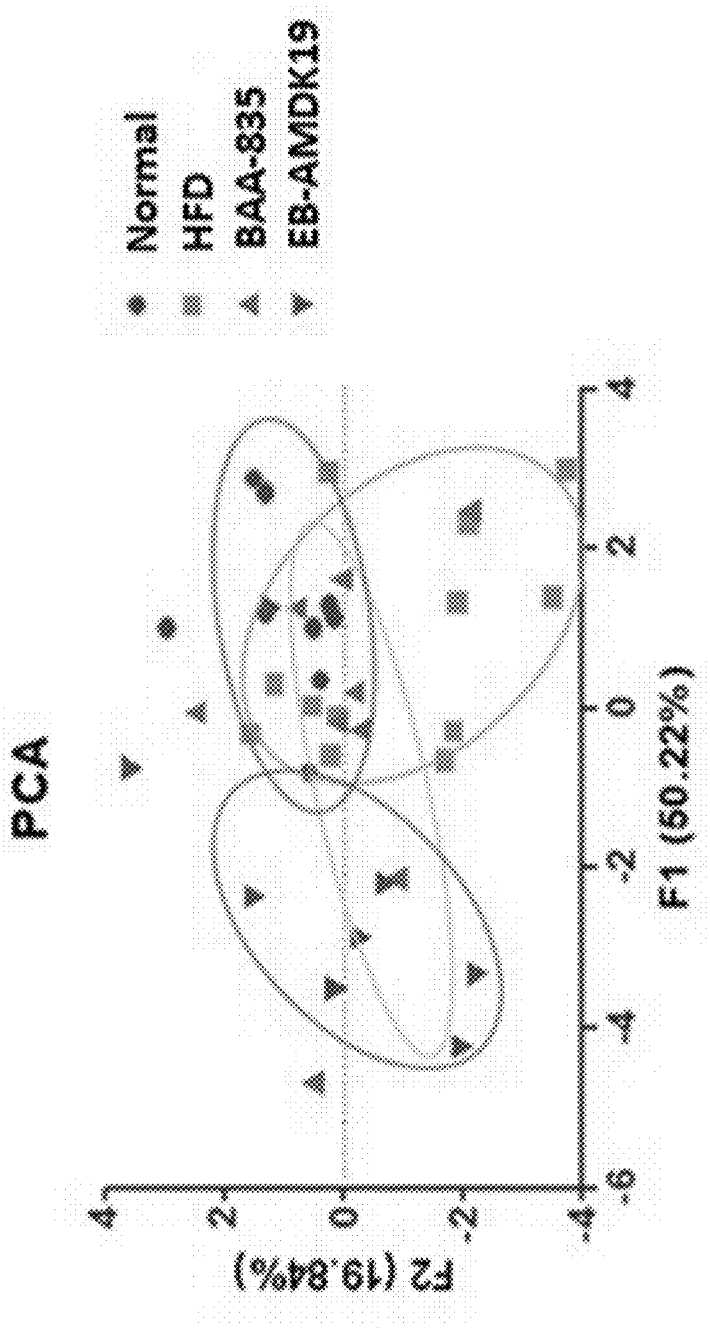
FIGS. 18A-18C are a comparison of linear discriminant analysis results between test groups.
Figure 18B:
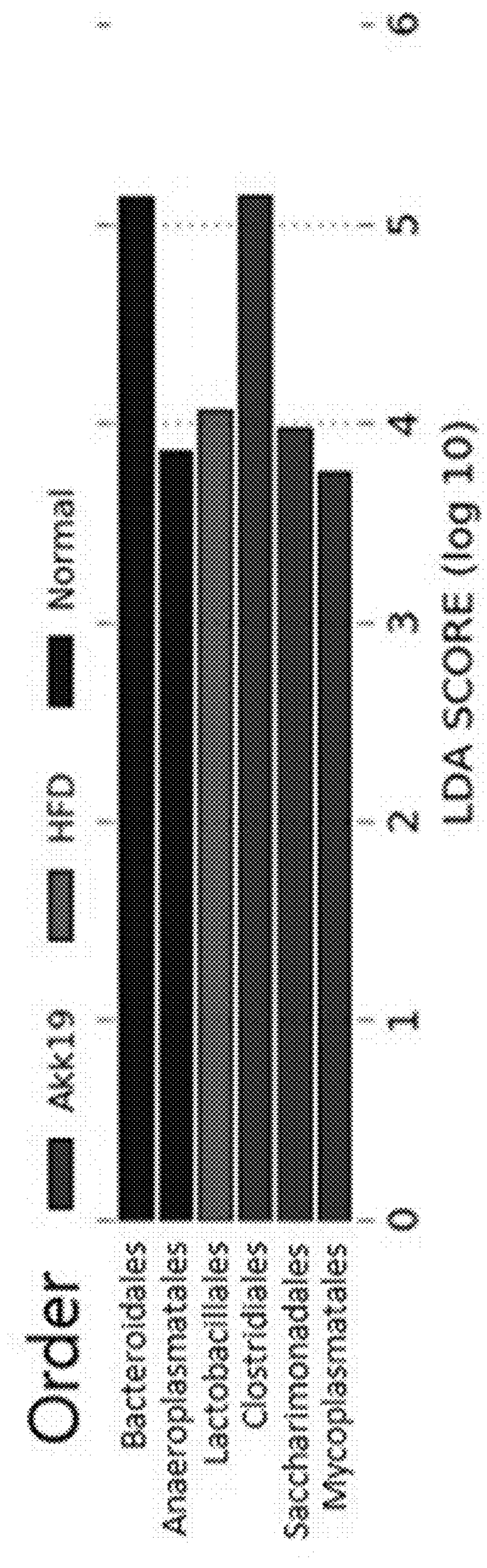
Figure 18C:
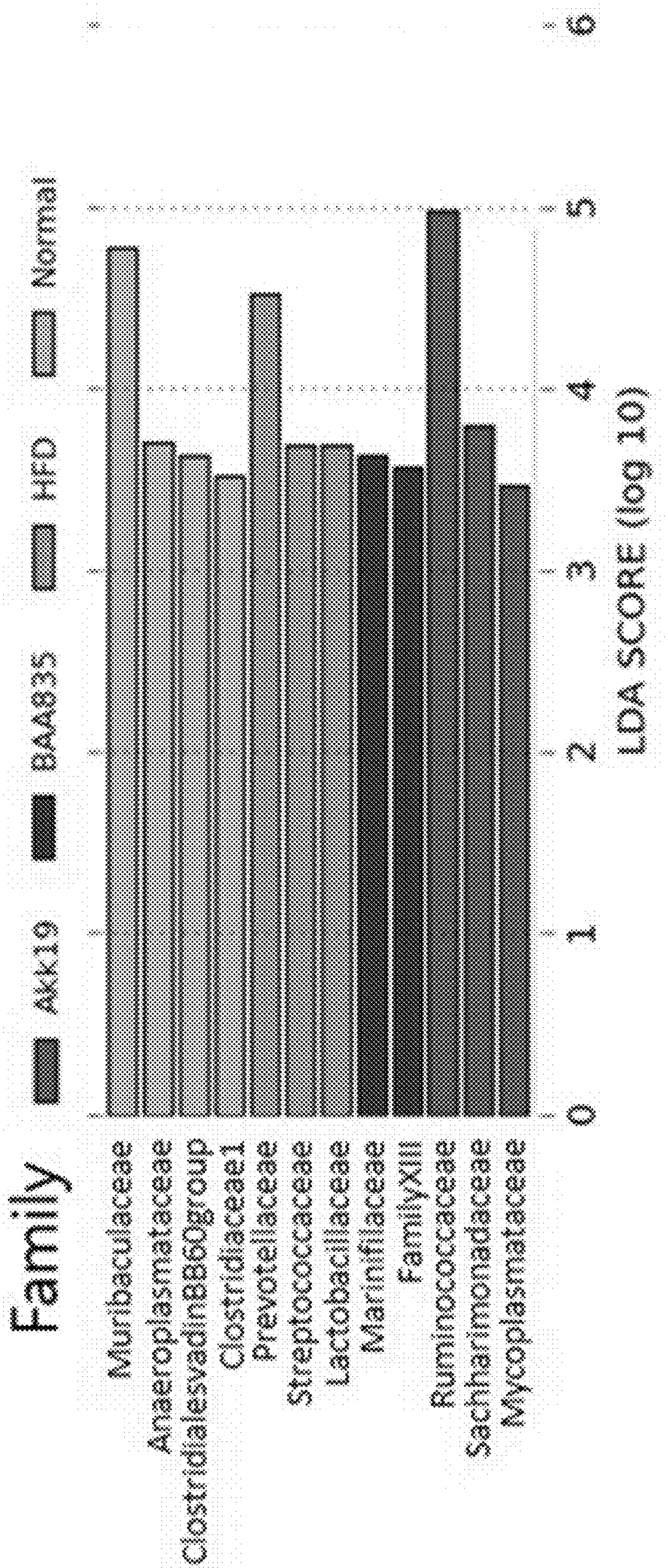
Figure 19:
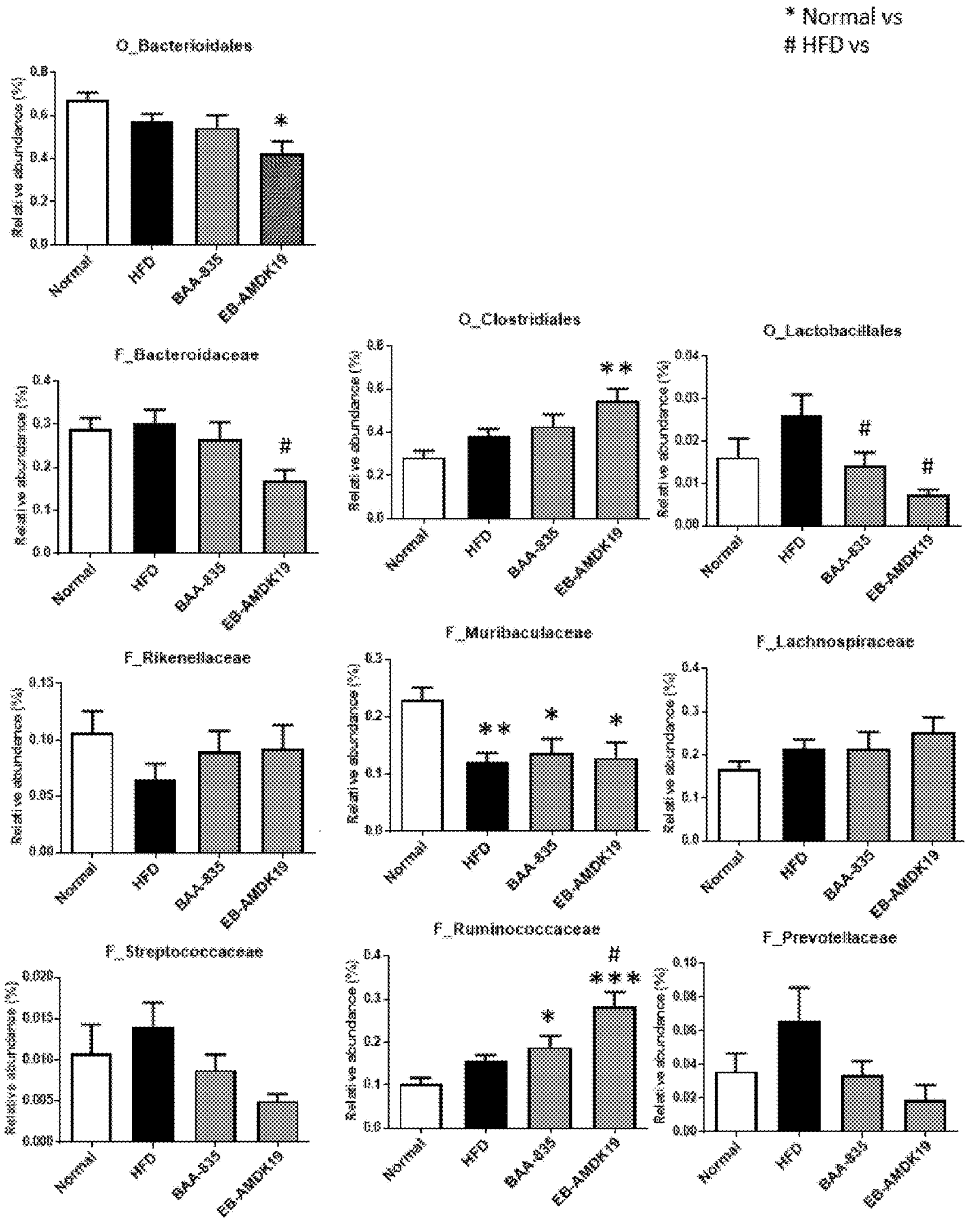
FIG. 19 depicts graphs showing the relative abundance of intestinal microbiomes following administration of the *Akkermansia muciniphila* ATCC BAP-835 strain (BAA-835) and the *Akkermansia muciniphila* EB-AMDK19 strain of the present invention (EB-AMDK19) in one Example of the present invention.

In order to compare the beta diversity between the experimental groups, microorganisms having many differences in LDA scores between the groups were analyzed at the order and family levels (see FIGS. 18A, 18B, and 19). As a result, it can be seen that the normal group showed higher abundances of Muribaculaceae, Anaeroplasmataceae, Clostridiaceae and the like compared to other groups. The high-fat diet group showed higher abundances of Lactobacillales, Prevotellaceae, Streptococcaceae and Lactobacillaceae compared to other groups, and the group administered with the *Akkermansia muciniphila* BAA-835 strain showed higher abundances of Marinifilaceae and the like compared to other groups. The group administered with the *Akkermansia muciniphila* EB-AMDK19 showed relatively high abundances of Clostridiales, Saccharimonadales, Mycoplasmatales, Ruminococcaceae, Saccharimonadaceae and Mycoplasmataceae. As a result of the relative abundance analysis of the microorganisms, it was observed that changes in the high-fat diet group compared to the normal group were observed, and Lactobacillales at the order level and Rikenellaceae, Prevotellaceae and Streptococcaceae at the family level were restored to the levels of the normal group microorganisms in the group administered with the EB-AMDK19 strain.

Taking the above results together, it can be seen that the strain and pharmaceutical composition of the present invention can be effectively used to improve carbohydrate and lipid metabolisms for the treatment of obesity.

The embodiments disclosed herein are only illustrative of preferred embodiments and are not intended to limit the scope of the present invention. It will be apparent to those skilled in the art that the present invention may be modified or altered in various forms without departing from the spirit and scope thereof. The scope of protection of the present invention should be defined by the appended claims, and the above modifications and variations are intended to fall within the scope of protection of the present invention.

[Microorganism Deposit Accession Number]

Depository authority: Korean Collection for Type Cultures

Accession number: KCTC 13761BP

Deposit date: Dec. 5, 2018

Depository address: 181, Ipsin-gil Jeongeup-si Jeollabuk-do, 56212, Republic of Korea.

Applicant agrees that upon allowance and issuance of this application into a United States Patent, restriction on availability of the deposits which are described in the specification of the above-identified application and the accessions were recognized under the terms of the Budapest Treaty on the International Recognition of the Deposit of Microorganisms for the Purpose of Patent Procedure, will be irrevocably removed; agrees that the microorganism designated in this application will be maintained for a period of 30 years, or 5 years after the last request for the deposit, or for the effective life of any patent which issues on the above-identified Application, whichever is longer; agrees that if the deposits become non-viable, they will be replaced; and assures access to the deposits to one determined by the Commissioner to be entitled thereto under 37 C.F.R. § 1.14 and 35 U.S.C. § 122.

The invention claimed is:

1. A pharmaceutical composition comprising an enteric-coated *Akkermansia muciniphila* EB-AMDK19 strain of accession number KCTC 13761BP, an enteric-coated culture of the strain, an enteric-coated dried powder of the strain, or an enteric-coated dried powder of the culture, wherein the enteric coating comprises a coating agent selected from the group consisting of a dimethylaminoethyl methacrylate-methacrylic acid copolymer, polyvinylacetal diethylaminoacetate, an ethylacrylate-methacrylic acid copolymer, and an ethylacrylate-methylmethacrylate-chlorotrimethylammonium ethylmethacrylate copolymer.

2. The pharmaceutical composition of claim 1, wherein the enteric-coated *Akkermansia muciniphila* EB-AMDK19 strain of accession number KCTC 13761BP comprises a 16s rRNA gene of SEQ ID NO: 1.

3. The pharmaceutical composition of claim 1, which comprises the enteric-coated *Akkermansia muciniphila* EB-AMDK19 strain of accession number KCTC 13761BP in a probiotic form or a pasteurized form.

4. The pharmaceutical composition of claim 1, which comprises the enteric-coated *Akkermansia muciniphila* EB-AMDK19 strain of accession number KCTC 13761BP at a concentration of $10^8$ to $10^{12}$ CFU/g of the composition, or the enteric-coated culture thereof containing viable cells or pasteurized cells of the *Akkermansia muciniphila* EB-AMDK19 strain of accession number KCTC 13761BP at a concentration of $10^8$ to $10^{12}$ cells/g of the composition.

5. A food composition comprising an enteric-coated *Akkermansia muciniphila* EB-AMDK19 strain of accession number KCTC 13761 BP, an enteric-coated culture of the strain, an enteric-coated dried powder of the strain, or an enteric-coated dried powder of the culture, wherein the enteric coating comprises a coating agent selected from the group consisting of a dimethylaminoethyl methacrylate-methacrylic acid copolymer, polyvinylacetal diethylaminoacetate, an ethylacrylate-methacrylic acid copolymer, and an ethylacrylate-methylmethacrylate-chlorotrimethylammonium ethylmethacrylate copolymer.

6. A method for treating dyslipidemia or increasing secretion of glucagon like peptide-1 (GLP-1) comprising administering to a subject in need thereof an effective amount of a composition comprising an isolated *Akkermansia muciniphila* EB-AMDK19 strain of accession number KCTC 13761BP, a culture thereof, a dried powder of the isolated strain, or a dried powder of the culture.

7. The method of claim 6, wherein the *Akkermansia muciniphila* EB-AMDK19 strain of accession number KCTC 13761BP comprises a 16s rRNA gene of SEQ ID NO: 1.

8. The method of claim 6, wherein the composition comprises the enteric-coated *Akkermansia muciniphila* EB-AMDK19 strain of accession number KCTC 13761BP in a probiotic form or a pasteurized form.

9. The method of claim 6, wherein the composition comprises the enteric-coated *Akkermansia muciniphila* EB-AMDK19 strain of accession number KCTC 13761BP at a concentration of $10^8$ to $10^{12}$ CFU/g of the composition, or the enteric-coated culture thereof containing viable cells or pasteurized cells of the *Akkermansia muciniphila* EB-AMDK19 strain of accession number KCTC 13761BP at a concentration of $10^8$ to $10^{12}$ cells/g of the composition.

10. The pharmaceutical composition of claim 1, wherein the enteric coating further comprises a coating agent selected from the group consisting of methyl cellulose, hydroxypropyl methyl cellulose, polyvinylpyrrolidone, and polyethylene glycol.

11. The food composition of claim 5, wherein the enteric coating further comprises a coating agent selected from the group consisting of methyl cellulose, hydroxypropyl methyl cellulose, polyvinylpyrrolidone, and polyethylene glycol.

* * * * *

SEQUENCE LISTING

```
<160> NUMBER OF SEQ ID NOS: 58

<210> SEQ ID NO 1
<211> LENGTH: 1464
<212> TYPE: DNA
<213> ORGANISM: Unknown
<220> FEATURE:
<223> OTHER INFORMATION: Akkermansia muciniphila

<400> SEQUENCE: 1

aacgaacgct ggcggcgtgg ataagacatg caagtcgaac gagagaattg ctagcttgct      60

aataattctc tagtggcgca cgggtgagta acacgtgagt aacctgcccc cgagagcggg     120

atagccctgg gaaactggga ttaataccgc atagtatcga aagattaaag cagcaatgcg     180

cttggggatg ggctcgcggc ctattagtta gttggtgagg taacggctca ccaaggcgat     240

gacgggtagc cggtctgaga ggatgtccgg ccacactgga actgagacac ggtccagaca     300

cctacgggtg gcagcagtcg agaatcattc acaatggggg aaaccctgat ggtgcgacgc     360

cgcgtggggg aatgaaggtc ttcggattgt aaacccctgt catgtgggag caaattaaaa     420
```

```
agatagtacc acaagaggaa gagacggcta actctgtgcc agcagccgcg gtaatacaga    480

ggtctcaagc gttgttcgga atcactgggc gtaaagcgtg cgtaggctgt ttcgtaagtc    540

gtgtgtgaaa ggcgcgggct caacccgcgg acggcacatg atactgcgag actagagtaa    600

tggaggggga accggaattc tcggtgtagc agtgaaatgc gtagatatcg agaggaacac    660

tcgtggcgaa ggcgggttcc tggacattaa ctgacgctga ggcacgaagg ccaggggagc    720

gaaagggatt agatacccct gtagtcctgg cagtaaacgg tgcacgcttg gtgtgcgggg    780

aatcgacccc ctgcgtgccg gagctaacgc gttaagcgtg ccgcctgggg agtacggtcg    840

caagattaaa actcaaagaa attgacgggg acccgcacaa gcggtggagt atgtggctta    900

attcgatgca acgcgaagaa ccttacctgg gcttgacatg taatgaacaa catgtgaaag    960

catgcgactc ttcggaggcg ttacacaggt gctgcatggc cgtcgtcagc tcgtgtcgtg   1020

agatgtttgg ttaagtccag caacgagcgc aacccctgtt gccagttacc agcacgtgaa   1080

ggtggggact ctggcgagac tgcccagatc aactgggagg aaggtgggga cgacgtcagg   1140

tcagtatggc ccttatgccc agggctgcac acgtactaca atgcccagta cagagggggc   1200

cgaagccgcg aggcggagga aatcctgaaa actgggccca gttcggactg taggctgcaa   1260

cccgcctaca cgaagccgga atcgctagta atggcgcatc agctacggcg ccgtgaatac   1320

gttcccgggt cttgtacaca ccgcccgtca catcatggaa gccggtcgca cccgaagtat   1380

ctgaagccaa ccgcaaggag gcagggtcct aaggtgagac tggtaactgg gatgaagtcg   1440

taacaaggta gccgtagggg aacc                                          1464
```

<210> SEQ ID NO 2
<211> LENGTH: 22
<212> TYPE: DNA
<213> ORGANISM: Artificial Sequence
<220> FEATURE:
<223> OTHER INFORMATION: ERIC-1 primer Forward

<400> SEQUENCE: 2
atgtaagctc ctggggattc ac 22

<210> SEQ ID NO 3
<211> LENGTH: 22
<212> TYPE: DNA
<213> ORGANISM: Artificial Sequence
<220> FEATURE:
<223> OTHER INFORMATION: ERIC-2 primer Reverse

<400> SEQUENCE: 3
aagtaagtga ctggggtgag cg 22

<210> SEQ ID NO 4
<211> LENGTH: 15
<212> TYPE: DNA
<213> ORGANISM: Artificial Sequence
<220> FEATURE:
<223> OTHER INFORMATION: (GTG)5 Forward/Reverse

<400> SEQUENCE: 4
gtggtggtgg tggtg 15

<210> SEQ ID NO 5
<211> LENGTH: 20
<212> TYPE: DNA
<213> ORGANISM: Artificial Sequence
<220> FEATURE:

<223> OTHER INFORMATION: 27F primer Forward

<400> SEQUENCE: 5
agagtttgat cmtggctcag 20

<210> SEQ ID NO 6
<211> LENGTH: 20
<212> TYPE: DNA
<213> ORGANISM: Artificial Sequence
<220> FEATURE:
<223> OTHER INFORMATION: 1541R primer Reverse

<400> SEQUENCE: 6
aaggaggtga tccagccgca 20

<210> SEQ ID NO 7
<211> LENGTH: 24
<212> TYPE: DNA
<213> ORGANISM: Artificial Sequence
<220> FEATURE:
<223> OTHER INFORMATION: GAPDH primer Forward

<400> SEQUENCE: 7
gacatcaaga aggtggtgaa gcag 24

<210> SEQ ID NO 8
<211> LENGTH: 24
<212> TYPE: DNA
<213> ORGANISM: Artificial Sequence
<220> FEATURE:
<223> OTHER INFORMATION: IL-8 primer Forward

<400> SEQUENCE: 8
ataccaggaa atgagcttga caaa 24

<210> SEQ ID NO 9
<211> LENGTH: 22
<212> TYPE: DNA
<213> ORGANISM: Artificial Sequence
<220> FEATURE:
<223> OTHER INFORMATION: IL-8 primer Forward

<400> SEQUENCE: 9
ttttgccaag gagtgctaaa ga 22

<210> SEQ ID NO 10
<211> LENGTH: 21
<212> TYPE: DNA
<213> ORGANISM: Artificial Sequence
<220> FEATURE:
<223> OTHER INFORMATION: TNF primer Forward

<400> SEQUENCE: 10
aaccctctgc acccagtttt c 21

<210> SEQ ID NO 11
<211> LENGTH: 20
<212> TYPE: DNA
<213> ORGANISM: Artificial Sequence
<220> FEATURE:
<223> OTHER INFORMATION: TNF primer Forward

<400> SEQUENCE: 11
agcccatgtt gtagcaaacc 20

-continued

```
<210> SEQ ID NO 12
<211> LENGTH: 20
<212> TYPE: DNA
<213> ORGANISM: Artificial Sequence
<220> FEATURE:
<223> OTHER INFORMATION: TNF primer Reverse

<400> SEQUENCE: 12

tgaggtacag gccctctgat                                                20


<210> SEQ ID NO 13
<211> LENGTH: 20
<212> TYPE: DNA
<213> ORGANISM: Artificial Sequence
<220> FEATURE:
<223> OTHER INFORMATION: IL-6 primer Forward

<400> SEQUENCE: 13

aaagaggcac tggcagaaaa                                                20


<210> SEQ ID NO 14
<211> LENGTH: 20
<212> TYPE: DNA
<213> ORGANISM: Artificial Sequence
<220> FEATURE:
<223> OTHER INFORMATION: IL-6 primer Reverse

<400> SEQUENCE: 14

tttcaccagg caagtctcct                                                20


<210> SEQ ID NO 15
<211> LENGTH: 20
<212> TYPE: DNA
<213> ORGANISM: Artificial Sequence
<220> FEATURE:
<223> OTHER INFORMATION: IL-1 primer Forward

<400> SEQUENCE: 15

ccgaccacca ctacagcaag                                                20


<210> SEQ ID NO 16
<211> LENGTH: 20
<212> TYPE: DNA
<213> ORGANISM: Artificial Sequence
<220> FEATURE:
<223> OTHER INFORMATION: IL-1 primer Reverse

<400> SEQUENCE: 16

gggcagggaa ccagcatctt                                                20


<210> SEQ ID NO 17
<211> LENGTH: 24
<212> TYPE: DNA
<213> ORGANISM: Artificial Sequence
<220> FEATURE:
<223> OTHER INFORMATION: GAPDH primer Forward

<400> SEQUENCE: 17

gacatcaaga aggtggtgaa gcag                                           24


<210> SEQ ID NO 18
<211> LENGTH: 24
<212> TYPE: DNA
<213> ORGANISM: Artificial Sequence
<220> FEATURE:
<223> OTHER INFORMATION: GAPDH primer Reverse
```

<400> SEQUENCE: 18
ataccaggaa atgagcttga caaa 24

<210> SEQ ID NO 19
<211> LENGTH: 23
<212> TYPE: DNA
<213> ORGANISM: Artificial Sequence
<220> FEATURE:
<223> OTHER INFORMATION: PPAR primer Forward

<400> SEQUENCE: 19
caagaatacc aaagtgcgat caa 23

<210> SEQ ID NO 20
<211> LENGTH: 26
<212> TYPE: DNA
<213> ORGANISM: Artificial Sequence
<220> FEATURE:
<223> OTHER INFORMATION: PPAR primer Reverse

<400> SEQUENCE: 20
gagctgggtc ttttcagaat aataag 26

<210> SEQ ID NO 21
<211> LENGTH: 20
<212> TYPE: DNA
<213> ORGANISM: Artificial Sequence
<220> FEATURE:
<223> OTHER INFORMATION: C/EBP primer Forward

<400> SEQUENCE: 21
agcaacgagt accgggtacg 20

<210> SEQ ID NO 22
<211> LENGTH: 21
<212> TYPE: DNA
<213> ORGANISM: Artificial Sequence
<220> FEATURE:
<223> OTHER INFORMATION: C/EBP primer Reverse

<400> SEQUENCE: 22
tgtttggctt tatctcggct c 21

<210> SEQ ID NO 23
<211> LENGTH: 26
<212> TYPE: DNA
<213> ORGANISM: Artificial Sequence
<220> FEATURE:
<223> OTHER INFORMATION: aP2 primer Forward

<400> SEQUENCE: 23
agtgaaaact tcgatgatta catgaa 26

<210> SEQ ID NO 24
<211> LENGTH: 19
<212> TYPE: DNA
<213> ORGANISM: Artificial Sequence
<220> FEATURE:
<223> OTHER INFORMATION: aP2 primer Reverse

<400> SEQUENCE: 24
gcctgccact ttccttgtg 19

<210> SEQ ID NO 25
<211> LENGTH: 27

<212> TYPE: DNA
<213> ORGANISM: Artificial Sequence
<220> FEATURE:
<223> OTHER INFORMATION: CD36 primer Forward

<400> SEQUENCE: 25
ttgtacctat actgtggcta aatgaga 27

<210> SEQ ID NO 26
<211> LENGTH: 24
<212> TYPE: DNA
<213> ORGANISM: Artificial Sequence
<220> FEATURE:
<223> OTHER INFORMATION: CD36 primer Reverse

<400> SEQUENCE: 26
cttgtgtttt gaacatttct gctt 24

<210> SEQ ID NO 27
<211> LENGTH: 20
<212> TYPE: DNA
<213> ORGANISM: Artificial Sequence
<220> FEATURE:
<223> OTHER INFORMATION: FAS primer Forward

<400> SEQUENCE: 27
aggggtcgac ctggtcctca 20

<210> SEQ ID NO 28
<211> LENGTH: 20
<212> TYPE: DNA
<213> ORGANISM: Artificial Sequence
<220> FEATURE:
<223> OTHER INFORMATION: FAS primer Reverse

<400> SEQUENCE: 28
gccatgccca gagggtggtt 20

<210> SEQ ID NO 29
<211> LENGTH: 20
<212> TYPE: DNA
<213> ORGANISM: Artificial Sequence
<220> FEATURE:
<223> OTHER INFORMATION: ACC1 primer Forward

<400> SEQUENCE: 29
cctccgtcag ctcagataca 20

<210> SEQ ID NO 30
<211> LENGTH: 22
<212> TYPE: DNA
<213> ORGANISM: Artificial Sequence
<220> FEATURE:
<223> OTHER INFORMATION: ACC1 primer Reverse

<400> SEQUENCE: 30
tttactaggt gcaagccaga ca 22

<210> SEQ ID NO 31
<211> LENGTH: 20
<212> TYPE: DNA
<213> ORGANISM: Artificial Sequence
<220> FEATURE:
<223> OTHER INFORMATION: LPL primer Forward

<400> SEQUENCE: 31

-continued ttgccctaag gacccctgaa 20

<210> SEQ ID NO 32
<211> LENGTH: 23
<212> TYPE: DNA
<213> ORGANISM: Artificial Sequence
<220> FEATURE:
<223> OTHER INFORMATION: LPL primer Reverse

<400> SEQUENCE: 32
acagagtctg ctaatccagg aat 23

<210> SEQ ID NO 33
<211> LENGTH: 21
<212> TYPE: DNA
<213> ORGANISM: Artificial Sequence
<220> FEATURE:
<223> OTHER INFORMATION: LDLR primer Forward

<400> SEQUENCE: 33
tgactcagac gaacaaggct g 21

<210> SEQ ID NO 34
<211> LENGTH: 21
<212> TYPE: DNA
<213> ORGANISM: Artificial Sequence
<220> FEATURE:
<223> OTHER INFORMATION: LDLR primer Reverse

<400> SEQUENCE: 34
atctaggcaa tctcggtctc c 21

<210> SEQ ID NO 35
<211> LENGTH: 24
<212> TYPE: DNA
<213> ORGANISM: Artificial Sequence
<220> FEATURE:
<223> OTHER INFORMATION: GAPDH primer Forward

<400> SEQUENCE: 35
gacatcaaga aggtggtgaa gcag 24

<210> SEQ ID NO 36
<211> LENGTH: 24
<212> TYPE: DNA
<213> ORGANISM: Artificial Sequence
<220> FEATURE:
<223> OTHER INFORMATION: GAPDH primer Reverse

<400> SEQUENCE: 36
ataccaggaa atgagcttga caaa 24

<210> SEQ ID NO 37
<211> LENGTH: 20
<212> TYPE: DNA
<213> ORGANISM: Artificial Sequence
<220> FEATURE:
<223> OTHER INFORMATION: TLR2 primer Forward

<400> SEQUENCE: 37
aaggaggtgc ggactgtttc 20

<210> SEQ ID NO 38
<211> LENGTH: 19
<212> TYPE: DNA
<213> ORGANISM: Artificial Sequence
<220> FEATURE:
<223> OTHER INFORMATION: TLR2 primer Reverse

<400> SEQUENCE: 38
gagccaaaga gctcgtagc 19

<210> SEQ ID NO 39
<211> LENGTH: 23
<212> TYPE: DNA
<213> ORGANISM: Artificial Sequence
<220> FEATURE:
<223> OTHER INFORMATION: TLR4 primer Forward

<400> SEQUENCE: 39
cctgatgaca ttccttcttc aac 23

<210> SEQ ID NO 40
<211> LENGTH: 26
<212> TYPE: DNA
<213> ORGANISM: Artificial Sequence
<220> FEATURE:
<223> OTHER INFORMATION: TLR4 primer Reverse

<400> SEQUENCE: 40
ttgtttcaat ttcacacctg gataaa 26

<210> SEQ ID NO 41
<211> LENGTH: 21
<212> TYPE: DNA
<213> ORGANISM: Artificial Sequence
<220> FEATURE:
<223> OTHER INFORMATION: GLP-1 primer Forward

<400> SEQUENCE: 41
ggcacattca ccagcgacta c 21

<210> SEQ ID NO 42
<211> LENGTH: 20
<212> TYPE: DNA
<213> ORGANISM: Artificial Sequence
<220> FEATURE:
<223> OTHER INFORMATION: GLP-1 primer Reverse

<400> SEQUENCE: 42
caatggcgac ttcttctggg 20

<210> SEQ ID NO 43
<211> LENGTH: 19
<212> TYPE: DNA
<213> ORGANISM: Artificial Sequence
<220> FEATURE:
<223> OTHER INFORMATION: PYY primer Forward

<400> SEQUENCE: 43
cggcagcggt atggaaaaa 19

<210> SEQ ID NO 44
<211> LENGTH: 23
<212> TYPE: DNA
<213> ORGANISM: Artificial Sequence
<220> FEATURE:
<223> OTHER INFORMATION: PYY primer Reverse

<400> SEQUENCE: 44
tgtgaagagc agtttggaga aca 23

<210> SEQ ID NO 45
<211> LENGTH: 21
<212> TYPE: DNA
<213> ORGANISM: Artificial Sequence
<220> FEATURE:
<223> OTHER INFORMATION: IL-6 primer Forward

<400> SEQUENCE: 45
cctctggtct tctggagtac c 21

<210> SEQ ID NO 46
<211> LENGTH: 20
<212> TYPE: DNA
<213> ORGANISM: Artificial Sequence
<220> FEATURE:
<223> OTHER INFORMATION: IL-6 primer Reverse

<400> SEQUENCE: 46
actccttctg tgactccagc 20

<210> SEQ ID NO 47
<211> LENGTH: 25
<212> TYPE: DNA
<213> ORGANISM: Artificial Sequence
<220> FEATURE:
<223> OTHER INFORMATION: TNF- primer Forward

<400> SEQUENCE: 47
gaccctcaca ctcagatcat cttct 25

<210> SEQ ID NO 48
<211> LENGTH: 21
<212> TYPE: DNA
<213> ORGANISM: Artificial Sequence
<220> FEATURE:
<223> OTHER INFORMATION: TNF- primer Reverse

<400> SEQUENCE: 48
ccacttggtg gtttgctacg a 21

<210> SEQ ID NO 49
<211> LENGTH: 20
<212> TYPE: DNA
<213> ORGANISM: Artificial Sequence
<220> FEATURE:
<223> OTHER INFORMATION: MCP-1 primer Forward

<400> SEQUENCE: 49
aagagatcag ggagtttgct 20

<210> SEQ ID NO 50
<211> LENGTH: 20
<212> TYPE: DNA
<213> ORGANISM: Artificial Sequence
<220> FEATURE:
<223> OTHER INFORMATION: MCP-1 primer Reverse

<400> SEQUENCE: 50
ctgcctccat caaccacttt 20

<210> SEQ ID NO 51
<211> LENGTH: 20
<212> TYPE: DNA
<213> ORGANISM: Artificial Sequence
<220> FEATURE:
<223> OTHER INFORMATION: IL-10 primer Forward

<400> SEQUENCE: 51
ataactgcac ccacttccca 20

<210> SEQ ID NO 52
<211> LENGTH: 20
<212> TYPE: DNA
<213> ORGANISM: Artificial Sequence
<220> FEATURE:
<223> OTHER INFORMATION: IL-10 primer Reverse

<400> SEQUENCE: 52
gggcatcact tctaccaggt 20

<210> SEQ ID NO 53
<211> LENGTH: 19
<212> TYPE: DNA
<213> ORGANISM: Artificial Sequence
<220> FEATURE:
<223> OTHER INFORMATION: ZO-1 primer Forward

<400> SEQUENCE: 53
tttttgacag ggggagtgg 19

<210> SEQ ID NO 54
<211> LENGTH: 23
<212> TYPE: DNA
<213> ORGANISM: Artificial Sequence
<220> FEATURE:
<223> OTHER INFORMATION: ZO-1 primer Reverse

<400> SEQUENCE: 54
tgctgcagag gtcaaagttc aag 23

<210> SEQ ID NO 55
<211> LENGTH: 19
<212> TYPE: DNA
<213> ORGANISM: Artificial Sequence
<220> FEATURE:
<223> OTHER INFORMATION: Occludin primer Forward

<400> SEQUENCE: 55
atgtccggcc gatgctctc 19

<210> SEQ ID NO 56
<211> LENGTH: 23
<212> TYPE: DNA
<213> ORGANISM: Artificial Sequence
<220> FEATURE:
<223> OTHER INFORMATION: Occludin primer Reverse

<400> SEQUENCE: 56
tttggctgct cttgggtctg tat 23

<210> SEQ ID NO 57
<211> LENGTH: 20
<212> TYPE: DNA
<213> ORGANISM: Artificial Sequence
<220> FEATURE:
<223> OTHER INFORMATION: AM1 primer forward

<400> SEQUENCE: 57
cagcacgtga aggtggggac 20

<210> SEQ ID NO 58

-continued

```
<211> LENGTH: 20
<212> TYPE: DNA
<213> ORGANISM: Artificial Sequence
<220> FEATURE:
<223> OTHER INFORMATION: AM1 primer reverse

<400> SEQUENCE: 58

ccttgcggtt ggcttcagat                                                20
```